United States Patent
Selsted et al.

(10) Patent No.: US 6,300,470 B1
(45) Date of Patent: *Oct. 9, 2001

(54) ANTIBIOTIC CRYPTDIN PEPTIDES AND METHODS OF THEIR USE

(75) Inventors: Michael E. Selsted, Irvine, CA (US); Andre J. Ouellette, Lynn, MA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/397,386

(22) Filed: Sep. 15, 1999

Related U.S. Application Data

(63) Continuation of application No. 09/015,968, filed on Jan. 30, 1998, now Pat. No. 6,057,425, which is a continuation of application No. 08/482,279, filed on Jun. 7, 1995, now Pat. No. 5,840,498, which is a continuation of application No. 08/342,268, filed on Nov. 18, 1994, now Pat. No. 5,844,072, which is a continuation-in-part of application No. 07/930,649, filed on Aug. 14, 1992, now Pat. No. 5,422,424, which is a continuation-in-part of application No. 07/889,020, filed on May 26, 1992, now abandoned.

(51) Int. Cl.⁷ .................................................. A61K 38/00

(52) U.S. Cl. ........................ 530/324; 530/328; 530/329; 530/330; 530/333; 530/334; 530/335; 530/387.1; 514/2; 514/12; 514/15; 514/16; 514/17; 514/18; 514/21; 435/7.1; 536/23.1; 436/503; 436/547

(58) Field of Search ...................................... 530/324, 328, 529/329, 330, 333, 334, 335, 387.1; 514/2, 12, 15, 16, 17, 18; 435/7.1; 536/23.1; 436/503, 547

(56) References Cited

U.S. PATENT DOCUMENTS

| | | | |
|---|---|---|---|
| 4,304,715 | 12/1981 | Hudson et al. | 260/112.5 |
| 4,543,252 | 9/1985 | Lehrer et al. | 514/12 |
| 4,659,692 | 4/1987 | Lehrer et al. | 514/12 |
| 4,705,777 | 11/1987 | Lehrer et al. | 514/12 |
| 5,032,574 | 7/1991 | Wilde et al. | 514/12 |
| 5,191,015 | 3/1993 | Sheppard et al. | 525/54.1 |
| 5,237,051 | 8/1993 | Garbers et al. | 530/350 |
| 5,422,424 | 6/1995 | Selsted et al. | 530/324 |
| 5,436,155 | 7/1995 | Bell et al. | 435/252.3 |
| 5,438,121 | 8/1995 | Barcle et al. | 530/399 |
| 5,459,235 | 10/1995 | Selsted et al. | 530/300 |
| 5,731,149 | 3/1998 | Selsted et al. | 435/6 |
| 5,840,498 | 11/1998 | Selsted et al. | 435/7.1 |
| 5,844,072 | 12/1998 | Selsted et al. | 530/300 |
| 5,861,378 | 1/1999 | Iwanaga et al. | 514/12 |

FOREIGN PATENT DOCUMENTS

| | | |
|---|---|---|
| WO 93/24139 | 12/1993 | (WO) . |
| WO 93/24513 | 12/1993 | (WO) . |
| WO 94/21672 | 9/1994 | (WO) . |
| WO 96/04373 | 2/1996 | (WO) . |
| WO 96/16075 | 5/1996 | (WO) . |

OTHER PUBLICATIONS

Bowie et al., *Science*, vol. 247, pp. 1306–1310, 1990.*
Houghten et al., *Vaccine* 86, Cold Spring Harbor Laboratory, pp. 21–25, 1986.*
Aley et al., "Killing of Giardia Lamblia by Cryptdins and Cationic Neutrophil Peptides," *Infect. and Immun.*, 62:5397–5403 (1994).
Belcourt, R. et al., "Purification of cationic cystine–rich peptides from rat bone marrow," *Regul. Pept.*, 40:87–100 (1992).
Campbell, "Monoclonal Antibody Technology", *Elsevier Science Pub*. 1–32 (1986).
Chow, et al., "Fmoc Solid Phase Peptide Synthesis of Defensins," *Proceeding of the Sixth Symposium on The Protein Society*, Abstract (1992).
Eisenhauer et al., "Cryptins: Antimicrobial Defensins of the Murine Small Intestine," *Infection and Immunity* 60:3556–3565 (1992).
Ganz et al., "Defensins," *Eur. J. Haematol.*, 44:1–8 (1990).
Huttner et al., "Structure and Diversity of the Murine Cryptdin Gene Family," *Genomics* 19:448–453 (1994).

(List continued on next page.)

Primary Examiner—Christopher S. F. Low
Assistant Examiner—Abdel A. Mohamed
(74) Attorney, Agent, or Firm—Campbell & Flores LLP

(57) ABSTRACT

The present invention provides substantially purified cryptdin peptides having a consensus amino acid sequence:

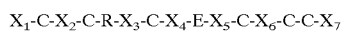

$X_1$-C-$X_2$-C-R-$X_3$-C-$X_4$-E-$X_5$-C-$X_6$-C-C-$X_7$ wherein $X_1$ is 3 to 9 amino acids; $X_2$ is one amino acid, preferably Y, H or R; $X_3$ is 2 or 3 amino acids; $X_4$ is three amino acids; $X_5$ is five amino acids; $X_6$ is 6 to 10 amino acids; and $X_7$ is 0 to 9 amino acids. The invention also provides a substantially purified mouse cryptdin having a consensus amino acid sequence:

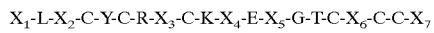

$X_1$-L-$X_2$-C-Y-C-R-$X_3$-C-K-$X_4$-E-$X_5$-G-T-C-$X_6$-C-C-$X_7$ wherein $X_1$ is 3 or 4 amino acids, preferably LRD, LSKK (SEQ ID NO: 1) or LRG; $X_2$ is 1 amino acid, preferably V, L or I; $X_3$ is 3 amino acids, preferably KGH or *RG, where * is S, T, K, I or A; $X_4$ is 2 amino acids, preferably GR, RR or RG; $X_5$ is 3 amino acids, preferably RMN, RVR, RVF HMN or HIN; $X_6$ is 6 to 9 amino acids, preferably GIRFLY (SEQ ID NO: 2) or RNLFLTFVF (SEO ID NO: 3), RRGHLMYTL (SEQ ID NO: 4) or RKGHL*YT* (SEQ ID NO: 5), where * independently is L or M; and $X_7$ is 0 to 3 amino acids, preferably R, S or PRR. The invention also provides cryptdin analogs, which are devoid of one or more amino acids N-terminal to the first cysteine. In addition, the invention provides nucleic acid molecules encoding cryptdin peptides. The invention further provides methods for detecting inflammatory pathologies in a subject and for treating an inflammatory pathology in a subject by administering a pharmaceutical composition containing a cryptdin peptide.

15 Claims, 27 Drawing Sheets

OTHER PUBLICATIONS

Kagan, B.L., "Antimicrobial Defensin Peptides Form Voltage–Dependent Ion–Permeable Channels in Planar Lipid Bilayer Membranes", *Proc. Natl. Acad. Sci., USA,* 87:210–214 (1990).

Maurer, P.H. and Callahan, H.J., "Proteins and Polypeptides as Antigens," *Methods in Enzymology,* 70:49–70 (1980).

Miller et al., "Purification and Characterization of a Secreted Paneth Cell Defensin Using phoP Mutants of Salmonella Typhimurium," ASCB/EMBO Summer Conference, Abstract (1991).

Notification of Transmittal of International Search Report for PCT/US95/13328 mailed Feb. 21, 1996.

Ouellette et al., "Developmental Regulation of Cryptdin, a Corticostatin/Defensin Precursor mRNA in Mouse Small Intestinal Crypt Epithelium," *J. Cell. Biol.,* 108:1687–1695 (1989).

Ouellette et al. "Purification and Primary Structure of Murine Cryptdin–1, a Paenth Cell Defensin," *FEBS* 304:146–148 (1992).

Ouellette and Lualdi, "A Novel Mouse Gene Family Coding for Catonic, Cysteine–rich Peptides," *J. Biol. Chem.* 265:9831–9837 (1990).

Ouellette et al., "Mouse Paneth Cell Defensins: Primary Structures and Antibacterial Activities of Numerous of Numerous Cryptidin Isoforms," *Infect. and Immun.,* 62:5040–5047 (1994).

Ouellette et al., "Localization of the Cryptidin Locus on Mouse Chromosome 8," *Genomics* 5:233–239 (1989).

Panyutoch et al., *J. Immunological Methods,* 141:149 (1991).

Selsted, Michael E., "Investigational Approaches for Studying the Structures and Biological Functions of Myeloid Antimicrobial Peptides," *Genetic Eng.,* 15:131–147 (1993).

Selsted, Michael A., "Enteric Defensins: Antibiotic Peptide Components of Intestinal Host Defense," *J. Cell Biol.* 118:929–936 (1992).

Talmadge, *Advanced Drug Delivery Reviews,* 10:247–299 (1993).

Traber et al., "Isolation of intestinal epithelial cells for the study of differential gene expression along the crypt–villaus axis," *Am. J. Physiol.,* 260:G895–G903 (1991).

Wimley et al., "Interactions Between Human Defensins and Lipid Bilayers: Evidence for Formation of Multimeric Forces," *Protein Sci.* 3:1362–1373.

Yount, N.Y., et al., "cDNA and Genomic Gloning of beta–Defensins BNBD–4," *Abstracts of the 94th General Meeting of the American Society for Microbilogy,* 94:23–27 (1994).

* cited by examiner

FIG. 8

```
RAT CRYPT-1                     LKQCHCRKF CRPYEKAEGSCRPGLFIKRKICCIQQWTPGRT
RAT CRYPT-2      IGRPVRRCRCRAN CGPKEYATAFCAQGPFKQFKFCCT
RAT CRYPT-3      IRWPWKRCHCRSF CRPYENATSFCAQGLFKQHKFCCLDTWPPRMK

HUMAN HD-5  TSGSQARATCYCRTGRCATRESLSGVCEISGRL YRLCCR
HUMAN HD-6                AFTCHCRR-SCYSTEYSYGTCTVMGIN HRFCCL

Def CONSENSUS              CxCRxxxCxxxERxxGxCxxxxxxxxCC
```

```
                     1                        25                         50
RAT CRYPT-1 (cDNA)       MKTLVLLSALVLLLAFQVQADPIQEAEEETKTEEQPADEDQDDVSVSFEGPE
RAT CRYPT-2 (genomic)    MKTLVLLSALVLVAYQVQADPIQGAEEETKTEEQPSDEDQDDVSVSFEGPE
RAT CRYPT-3 (cDNA)       MKTLVLLSALVLLLAFQIQADPIQEAEEETKTEEQPADEDQDDVSVSFEGPE
                     51                       75                        100
RAT CRYPT-1              PSALQNLEIGWPLKQCHCRKFCRPYEKAEGSCRPGLFIKRKICCIQQWTPGRT
RAT CRYPT-2              ASALQDFEIGRPVRRCRCRANCGPKEYATAFCAQGPFKQFKFCCT
RAT CRYPT-3              PSALQNLEIRWPWKRCHCRSFCRPYENATSFCAQGLFKQHKFCCLDTWPPRMK
```

FIG. 9A

```
        <----------------|------|------><-|------------><-|------><------------------------>
        <--SIGNAL PEPTIDE--><----------- Exon 1 -------------|--------- Exon 2 ---------->
        <--SIGNAL PEPTIDE-->          PROPIECE                       CRYPTDIN
        1                                               58                              93
Cryp01  MKTLVLLSAL VLLAFQVQAD PIQNTDEETK TEEQPGEDDQ AVSVSFGDPE GTSLQEES LRDLVCYCRS RGCKGRERMN GTCRKGHLLY TLCCR
Cryp02  MKTLILLSAL VLLAFQVQAD PIQNTDEETK TEKQPGEEDQ AVSVSFGDPE GSSLQEES LRDLVCYCRT RGCKRRERMN GTCRKGHLMY TLCCR
Cryp03  MKTLVLLSAL VLLAFQVQAD PIQNTDEETK TEEQPGEDDQ AVSVSFGDPE GSSLQEES LRDLVCYCRK RGCKGRERMN GTCRKGHLMY TLCCR
Cryp04  ...LVLLSAL VLLAFQVQAD PIQNTDEETK TEEQPGEEDQ AVSISFGGQE GSALHEKS LRGLLCYCRK GHCKRGERVR GTC**G*IRF LYCCPRR
Cryp05  MKTFVLLSAL VLLAFQVQAD PIHKTDEETN TEEQPGEEDQ AVSISFGGQE GSALHEE. LSKKLICYRI RGCKRRERVF GTCRNLFLTF VFCCS
Cryp06  MKTLVLLSAL VLLAFQVQAD PIQNTDEETK TEEQPGEEDQ AVSVSFGDPE GSALHEE. LSKKLICYRI RGCKRRERVF GTCRNLFLTF VFCCS
Cryp07  MKTLILLSAL VLLAFQVQAD PIQNTDEETK TEEQPGEEDQ AVSVSFGDPE GTSLQEES LRDLVCYCRA RGCKGRERMN GTCRKGHLLY MLCCR
Cryp08  MKTLVLLSAL VLLAFQVQAD PIQNTDEETK TEEQPGEDDQ AVSVSFGDPE GSSLQEES LRDLVCYCRT RGCKRREHMN GTCRKGHLMY TLCCR
Cryp09  ..LAFQVQAD PIQNTDEETK TEEQPGEEDQ AVSVSFGDPE GSSLQEES LRDLVCYCRK RGCKRREHMN GTCRKGHLLY TLCCR
Cryp10  .KTLVLLSAL VLLAFQVQAD PIQNTDEETK TEEQPGEEDQ AVSVSFGDPE GSSLQEES LRDLVCYCRK RGCKGRERMN GTCRKGHLLY TLCCR
Cryp11  ......AL VLLAFQVQAD PIQNTDEETK TEEQPGEEDQ AVSVSFGDPE GTSLQEES LRDLVCYCRS RGCKGRERMN GTCRKGHLMY MLCCR
Cryp12  MKTLILLSAL VLLAFQVQAD PIQNTDEETK TEEQPGEEDQ AVSVSFGDPE GTSLQEES LRDLVCYCRA RGCKGRERMN GTCRKGHLMY TLCCR
Cryp13  MKTLVLLSAL VLLAFQVQAD PIQNTDEETK TEEQPGEEDQ AVSVSFGDPE GSSLQEES LRDLVCYCRK RGCKRREHMN GTCRKGHLMY TLCCR
Cryp14  ......AL VLLAFQVQAD PIQNTDEETK TEEQPGEEDQ AVSVSFGDPE GSSLQEES LRDLVCYCRT RGCKRRERMN GTCRKGHLMH TLCCR
Cryp15  MKTLVLLSAL VLLAFQVQAD PIQNTDEETK TEEQPGEDDQ AVSVSFGDPE GSSLQEES LRDLVCYCRS RGCKRREHIN GTCRKGHLLY MLCCR
Cryp16  MKTLILLSAL VLLAFQVQAD PIQNTDEETK TEEQPGEEDQ AVSVSFGDPE GTSLQEES LRDLVCYCRS RGCKGRERMN GTCRKGHLMY TLCCR
Cryp17  .LLAFQVQAD PIQNTDEETK TEEQPGEEDQ AVSVSFGDPE GTSLQEES LRDLVCYCRK RGCKRREHMN GTCRKGHLLY TLCCR
```

FIG. 9B

| | MKTLVLLSAL | VLLAFQVQAD | PIQNTDEETK | TEEQPGEDDQ | AVSVSFGDPE | GTSLQEES | LRDLVCYCRS | RGCKGRERMN | GTCRKGHLLY | TLCCR |
|---|---|---|---|---|---|---|---|---|---|---|
| Cryp01 | .......... | .......... | .......... | .......... | .......... | ........ | .......... | .......... | .......... | ..... |
| Cryp02 | ....I..... | .......... | .......... | .K....E... | .......... | ...S.... | .......... | T.......R. | .......... | ...M. |
| Cryp03 | .......... | .......... | .......... | .......... | .......... | ...S.... | .......... | ........R. | .......... | ...M. |
| Cryp04 | .......... | .......... | .......... | .......... | ....I..GQ. | SA.H.K.. | .G.L....K  | GH.RG..VR  | **.*IRF LY..PRR | |
| Cryp05 | ....F..... | .......... | ...HK....N | .......... | ....I..GQ. | SA.H.... | LSKK.I...I | .....R..VF | ...NLF TF VF..S | |
| Cryp06 | .......... | .......... | .......... | .......... | .......... | ........ | ........A. | .......... | .......... | ...M. |
| Cryp07 | ....I..... | .......... | .......... | .......... | .......... | ...S.... | .........T | .....R..H. | .......... | ...M. |
| Cryp09 | .......... | .......... | .......... | ........E. | .......... | ...S.... | .........K | .....R..H. | .......... | ..... |
| Cryp08 | .......... | .......... | .......... | ........E. | .......... | ...S.... | .........K | .....R..H. | .......... | ...M. |
| Cryp10 | .......... | .......... | .......... | ........E. | .......... | ...S.... | .........K | .....R..H. | .......... | ...M. |
| Cryp11 | .......... | .......... | .......... | .......... | .......... | ........ | .........A | .......... | .......... | ..... |
| Cryp12 | ....I..... | .......... | .......... | ........E. | .......... | ........ | .........K | .....R..H. | .......... | ...M. |
| Cryp13 | .......... | .......... | .......... | ........E. | .......... | ........ | .........K | .....R..H. | ........R..M. | |
| Cryp14 | .......... | .......... | .......... | ........E. | .......... | ...S.... | .........T | .....R.... | .......... | ..... |
| Cryp15 | .......... | .......... | .......... | ........E. | .......... | ...S.... | .........K | .....R..H. | .......MH | ..... |
| Cryp16 | ....I..... | .......... | .......... | .......... | .......... | ........ | .......... | .......... | .......... | ...M. |
| Cryp17 | .......... | .......... | .......... | ........E. | .......... | ........ | .........K | .....R..HI | .......... | ..... |

| Cryptdin-1 | AspProIleGlnAsnThrAspGluGluThrLysThrGluGluGlnProGlyGluAspAspGlnAlaValSerValSerPheGlyAspProGluGlyThr |
|---|---|
| Codon: | 20　　　　　　　　　　　30　　　　　　　　　　　40　　　　　　　　　　　50 |
| Cryp01 Base | CTGATCCTATCCAAAACACAGATGAAGAGACTAAAACTGAAGAGCAGCCAGGGGAAGACGACCAGGCCGTATCTGTCTCCTTTGGAGACCCAGAAGGCAC |
| | 60　　　　　70　　　　　80　　　　　90　　　　　100　　　　110　　　　120　　　　130　　　　140　　　　150 |
| Cryp01 | ................................................................................................A. |
| Cryp02 | .........T..............................G..................C..A............................... T. |
| Cryp03 | ........................................C............................................. ...........T. |
| Cryp04 | .........T..............................G..................................A..C...........G.A.....GT. |
| Cryp05 | .........C.A.........T.........A.........G..................................A..............G.A.....GT. |
| Cryp06 | .........T..............................G..................................................A. |
| Cryp07 | ........................................C...........................................T. |
| Cryp08 | ........................................C...........................................T. |
| Cryp09 | ........................................G...........................................T. |
| Cryp10 | ........................................C...........................................T. |
| Cryp11 | ........................................G..................................................A. |
| Cryp12 | ........................................G..................................................A. |
| Cryp13 | ........................................G........A..........C..A............C...............T. |
| Cryp14 | ........................................C...........................................T. |
| Cryp15 | ........................................C...........................................T. |
| Cryp16 | ........................................G........A..........C..A............C...............A. |
| Cryp17 | .........T..............................G........A..........C..A............C...............A. |
| Consensus | CTGATCCTATCCAAAACACAGATGAAGAGACTAAAACTGAGGGAGCAGCCAGGGGAAGA-GACCAGGCTGTGTCTGTCTCTTTTGGAGACCCAGAAGGC-C |

FIG. 10(c)

| Cryptdin-1 | SerLeuGlnGluSerLeuArgArgAspLeuValCysTyrCysArgSerArgGlyCysLysGlyArgGluArgMetAsnGlyThrCysArgLysGlyHis |
|---|---|
| Codon: | 60             70             80 |
| Cryp01 Base | TTCTCTTCAAGAGGAATCGTTGAGAGATCTGGTATGCTATTGTAGAGAGGCTGCAAAGGAAGAGAACGCATGAATGGGACCTGCAGAAAGGGTCAT |
|  | 160   170   180   190   200   210   220   230   240   250 |

```
Cryp01   ..............................................TC..........G...........G.........................
Cryp02   ..............................................TC..........A.........G...........................
Cryp03   ..............................................AA..........A.........G...........................
Cryp04   .G......T.AA....T.........G.T.T.............AA.G..CA.....A..G...........A.........T..TG...TAC.ATT.
Cryp05   .G......T.....T.CA.A.A.G...A.................AT..........A.........GAG.TCG........G.G.TTT........
Cryp06   ............A.....T..........................GC..........G.........A.............................
Cryp07   .............................................AC..........A.........A.............................
Cryp08   .............................................AA..........A.........A.............................
Cryp09   .............................................AA..........A.........A.........A..................
Cryp10   .............................................AA..........G.........G.............................
Cryp11   .............................................TC..........G.........G...........A.................
Cryp12   .......C....A.................................GC..........G.........G.............................
Cryp13   .............................................AA..........A.........A.....................G.......
Cryp14   .............................................AC..........A.........A.............................
Cryp15   .............................................AA..........A.........A.........A...A...............
Cryp16   .............................................TC..........G.........G.............................
Cryp17   ........T....................................AA..........A.........A.............................
```

Consensus TTCTCTTCAAGAGGAATCGTTGAGAGATCTGGTATGCTATTGTAGA--AAGAGGCTGCAAA-GAAGAGAAC-CATGAATGGGACCTGCAGAAAGGGTCAT

FIG. 10(d)

```
Cryptdin-1  LeuLeuTyrThrLeuCysCysArgEnd
Codon:              90            ***
Cryp01      TTATTGTACACGCTCTGCTGTCGCTGAaacatgagaccacagagagacaagacgaacatgagtactgaggccactgatgctggtgcctgatgaccacttcg
Base        260       270       280       290       300       310       320       330       340       350
Cryp01      ....T.........C.................................A......G.........CG.A............................C..G
Cryp02      ....A.........C.................................A......G.........TG.C............................
Cryp03      ....A........CA.................................A......G.........CG.A............................
Cryp04      .....GTAC.G.TGC.C.C..C.CT.AAC.TGCA.AT...AAAGATATGAC.ACCATTGTCTCTG.GGCC.CTG.TGCCG.GGCC..ATGACCACTTCTCAA.
Cryp05      .....ACT.T.GTAT.......CA.....T..C....TGA..A..ATATGACAACCATC.GC.CTGAG.C.CTGAAG.C.ACTGATGCTG..GT.TGATGAT.AC..CGC
Cryp06      ....T...........................................T......A.........CG.C............................
Cryp07      ....A...........................................T......A.........CG.C............................
Cryp08      ....A.........C.................................A......G.........CA.G............................
Cryp09      ....T.........T.................................A......G.........TG.A............................
Cryp10      ....T.........C.................................A......G.........CG.A............................
Cryp11      ....T.........T.................................T......A.........CG.C............................
Cryp12      ....A.........C.................................A......A.........CG.C............................
Cryp13      ....A........CA.................................A......G.........CG.A............................C..G
Cryp14      ....A..C......C.................................A......G.........CA.G............................
Cryp15      ....T.........T.................................A......G.........TG.C............................CG*
Cryp16      ....A.........C.................................T......A.........CG.C............................
Cryp17      ....T.........T........T.........................A......G.........T.C............................C..G
Consensus   TTA-TGTACA-GCTCTGCTGTCGCTGAacatgagaccc-cagag-acaaga--a-catgagtactgaggccactgatgctggtgcctgatgaccacttct
```

FIG. 10(e)

```
Cryp01    caataaattgttcgcaatatgc(A)n
Base           360       370
Cryp01    ......................
Cryp02    ..........C.T.........
Cryp03    ......................
Cryp04    A...-GT...CAATATGC.
Cryp05    A.TA..T.GT.CGCA.TATG.
Cryp06    ....C.................
Cryp07    ......................
Cryp08    ......................
Cryp09    ......................
Cryp10    ......................
Cryp11    ......C...............
Cryp12    ......................
Cryp13    ......................
Cryp14    ................A.....
Cryp15    ......................
Cryp16    ......................
Cryp17    ..........C.T.........
Consensus caataaattgttcgcaatatgc
```

FIG. 11(a)

```
                        130            140           150            160           170
CODON          43 44 45 46 47 48 49 50 51 52 53 54 55 56 57 58
               TCTGTCTCTCTTTGGAGACCIAGAAGGCICTTCTCTTCAAGAIGAATgtgagtaXtggtgXccagtgtgatggatgctt..........ttttgtgtctcc
Cryp1          .........C.........C....A........G......c....t....a......nnnn..nnnn..........
Cryp2          .........C.........G....G........A......c....c...........nnnn..nnnn..........
Cryp3          .........T.........C....T........G......c....c...........nnnn..nnnn..........
Cryp5          .........A....C....G.A....GT..G......T.A..g....t..g.......nnnn..nnnn..........
Cryp6          ..............T....C....A........G......c....t....acg.....nnnn..nnnn..........
Crypi          ..............C....C....T........G......c....c...........nnnn..nnnn..........

180          190          200          210          220          230          240          250          260          270
CODON          59 60 61 62 63 64 65 66 67 68 69 70 71 72 73 74 75 76 77 78 79 80 81 82 83 84 85 86 87 88 89 90
               agCGTTGAGAGATCTGITATGCTATTGTAGAIIAAGAGGCTGCAAAIGAAGAGAACGCITGAATGGACCTGCAGAAAGGGTCATTTAITGTACAIICTC
Cryp1          ..........G...............TC..........G......A.................A.............T......CG...
Cryp2          ..........G...............AC..........T.A.....................................A......CG...
Cryp3          ..........G...............AA..........A.......................................A......CA...
Cryp5          ..T.CA.A.A.G....A.........AT..........A......G.TTT..........TCT.TT....ACT.T.GTAT..
Cryp6          ..A.............G.........GC..........G.A.....................T......TG...
Crypi          ................A..TGA...AC..........A.......C................................T......TG...

280
CODON          91 92 93
               TGCTGXXGCTGAACATGGAGA
Cryp1          .....TC...............
Cryp2          .....CC...............
Cryp3          .....TC...............
Cryp5          .....TA....T...C......
Cryp6          .....TC...............
Crypi          .....CT...............
```

RAT CRYPTIN 1 cDNA SEQUENCE

```
10         20         30         40         50
1234567890 1234567890 1234567890 1234567890 1234567890
ACACTGGTCT CCAGCTCACC AATCCTCCAG GTGACTTCCA GCCATGAAGA    50
CTCTTGTCCT CCTCTCTGCC CTTGTCCTGC TGGCATTCCA GGTCCAGGCT   100
GATCCCATTC AAGAGGCAGA AGAAGAGACT AAAACTGAGG AGCAGCCAGC   150
AGATGAGGAC CAGGATGTGT CTGTCTCCTT TGAAGGCCCA GAACCCTCTG   200
CTCTTCAAAA TTTAGAGATA GGATGGCCAT TAAAGCAGTG CCATTGCCGA   250
AAGTTCTGCA GACCTTATGA AAAGGCCGAG GGGTCCTGTC GTCCAGGTCT   300
ATTTATAAAA CGCAAAATCT GCTGCATACA ACAATGGACA CCAGGGAGGA   350
CATAACCACG TGAACTGGGA CCTCACAATC TGTCATTCTT GGGCTTCAAC   400
TCGACTGCTT TTCCTTCTCC AATAAACCCC TTGCAGACAA AAAAA        445
```

FIG. 14B

RAT CRYPTIN 2 cDNA SEQUENCE

```
10         20         30         40         50
1234567890 1234567890 1234567890 1234567890 1234567890
ACACTGGTCT CCAGCTCACC AATCCTCCAG GTGACTTCCA GCCATGAAGA    50
CTCTTGTCCT CCTCTCTGCC CTTGTCCTGG TGGCCTACCA GGTCCAGGCT   100
GATCCCATTC AAGGGGCAGA AGAAGAGACT AAAACTGAAG AGCAACCATC   150
AGATGAGGAC CAGGATGTGT CTGTCTCCTT TGAAGGCCCA GAAGCCTCTG   200
CTCTTCAAGA TTTTGAGATA GGAAGGCCAG TGAGGAGGTG CCGTTGCAGA   250
GCAAACTGCG GACCTAAAGA ATATGCCACT GCGTTCTGTG CTCAAGGTCC   300
ATTTAAACAG TTCAAATTCT GCTGCACATG AACATGGATC CCAAGTCTGA   350
GATAACCACG TGCTCTGGGA CCTCACAATC TGTCATTATT GTGCTTGACC   400
TCAACTGCTT TTCCTTCTCC AATAAACTCC TGGCAGACAA AAAAA        445
```

FIG. 14C

RAT CRYPTIN 3 cDNA SEQUENCE

```
10         20         30         40         50
1234567890 1234567890 1234567890 1234567890 1234567890
ACACTGGTCT CCAGCTCACC AATCCTCCAG GTGACTTCCA GCCATGAAGA    50
CTCTTGTCCT CCTCTCTGCC CTTGTCCTGC TGGCATTCCA GATCCAGGCT   100
GATCCCATTC AAGAGGCAGA AGAAGAGACT AAAACTGAGG AGCAGCCAGC   150
AGATGAGGAC CAGGATGTGT CTGTCTCCTT TGAAGGCCCA GAACCCTCTG   200
CTCTTCAAAA TTTAGAGATC AGATGGCCAT GGAAGAGGTG CCATTGCAGA   250
AGTTTCTGCA GACCTTATGA AAATCGGACT TCGTTCTGTG CTCAAGGTCT   300
ATTTAAACAA CACAAATTCT GCTGCCTAGA AACATGGCCC CCAAGGATGA   350
AATAACCACG TGCTCTGGGA CCTCACAATC TGTCATCATT GTGCTTGGCC   400
TCAACTTCTT TTCCTTCTCC AATAAACTCC TTGCAGACAA AAAAA        445
```

FIG. 15A(1)

RAT CRYPTIN 1 GENOMIC SEQUENCE

|          10 |          20 |          30 |          40 |          50 |      |
|-------------|-------------|-------------|-------------|-------------|------|
| 1234567890  | 1234567890  | 1234567890  | 1234567890  | 1234567890  |      |
| CCTGAGACCA  | ACTCTGTGAT  | AATCAGAAAA  | GTCAATAATG  | TGTCTGAAAT  | 50   |
| GTAAGGTGTG  | CTTCTTGACT  | GATAGTTCTA  | AGCCTACAGA  | GAGATTCATG  | 100  |
| TGGTCATATC  | CCATTTAACA  | ATGATATATA  | TGTTAAATAT  | ATAAAGATAT  | 150  |
| ATGTATGTTC  | AGTATGTATG  | TTCAATATGT  | ATGTAAATAA  | TATTCTTGCT  | 200  |
| GCTTCACTAG  | CTTTTACACA  | GAGCTGTAAG  | TAAAAACATT  | GTAGCCAATG  | 250  |
| AATAGTATTT  | ATTAACATGT  | AAATAGGAGC  | TGGCACCTGT  | GACAGTGGGA  | 300  |
| CTCCATACAC  | TGACTGTAAA  | CAACAGGATG  | CTCTGGACCT  | TTTGCTGTGT  | 350  |
| GTGTGGTGAG  | AGACATGGGA  | TAAACACAGA  | CTGAAGAGTG  | TTCCTGAATG  | 400  |
| ACATGGCGGC  | ACTTCTCGAG  | ACCGGGTAGC  | AGCTTCTGAG  | CCTCTCTACA  | 450  |
| TTGTGGATGT  | CCTTTCCTGT  | AGGTCAGGTC  | TCATTGTCTA  | AAAGTAAAAG  | 500  |
| CATTGCAGCA  | TCTCAGACCT  | GGGAAACACC  | CCATGGCTTG  | AGGGTCCTGA  | 550  |
| GCATGAAGAG  | CCACCTGGAG  | CTCACTCTTG  | GCAGATGTGT  | TCCATGACTT  | 600  |
| TGGCTTCTTC  | AGAACAACCC  | ACTACAGCTT  | CACTCTGACA  | AATCCTAGAA  | 650  |
| ACTTGAACTC  | AATTCACTAG  | AGGGCACCAT  | AAAGCCATCA  | TACCTTATAA  | 700  |
| TGGCCCCAAA  | GGAGGTGATT  | CACAAAGTTT  | GCCTTGATGA  | GGACAATTGC  | 750  |
| TAATACACAA  | AAACTTGCAA  | AAAAAAATTG  | AGTGTCCAGT  | CCACCTGGTC  | 800  |
| AAGGACTGGT  | CCCGGATCCA  | CAGTTTCTGA  | GAATAGCAGG  | CTCTAACTTG  | 850  |
| AAAACACAAA  | AATTGTTTGT  | TCTATGAGCT  | CATTAAATTA  | GGCAGTGTTC  | 900  |
| AGCTATTTTC  | TTTCCTGACC  | ACTGAGAGGT  | AAATACTCAA  | GCAGATGGGA  | 950  |
| AACAGGGGAG  | GACAGTAAAG  | CCTGTTCATC  | ATTATCAGTG  | GGAGTGTGCA  | 1000 |
| TGAGGGGAGG  | GGTGTCAGTG  | AACACACAGA  | GCATCAGGAA  | GGAAGCCTTG  | 1050 |
| AGGACAGAGG  | AACATCAAAG  | GGATCCTGAG  | GACAACAGCT  | GGGAGCAGTT  | 1100 |
| GCCATCAATG  | AGTGCCTTCT  | CTAAGTATGG  | GGCATGTTCT  | TTGCCCTATA  | 1150 |
| AATGCAGGCT  | GGCTTCTCTC  | TCCACACACT  | GGTCTCCAGC  | TCACCAATCC  | 1200 |
| TCCAGGTGAC  | TTCCAGCCAT  | GAAGACTCTT  | GTCCTCCTCT  | CTGCCCTTGT  | 1250 |
| CCTGCTGGCA  | TTCCAGGTCC  | AGGCTGATCC  | CATTCAAGAG  | GCAGAAGAAG  | 1300 |
| AGACTAAAAC  | TGAGGAGCAG  | CCAGCAGATG  | AGGACCAGGA  | TGTGTCTGTC  | 1350 |
| TCCTTTGAAG  | GCCCAGAACC  | CTCTGCTCTT  | CAAAATTTAG  | GTGCGTGCTT  | 1400 |
| GTGCACAGAA  | TGATGGAGGC  | TTGGAGTCTC  | CTGATGGAGG  | GTTGTAGATT  | 1450 |
| AGCCCTGGAG  | TCCTGTCAAG  | GACAGTCTGG  | TTCAGGTAGC  | TGTCTACTGA  | 1500 |
| TCCTTTCAGA  | ACTTCCCTGT  | CTTATTCATA  | GAAATAACAG  | TGAGAGACAA  | 1550 |
| GCCATTGGGC  | TTGACTTTTT  | CCTTTTAAGA  | TTTCGGTCTA  | ACAATTTATC  | 1600 |
| TGTGAAAAAC  | CTTTAAAATA  | TAAAACATAT  | TGATTAGTTC  | TTTAAACCTG  | 1650 |
| AGTGATAATT  | TTCTTACAGG  | AAGAAATATC  | CGTTTTACCC  | TAAAAATTAG  | 1700 |
| ATTGGTACCC  | AAATGCCAGT  | GTATGAAGGT  | GTTGGGTCAA  | GAAAACACAA  | 1750 |
| AAAAACTGTT  | AGAATATGGT  | GTAGATGAAA  | ATTCCTATAT  | GTGATTAACA  | 1800 |
| CTTGTTAAAC  | ATCTTATCTC  | CATGTGTTTG  | GGGTTGATCA  | CTGTGCTGGC  | 1850 |
| TGTGATGTCA  | CCCACACAGC  | AAACCTACTC  | TCTACCATGC  | ACAGGACATC  | 1900 |

FIG. 15A(2)

RAT CRYPTIN 1 GENOMIC SEQUENCE

```
        10         20         30         40         50
1234567890 1234567890 1234567890 1234567890 1234567890
TTCATGGGGT AGTTCACTGT TACACACTAC TGGCCTCCTT ACTTCATGCC  1950
TGATGCTTTC TTGTTTCCTC AGAGATAGGA TGGCCATTAA AGCAGTGCCA  2000
TTGCCGAAAG TTCTGCAGAC CTTATGAAAA GGCCGAGGGG TCCTGTCGTC  2050
CAGGTCTATT TATAAAACGC AAAATCTGCT GCATACAACA ATGGACACCA  2100
GGGAGGACAT AACCACGTGA ACTGGGACCT CACAATCTGT CATTCTTGGG  2150
CTTCAACTCG ACTGCTTTTC CTTCTCCAAT AAACCCCTTG CAGACAAATA  2200
ACCTGTTTAT GTTTTTTTGA TGCTTTCTAT GTGGCGTAGA CAGGACTCTC  2250
CTGAGCCATG TAGCAAAATC TTCAGTGAAT CCTTTGTAAA AGAAGTCTTG  2300
GTCACATTTC AGCAGTCATA TCAAGGATGA GCAGGAGGTT AGATCCAAAG  2350
AGACAAGATG GTCTGCGCCA GCTGCTTCTG TGTCTATCAA GTCTTCTGTC  2400
CTTTAGATTA GAGTCACCCT CAAAAATTAG TTCCAGATTT TCATGTTCTA  2450
TTTTTTC                                                 2457
```

FIG. 15B(1)

RAT CRYPTIN 2 GENOMIC SEQUENCE

| 10 | 20 | 30 | 40 | 50 | |
|---|---|---|---|---|---|
| 1234567890 | 1234567890 | 1234567890 | 1234567890 | 1234567890 | |
| TATTACGAAT | TCGAGCTCGG | TACCGGTATA | TGAAGAGCGA | CCACTGCCAG | 50 |
| GACGAAAGTG | CAATGCGGCA | TACCTCAGTG | GCGTGGAGTG | CAGGTATACA | 100 |
| GATTAATCCG | GCAGCGTCCG | TCGTTGTTGA | TATTGCTTAT | GAAGGCTCCG | 150 |
| GCAGTGGCGA | CTGGCGTACT | GACGGATTCA | TCGTTGGGGT | CGGTTATAAA | 200 |
| TTCTGATTAG | CCAGGTAACA | CAGTGTTATG | ACAGCCCGCC | GGAACCGGTG | 250 |
| GGCTTTTTTG | TGGGGTGAAT | ATGGCAGTAA | AGATTTCAGG | AGTCCTGAAA | 300 |
| GACGGCACAG | GAAAACCGGT | ACAGAACTGC | ACCATTCAGC | TGAAAGCCAG | 350 |
| ACGTAACAGC | ACCACGGTGG | TGGTGAACAC | GGTGGGCTCA | GAGAATCCGG | 400 |
| ATGAAGCCTG | CTTTTTTATA | CTAAGTTGGC | ATTATAAAAA | AGCATTGCTT | 450 |
| ATCAATTTGT | TGCAACGAAC | AGGTCACTAT | CAGTCAAAAT | AAAATCATTA | 500 |
| TTTGATTTCA | ATTTTGTCCC | ACTCCCTGCC | TCTGTCATCA | CGATACTGTG | 550 |
| ATGCCATGGT | GTCCGACTTA | TGCCCGAGAA | GATGTTGAGC | AAACTTATCG | 600 |
| CTTATCTGCT | TCTCATAGAG | TCTTGCAGAC | AAACTGCGCA | ACTCGTGAAA | 650 |
| GGTAGGCGGA | TCTGGGTCGA | CTCTAGGCCT | CACTGGCCTA | ATACGACTCA | 700 |
| CTATAGGGAG | CTCGAGGATC | ATTGCTAATA | CCATGAAACT | TGACCACCTG | 750 |
| GTCAAGGACT | GGTCCAGGGT | CCACAGTTTC | TGAGAAGAGC | AGGCTCCAAC | 800 |
| TTCTAACCAC | AAAAACTATT | TTTTCCATGC | GCTCCTTAAA | TTAGGCAGCG | 850 |
| CCCAGCTATT | TTCTTTCCTG | ACCACTGAGA | GGTAAATACT | CAAGCAGATG | 900 |
| GGAAACAGGG | GAAGATAGCA | AGGCCTCTTC | ATCATTATCA | CTGGGTGTGT | 950 |
| GCGTGAGGGG | AGGGGTGTCA | TTGCATACAC | AGGGCAACAT | CAGGATGGAA | 1000 |
| GCCTTGAGGA | CAGAGGAACA | TCAAAGGGAT | CCTGAGGACA | ACAGCTGGGA | 1050 |
| GCAGTTGCCA | TCAGTGAGTG | CCTTCTCTAA | GTGTGGGGCC | TTTCTCTGCC | 1100 |
| ACATAAATGC | AGGCTGCCTC | CTCTCTCCAC | ACACTGGTCT | CCAGCTCACC | 1150 |
| AATCCTCCAG | GTGACTTCCA | GCCATGAAGA | CTCTTGTCCT | CCTCTCTGCC | 1200 |
| CTTGTCCTGG | TGGCCTACCA | GGTCCAGGCT | GATCCCATTC | AAGGGGCAGA | 1250 |
| AGAAGAGACT | AAAACTGAAG | AGCAACCATC | AGATGAGGAC | CAGGATGTGT | 1300 |
| CTGTCTCCTT | TGAAGGCCCA | GAAGCCTCTG | CTCTTCAAGA | TTTTGGTGAG | 1350 |
| TGCTTATGCA | CAGAATGATG | GAGGCTTGGA | GTCTCCTGAT | GGAGGGTTGT | 1400 |
| AGATTAGACC | TGGAATCCTG | TCAAGAACTG | TCTGGTTCAG | GTAGCTGTCT | 1450 |
| CTTGGTCCCT | TTACATTCCT | TGTCTTCTTC | ATAGAAGTAA | CGGAGAGAGA | 1500 |
| TTAACCATTG | GGCTTGACTT | TTTTCCTTTT | AAAATTTTTG | ATCTAACAAT | 1550 |
| TTATCTGTGG | AAAACCTTTA | AAATATAAAA | CATATTGATT | AGTTCTTTTA | 1600 |
| GACCTGATTG | ATAATTTTGT | TATAAGAAGA | AATATTCGTT | CTACTTTAAA | 1650 |
| AATTAGATTT | GGGACCCAAA | TGCCAGTGTA | TGAAGCTGTT | GGGTAAGGAA | 1700 |
| AAACCAAAAA | TGGTGATAGA | ATGTTGTGTA | GATGACAATT | CCTTTATGCG | 1750 |
| ATTAACACTT | TTTAAAATGT | CTTATCTCCA | TGTGTTTGGG | GTTGATCATG | 1800 |

FIG. 15B(2)

RAT CRYPTIN 2 GENOMIC SEQUENCE

```
        10         20         30         40         50
1234567890 1234567890 1234567890 1234567890 1234567890
GTGCTGACTG TGATGTCACC CACAGAGCAA ACCTACTCTC TACCATGCAC  1850
AGGACATCTT CATAGGGTAG TTCACTGTCA CACACTGCTG GCCTCGTTAC  1900
TTCATGCCTG ATGCTTTCTT GTTTCCTCAG AGATAGGAAG GCCAGTGAGG  1950
AGGTGCCGTT GCAGAGCAAA CTGCGGACCT AAAGAATATG CCACTGCGTT  2000
CTGTGCTCAA GGTCCATTTA AACAGTTCAA ATTCTGCTGC ACATGAACAT  2050
GGATCCCAAG TCTGAGATAA CCACGTGCTC TGGGACCTCA CAATCTGTCA  2100
TTATTGTGCT TGACCTCAAC TGCTTTTCCT TCTCCAATAA ACTCCTGGCA  2150
GACAAATAAT CGGTATATGT TTATTTGATG CTTTCTATTT GGCTTAGACA  2200
GAACTCTCCT GAGCCATGTA GCTGAATCTT CAGTGAATCC TTTGTAAAGG  2250
TCACATTTCA GCAGTCATAT CAAGGATGAG CAGGAGGTTA GATACAAAGA  2300
GACAAGATGG TCTGCGCCAG CTGCTTCTTT GTCTATCAAG TCTGCTTTCC  2350
TTTAGATTAG AGTCACCATC AAAAATTATT CCCACATTTT CATGTTCTAT  2400
ATTTTTTT                                                 2408
```

FIG. 15C(1)

RAT CRYPTIN 3 GENOMIC SEQUENCE

| 10 | 20 | 30 | 40 | 50 | |
|---|---|---|---|---|---|
| 1234567890 | 1234567890 | 1234567890 | 1234567890 | 1234567890 | |
| CCTGAGACCA | ACTCTGTGAT | AATCAGAAAA | GACAATTATG | TGTCTTAAAT | 50 |
| GTAAGGTTTG | CTTCTTGACT | GATAGATCTA | ACCCTACAGA | GAGATTCAAG | 100 |
| TGGTCTTGTC | CCATTGAACA | ATAGTATATA | TGTTTTATAT | ATATATATAT | 150 |
| ATATATGTAT | ATGTATATAT | ATATGTGTGT | GTGTGTGTGT | GTGTGTCTGT | 200 |
| GTCTGTGTGT | CTGTGTGTCT | GTGTGTCTGT | GTGTCTGTGT | GTGTATGTGT | 250 |
| GTGTATGTGT | ACATATGTTC | AATATGTCTG | TAAAATAGTA | TTCTTGTAGC | 300 |
| TTCACTTACT | TTTGCACAGA | GCTGTAAATA | AGAACATTGT | AGCCAATGAA | 350 |
| TAGTATTTAT | TAACATGTAA | ATAGGAGCTG | GCACCTCTGA | CAGTGGGACT | 400 |
| CCATACAGTG | ACTGTAAACA | ACAGGATGCT | CTAGACCTTT | TGCTGTGTGT | 450 |
| GTGGTGAGAG | ACATGGGATA | AACACAGACT | GAAGTGTATG | ACATGGCGGC | 500 |
| ACTTCTCGAG | ACCGGGTAGC | AGCTTCTGAG | CCTCTCTACA | TTGTGGATGT | 550 |
| CCTTTCCTGT | AGGTCAGGTC | TCATTGTCTA | AAAGTAAAAG | CATTGCAGCA | 600 |
| TCTCAGACCT | GGGAAACACC | CCATGGCTTG | AGGGTCCCGC | AGGTGAAGAG | 650 |
| CCACCTGGAG | CTCACTCTTG | GCAGATGTGT | TCCATGACTT | GGCTTCTTC | 700 |
| AGAACCACCC | ACTACAGCTT | CACTCTGACA | AATCTTAGAA | ACTTGAACTC | 750 |
| AATTCACTGG | AGGGCACAAT | AAAGCCATCT | TACTTTCTCT | AAAATGGCCC | 800 |
| CAAAGGAGGG | GATTCACAAA | GTTTGCCTTG | ATGAGGACCA | TTGCTAATAC | 850 |
| CCCAAAACTT | GCAAAAAAAA | TTGAGTGTCC | AGTCAACCTG | GTCAAGGACT | 900 |
| GGTCCTGGAT | CCACAGTTTC | TGAGAAAAGA | AGGCTCCAAC | TTCAAAACAC | 950 |
| AAACCACTCC | TGTTCTATGC | GCTCATTAAA | TTAGGCAGTG | TTAAGCTATT | 1000 |
| TTCTTTCCTG | ACCACTGAGA | GGTAAATACT | CAAGCAGATG | GGAAACAGGG | 1050 |
| GAGGACAGCA | AAGCCTGTTC | ATCATTATCA | GTGGGAGTGT | GCGTGAGGGG | 1100 |
| AGGGGTGTCA | GTGAACACAC | AGAGCATCAG | GAAGGAAGCC | TTGAGGACAG | 1150 |
| AGGAACATCA | AAGGGATCCT | GAGGACAACA | GCTGGGAGCA | GTTGGCATCA | 1200 |
| GTGAGTGCCG | TCTCTAAGTG | TGGGGCCTTT | CTCTGCCACA | TAAATGCAGG | 1250 |
| CTGGCTCCTC | TCTCCACACA | CTGGTCTCCA | GCTCACCAAT | CCTCCAGGTG | 1300 |
| ACTTCCAGCC | ATGAAGACTC | TTGTCCTCCT | CTCTGCCCTT | GTCCTGCTGG | 1350 |
| CATTCCAGAT | CCAGGCTGAT | CCCATTCAAG | AGGCAGAAGA | AGAGACTAAA | 1400 |
| ACTGAGGAGC | AGCCAGCAGA | TGAGGACCAG | GATGTGTCTG | TCTCCTTTGA | 1450 |
| AGGCCCAGAA | CCCTCTGCTC | TTCAAAATTT | AGGTGCGTGC | TTGTGCACAG | 1500 |
| AATGATGGAG | GCTTGGAGTC | TCCTGATGGA | GGGTTGTAGA | TTAGCCCTGG | 1550 |
| AGTCCTGTCA | AGGACAGTCT | GGTTCAGGTA | GCTGTCTATT | GATCCTTTCA | 1600 |
| GAACTTCCCT | GTCTTATTCA | TAGAAATAAC | AGTGAGAGAC | AAGCCATTGG | 1650 |
| GCTTGACTTT | TTCCTTTTAA | GATTTTGGTC | TAACAATTTA | TCTGTGAAAA | 1700 |
| ACCTTTAAAA | TATAAAACAT | ATTGATTAGT | TCTTTTAAAC | CTGATTGATA | 1750 |
| ATTTTGTTAT | AGGAAGAAAT | AACTGTTCTA | CTTTAAAAAT | TAGATTTGGT | 1800 |
| ACCTAAATGC | CAGTGTATTA | AGGTGTTGGG | TCAGGAAAAC | ACAATAATGC | 1850 |
| TGATAGAATG | TGGTGTAGAT | GACAATTCCT | ATATGCGATT | AACACTTGTT | 1900 |

FIG. 15C(2)

RAT CRYPTIN 3 GENOMIC SEQUENCE

|  10        |  20        |  30        |  40        |  50        |      |
|------------|------------|------------|------------|------------|------|
| 1234567890 | 1234567890 | 1234567890 | 1234567890 | 1234567890 |      |
| AAATTGTCCT | ATCTCCATGT | GTTTGGGGTT | GATCATGGTG | CTGGCTGTGA | 1950 |
| TGTCACCCAC | ACAGCAAACC | TACTTTCTAC | CATGCACAGG | ACATCTTCAT | 2000 |
| AGGGTAGTTC | ACTGTCACAC | ACTGCTGGCC | TCCTTACTTC | ATGCCTGATG | 2050 |
| CTTTCTCGTT | TCCTCAGAGA | TCAGATGGCC | ATGGAAGAGG | TGCCATTGCA | 2100 |
| GAAGTTTCTG | CAGACCTTAT | GAAAATGCCA | CTTCGTTCTG | TGCTCAAGGT | 2150 |
| CTATTTAAAC | AACACAAATT | CTGCTGCCTA | GAAACATGGC | CCCCAAGGAT | 2200 |
| GAAATAACCA | CGTGCTCTGG | GACCTCACAA | TCTGTCATCA | TTGTGCTTGG | 2250 |
| CCTCAACTTC | TTTTCCTTCT | CCAATAAACT | CCTTGCAGAC | AAATAACCTG | 2300 |
| TTTATGTTTT | TTTGATGCTT | TCTATGTGGC | TTAGACAGGG | CTCTCCTGAG | 2350 |
| CCATGTAGCA | GAATCTTCAG | TGAATCCTTT | GTAAAAGAAG | TCTTGGTCAC | 2400 |
| ATTTCAACAG | TCATATCAAG | GATGAGCAGG | AGGTTAGATC | CAAAGAGACA | 2450 |
| AGATGCTCTG | CTCCAGCTGC | TTCTTGACTA | TCAAGTCTTC | TGTCCTTCAG | 2500 |
| ATTAGAGTCA | CCCTCAAAAA | TTAGTCCCAC | CTTTTCATGT | TCTATTTTTT | 2550 |
| T          |            |            |            |            | 2551 |

ANTIBIOTIC CRYPTDIN PEPTIDES AND METHODS OF THEIR USE

This application is a continuation of United States Ser. No. 09/015,968, filed Jan. 30, 1998, now U.S. Pat. No. 6,057,425, issued May 2, 2000; which is a continuation of U.S. Ser. No. 08/482,279, filed Jun. 7, 1995, now U.S. Pat. No. 5,840,498, issued Nov. 24, 1998; which is a continuation of U.S. Ser. No. 08/342,268, filed Nov. 18, 1994, now U.S. Pat. 5,844,072, issued Dec. 1, 1998; which is a continuation-in-part of U.S. Ser. No. 07/930,649, filed Aug. 14, 1992, now U.S. Pat. 5,422,424, issued Jun. 6, 1995; which is a continuation-in-part of U.S. Ser. No. 07/889,020, filed May 26, 1992, now abandoned, each of which is incorporated herein by reference.

This invention was made with government support under grant numbers AI22931, AI31696, DK08851, DK44632 and DK33506, awarded by National Institutes of Health. The Government has certain rights in the invention.

BACKGROUND OF THE INVENTION

FIELD OF THE INVENTION

This invention relates generally to antimicrobial peptides and more specifically to cryptdin peptides, nucleic acid molecules encoding cryptdins, and their uses.

BACKGROUND INFORMATION

Survival in a world teaming with microorganisms depends on a network of host defense mechanisms. Among these mechanisms are phagocytosis by cells are resident in tissues or that circulate in the blood system and ingest, kill and digest potentially harmful microbes. Although pathogenic microbes may vary considerably, phagocytes are able to destroy the vast majority by sequestering them in intracytoplasmic vacuoles and exposing them to a lethal mixture of organic and inorganic toxins.

Perhaps the most remarkable ultrastructural feature of phagocytes are their several thousand cytoplasmic granules, which are membrane-bound organelles typically about 0.3 μm in diameter. During phagocytosis, some of these granules fuse to phagocytic vesicles thus enabling the contents of the granule to enter the lumen of the vesicle. Early observers surmised correctly that the granules contained factors which were responsible for intraphagosomal killing in digestion of microbes. These granules contain a mixture of antimicrobial molecules including various peptides such as the so-called defensins.

Defensins are abundant antimicrobial peptide components of vertebrate neutrophil and macrophage granules. Members of the defensin family have been identified previously in human, rabbit, guinea pig and rat phaodyes,primarily those phagocytes termed phagocytic granulocytes. Defensins are cationic peptides that have molecular weights between about 3 and 4 kiloDaltons (kDa) and that exhibit broad-range antimicrobial activities against gram negative and gram positive bacteria, many fungi and some enveloped viruses. The peptides are characterized by eight invariant amino acids, including six invariant cysteine residues that constitute a unique disulfide motif. The three disulfide bonds stabilize a tertiary conformation consisting predominantly of β-sheet. The highly ordered structure and the absence of a helix make defensins unique among known antimicrobial peptides. It appears that defensins exert their antibacterial effect by permeabilizing the cytoplasmic membrane of the target microorganism by a Mechanism that may involve the formation of ion channels or transmembrane pores.

Until recently, defensins had been identified only in circulating or tissue phagocytes of myeloid origin. However, based on the presence of a particular mRNA, it has been surmised that similar peptides might be present in the epithelial cells of the small intestine. Such intestinal peptides may prevent access of microorganisms through the small intestine into the systemic circulation and, therefore, can be useful as a therapeutic or prophylactic agent. Thus, a need exists to identify peptides that have antimicrobial activity within the uiucosal epithelium or in the intestinal lumen. The present invention satisfies this need and provides additional benefits as well.

SUMMARY OF THE INVENTION

The present invention provides a substantially purified cryptdin peptide having a consensus amino acid sequence:

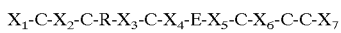

wherein $X^1$ is 3 to 9 amino acids; $X_2$ is 1 amino acid, preferably Y, H or R; $X_3$ io 2 or 3 amino acids $X_4$ is 3 amino acids; $X_5$ is 5 amino acids; $X_6$ is 6 to 10 amino acids; and $X_7$ is 0 to 9 amino acids.

The invention also provides a substantially purified mouse cryptdin having a consensus amino acid sequence:

wherein $X_1$ is 3 or 4 amino acids, preferably LRD, LSKK (SEQ ID No: 1) or LRG;

$X_2$ is 1 amino acid, preferably V, L or I;

$X_3$ is 3 amino acids, preferably KGH or *RG, where * is S, T, K, I or A;

$X_4$ is 2 amino acids, preferably GR, RR or RG;

$X_5$ is 3 amino acids, preferably RMN, RVR, RVF HMN or HIN;

$X_6$ is 6 to 9 amino acids, preferably GIRFLY (SEQ ID NO; 2) or RNLFLTFVF (SEQ ID NO: 3), RRGHLMYTL (SEQ ID NO: 4) or RKGHL*YT* (SEQ ID NO: 5), where * independently is L or M; and $X_7$ is 0 to 3 amino acids, preferably R, S or PRR.

For example, the invention provides various mouse, rat or human cryptdins having the sequence:
1) LRDLVCYCRSRGCKGRERMNGTCRKGHL-LYTLCCR (SEQ ID NO: 6);
2) LRDLVCYCRTRGCKRRERMNGT-CRKGHLMYTLCCR (SEQ ID NO: 7);
3) LRDLVCYCRKRGCKRRERMNGT-CRKGHLMYTLCCR (SEQ ID NO: 8);
4) GLLCYCRKGHCKRGERVRGTCGIRFLYCCPR (SEQ ID NO: 9);
5) LSKKLICYCRIRGCKRRERVFGTCRNLFLTFVFCC (SEQ ID NO: 10);
6) LKQCHCRKFCRPYEKAEGSCR-PGLFIKRKICCIQQWTPG (SEQ ID NO: 11);
7) GLLCYCRKGHCKRGERVRGTCGIRFLYCCPRR (SEQ ID NO: 12);
8) LSKKLICYCRIRGCKRRERVFGTCRNLFLTFVFCCS (SEQ ID NO: 13);
9) LRDLVCYCRARGCKGRERMNGTCRKGHL-LYMLCCR (SEQ ID NO: 14);
10) LKQCHCRKFCRPYEKAEGSCR-PGLFIKRKICCIQQWTPGRT (SEQ ID NO: 15);
11) IGRPVRRCRCRANCGPKEYATAFCAQG-PFKQFKFCCT (SEQ ID NO: 16);
12) IRWPWKRCHCRSFCRPYENATSF-CAQGLFKQHKFCCLDTWPPRMK (SEQ ID NO: 17);

13) TSGSQARATCYCRTGRCATRESLSGV-CEISGRLYRLCCR (SEQ ID NO: 18); and

14) AFTCHCRRSCYSTEYSYGTCTNMGINHRFCCL (SEQ ID NO: 19).

Cryptdins are typically characterized by being naturally found in the epithelial cells of the small intestine, being cationic, being about 30 to about 45 amino acids in length, having at least three and, preferably, three to nine, amino acids to the N-terminal of the first cysteine residue, exhibiting specific antimicrobial activity against intestinal pathogens and opportunistic pathogens and being relatively non-toxic to cells of the host organism. However, there may be diversity in these structural and functional characteristics. The invention also provides cryptdin analogs, which are devoid of one or more amino acids N-terminal to the first cysteine. In addition, the invention also provides nucleic acid molecules encoding cryptdin peptides. For example, the invention provides genomic DNA sequences and cDNA sequences encoding mouse and rat cryptdins.

The invention further provides a method for detecting an inflammatory pathology in a subject by determining the amount of cryptdin in a biological sample from the subject and comparing that amount to the amount present in a normal subject. such a method can be used to determine the presence of an inflammatory pathology such as inflammatory bowel disease, pancreatitis, malignancy, infection or ileitis.

The invention also provides a method for treating an inflammatory pathology in a subject by administering a cryptdin to the subject Such treatment is particularly advantageous in patients who are immunocompromised due, for example, to malnutrition, radiation burns, immunosuppressive infections, autoimmune disease, neonatality, bone marrow transplantation or chemotherapy. A cryptdin can be administered orally, by nasogastric intubation, by transabdominal catheter, intravenously or by aerosol inhalation. When administered orally, it is preferably in a delayed release formulation designed to permit release in the small intestine The cryptdin can be administered as a composition with a physiologically acceptable medium, and more than one cryptdin can be administered simultaneously or sequentially.

BRIEF DESCRIPTION OF THE DRAWINGS

FIG. 4.A. Lyophlized luminal lavage of small intestine from 12 mice and 20 µg protein was fractionated by P-60 gel filtration and electrophoresed on an acid-urea acrylamide gel (lane 2) along side a similarly prepared sample of bowel tissue (lane 1). The positions of cryptdins 1–5 (SEQ ID NOS: 6 to 10, respectively) are indicated.

FIG. 4.B. Partially purified luminal peptides (20 µg; as for FIG. 4.A., lane 2) were electrophoresed in a second acid-urea gel (lane 3) along with an identical sample previously treated with performic acid (lane 4). In lane 4, rapidly migrating, cyst(e)ine-containlng peptideg are absent due to the increased net negative charge resulting from the conversion of cyst (e) ines to cysteic acid residues.

FIGS. 6.A. and 6.B., 40X; FIGS. 6.C. and 6D., 250X; FIGS. 6.E. and 6.F., 640X.

FIG. 8 shows the amino acid sequences for rat cryptdins 1–3 (SEQ ID NOS: 15–17, respectively), human cryptdins 5 and 6 (SEQ ID NOS: 18 and 19; HD-5 and HD-6) and a consensus sequence (Def consensus). Also shown are the amino acids sequences for rat prepro-cryptdins 1–3 (SEQ ID NOS: 20–22) as deduced from cDNA or genomic DNA sequences as indicated.

FIGS. 9.A. and 9.B. show the amino acid sequences of mouse cryptdins 1–17 (SEQ ID NOS: 23 to 39, respectively) as determined from the cDNA sequences encoding the specific cryptdin.

FIG. 9.A. shows the entire amino acid sequence of the mouse cryptdins. The amino acid sequences of cryptdins 1–6 (SEQ ID NOS: 23 to 28) were determined by sequencing the purified peptides. The amino acid sequences of cryptdins 7–17(SEQ ID NOS: 29 to 39) were deduced from the cDNA sequences (see FIG. 10). The amino acids encoded by Exon 1, which encodes the signal peptide and propiece, and Exon 2, which encodes the mature cryptdin peptide, are indicated. A dot indicates the sequence was not encoded by the cDNA clone. "*" indicates a space, which preserves the homology of the sequences.

FIG. 9.B. indicates the degree of relatedness of the mouse cryptdins. Amino acids that are identical to the amino acid shown for cryptdin 1 (SEQ ID NO: 23) are indicated by a dot.

FIG. 10 shows the nucleic acid sequences for the cDNA sequences encoding mouse cryptdins 1–17 (SEQ ID NOS: 40 to 56, respectively). A consensus nucleotide sequence also is shown (SEQ ID NO: 57). A dot indicates the nucleotide is the same as shown for cryptdin 1. The amino acid sequence for cryptdin 1 (SEQ ID NO: 23) is shown above the nucleic acid sequence. Numbers below the nucleotide sequence indicate the nucleotide position relative to the methionine start codon (+1). Numbers above the amino acid sequence indicate the amino acid position. Italics indicate the mature cryptdin peptide sequence. Nucleotides in lower case letters indicate non-coding sequence. "***" indicates a stop codon. "(A)$_n$" indicates poly-A tail. "*" indicates a space and "-" indicates the particular nucleotide could not be determined unambiguously.

FIG. 11 shows the genomic DNA sequences for mouse cryptdins 1, 2, 3, 5 and 6 (SEQ ID NOS: 58 to 62, respectively) and the genomic sequence for the apparently inactivated mouse cryptdin i gene (Crypi; SEQ ID NO: 63), in which a stop codon (TGA) is substituted for a cysteine residue. Numbering is as described in the legend to FIG. 11. The upper sequence represents a consensus cryptdin gene sequence (SEQ ID NO: 64). "X" indicates positions at which at least two sequences containing nucleotide changes. The TATAAA box is shown in lowercase italics; exons are shown in capital letters; "**" indicates intron DNA; "n" represents approximately 500 base pairs that were not sequenced. "@" indicates the start of the cryptdin peptide coding region at codon 59. Coding sequences are indicated in bold print. Prepro-regions are coded by nucleotides 1–172; cryptdin peptides are coded by nucleotidase 173–279. The stop codon is underlined.

Figure 1:
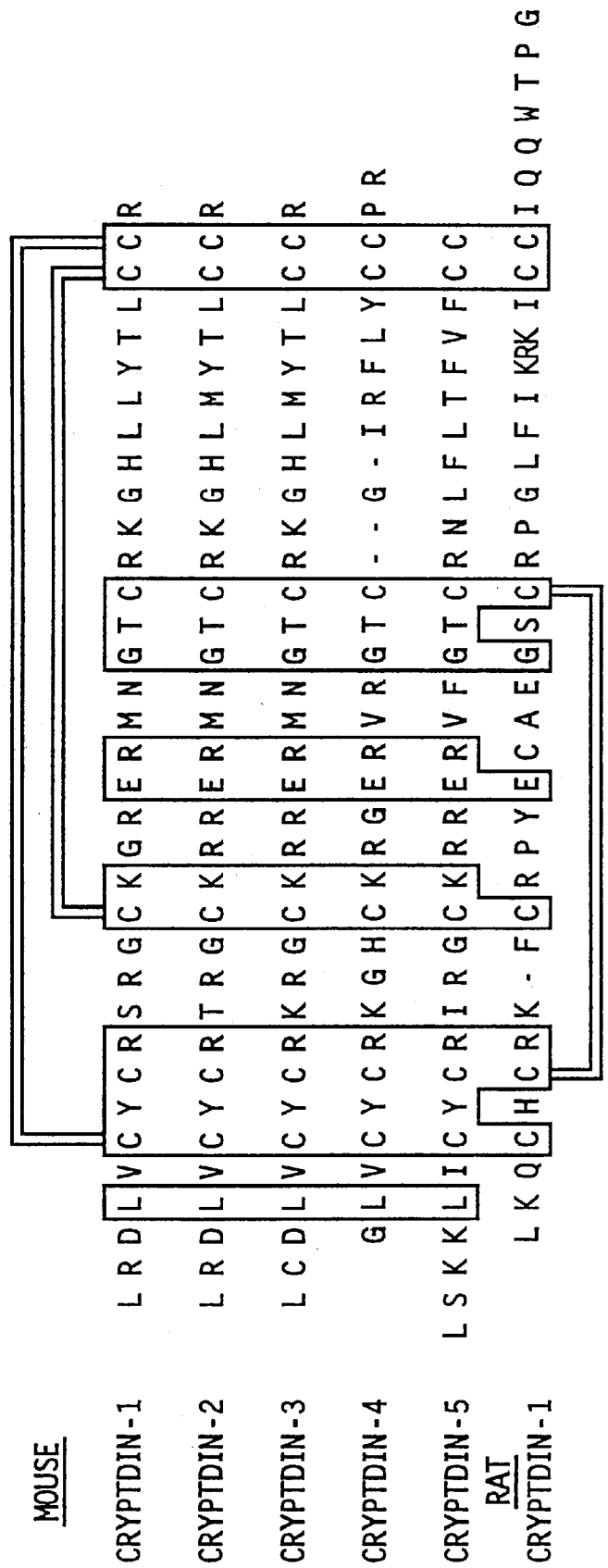
FIG. 1 provides the structures of mouse cryptdins 1–5 (SEQ ID NOS.: 9 to 10, respectively) and rat cryptdin 1 (SEQ ID NO: 11). Amino acid residues are indicated by single letter code. Dashed lines are included in mouse cryptdin 4 (SEQ ID NO: 9) and rat cryptdin 1 (SEQ ID NO; 11) in order to pregerve the consensus sequence where these peptides are shorter than other cryptdins. Invariant residues in the enteric cryptdin peptides are boxed. Disultide bonding motifs are depicted by connecting double lines.

GenBank accession numbers for these sequences are 02994 (cryptdin 1, exon 1); 002995 (cryptdin 1, exon 2); 02996 (cryptdin 2, exon 1); 002997 (cryptdin 2, exon 2); 002998 (cryptdin 3, exon 1); 002999 (cryptdin 3, exon 2); 003000 (cryptdin 5, exon 1); 003001 (cryptdin 5, exon 2); 002002 (crypdclin 6, oxon 1); 003003 (cryptdin 6, exon 2); 003004 (cryptdin i, exon 1); and 003005 (cryptdin i, exon 2).

Figure 12A:
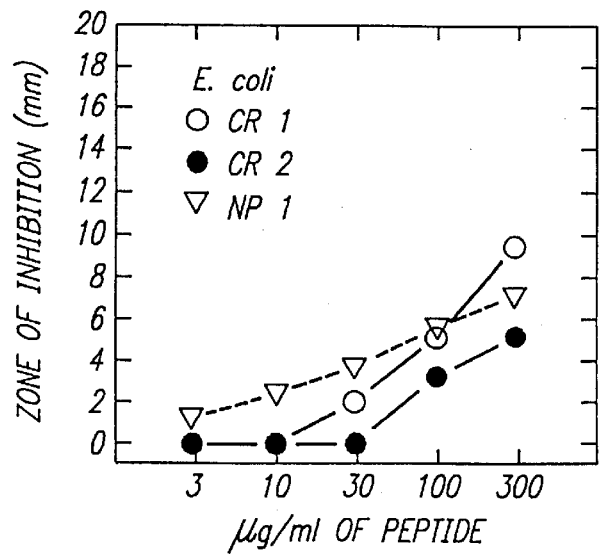
Figure 12B:
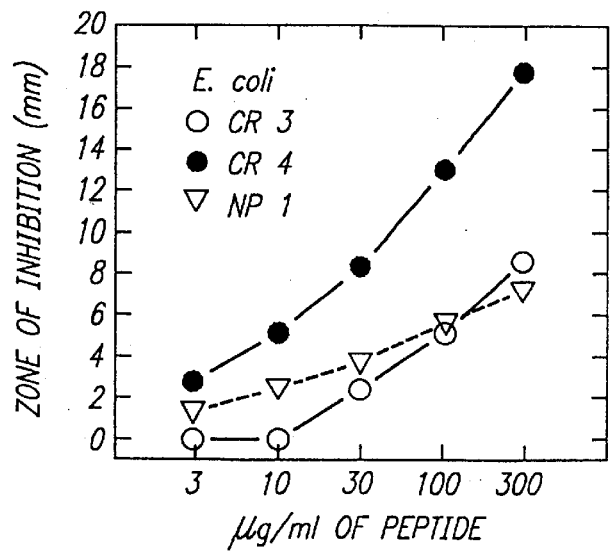
Figure 12C:
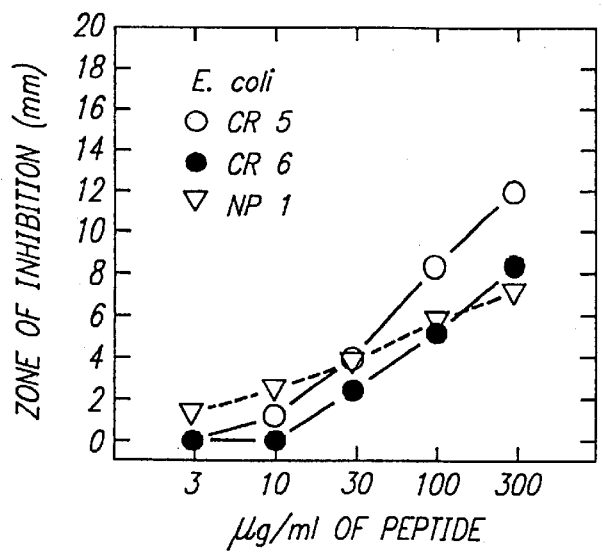

FIGS. 12.A. to 12.C. demonstrate the effectiveness of mouse cryptdins (as indicated) in inhibiting the growth of *E. coli* ML35 cells in an agar diffusion assay.

Figure 13A:
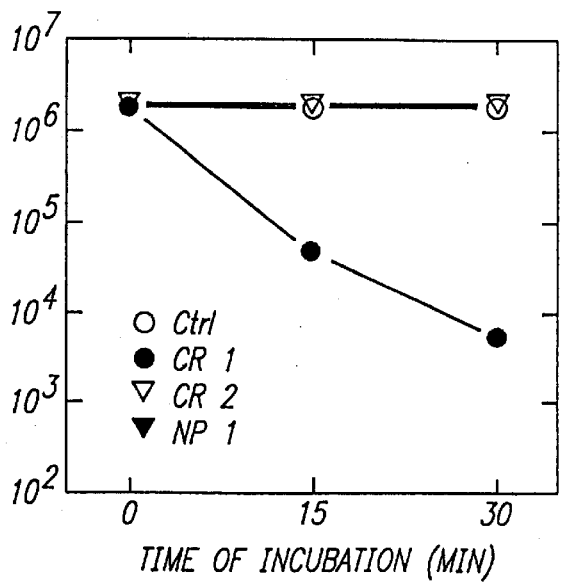
Figure 13B:
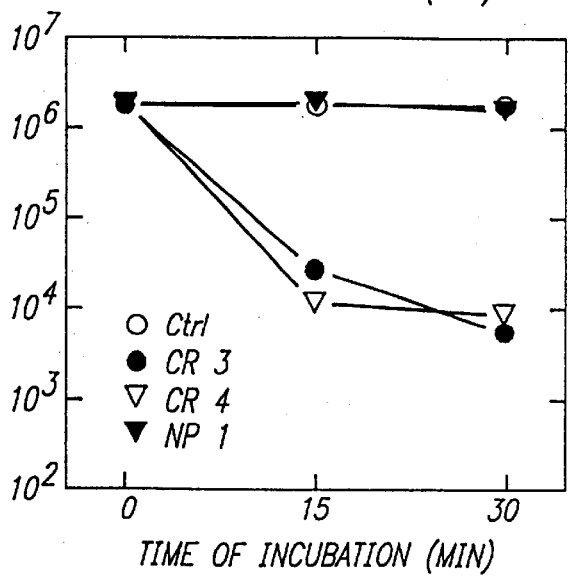
Figure 13C:
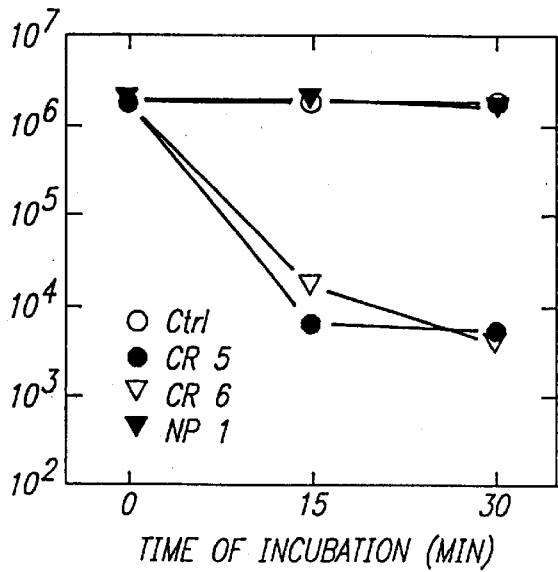

FIGS. 13.A. to 13.C. demonstrate the effectiveness of mouse cryptdins (as indicated) in killing *E. coli* cells in suspension.

FIGS. 14.A. to 14.C. show the cDNA sequences encoding rat cryptdin 1 (FIG. 14.A.), rat cryptdin 2 (FIG. 14.B.) and rat cryptdin 3 (FIG. 14.C.). Nucleotide numbers are indicated.

FIGS. 15.A. to 15.C. show the genomic DNA sequences encoding rat cryptdin 1 (FIG. 15.A.), rat cryptdin 2 (FIG. 15.B.) and rat cryptdin 3 (FIG. 15.C.). Nucleotide numbers are indicated.

DETAILED DESCRIPTION OF THE INVENTION

The invention provides small peptide molecules, termed cryptdins, which express a broad range of antimicrobial activity, particularly against intestinal pathogens, and for this reason are useful antimicrobial agents. For example, cryptdins have antimicrobial activity against gram negative and gram positive bacteria. and against protozoan pathogens (see Example III). cryptdin peptides and nucleic acid sequences encoding cryptdins were isolated from the small intestine and are active within the epithelial lining of the small intestine and within the lumen of the intestine. Because it is indicative of inflammatory processes, the presence df cryptdins can be utilized in the diagnosis of a wide range of inflammatory conditions.

As uged herein, the term "cryptdin" or "enteric defensins" refers to peptides having generally between about 30 and 45 amino acids. Cryptdins are characterized, in part, by a consensus sequence containing six cysteine residues. Illustrative seaienceas are provided in FIG. 1, which shows invariant residues and the disulfide bonding motif. In addition, those residues which are preferably invariant are identified (see, also, FIGS. 8 and 9).

Cryptdins are further characterized by their a citionlc charge and their broad range of antimicrobial activity. While related to leukocyte-derived defensins, cryptdins are distinguished from these other molecules by the presence of 3 to 9 amino acids N-terminal to the first cysteine molecule. Cryptdins may have C-terminal extensions as well. In addition, they exhibit antimicrobial activity against enteric microorganisms, which can become blood-borne pathogens if the intestinal barrier is breached. Since cryptdins are associated with the secretory granules of Paneth cells in the small intestine, they can be secreted from the cells in which they are produced (Satoh, *Cell Tiss. Res.* 251:87–93 (1988); Satoh et al., *Acta Histochem.* 83:185–188 (1988)). Unlike leukocyte-derived defensins, cryptdins are not toxic to mammalian cells.

It should be appreciated that various modifications can be made to the cryptdin amino acid sequence without diminishing the antimicrobial activity of the peptide. It is intended that peptides exhibiting such modifications, including amino acid additions, deletions or substitutions are within the meaning of the term "cryptdin" and, therefore, within the scope of the invention. For example, cryptdin analogs, which are devoid of one or more amino acids N-terminal to the first cysteine residue, are within the present invention. Such cryptdin analogs can be synthesized using well known methods (see Example VI) or can be purified from the intestine where they may occur naturally due, for example, to partial proteolysis of a cryptdin peptide in the intestinal lumen.

Use of the phrase "substantially pure" in the present specification and claims as a modifier of peptide, protein or nucleic acid means that the peptize, protein or nucleic acid so designated has been separated from its in vivo cellular environment. As a result of the separation and purification, the substantially pure peptides, proteins and nucleic acids are useful in ways that the non-separated impure peptides, proteins and nucleic acids are not.

The cryptdin peptides of the present invention preferably contain between about 30 and 45 amino acids (see FIGS. 1, 8 and 9). Cryptdins can be synthesized by methods well known in the art, such as through the use of automatic peptide synthesizers or by well-known manual methods of peptide synthesis (see Example VI). In addition, they can be purified from natural sources such as small intestinal epithelium of vertebrate, preferably mammalian, origin (see Example I). Such epithelium can be obtained, for example, from rats, mice or humans using means well known to those skilled in the art.

As disclosed herein, various cryptdin peptides were isolated from intestinal epithelium, purified by chromatographic methods and characterized by electrophoresis and amino acid sequencing. Cryptdins were identified by their rapid migration on acid-urea PAGE and by their apparent molecular weight of about 4 kDa (see Examples I and II).

Anti-cryptdin antibodies were made using methods conventional in the art. For example, polyclonal antiserum can raised in appropriate animals, such as rabbits, mice or rats. Cryptdin peptides, either synthetic or obtained from natural sources, can be used to immunize the animal. As described in Example IV, a cryptdin analog, cryptdin C, which corresponds to residues 4–35 of mouse cryptdin 1 (SEQ ID NO: 6) as shown in FIG. 1, was used to immunize rabbits using well known methods. Serum samples were collected until the anti-cryptdin titer was appropriate. Various fractions of the antiserum, such as IgG, can be isolated by means well known in the art. Cryptdin immunogens also can be used to obtain monoclonal antibodies using methods well known in the art (see, for example, Harlow and Lane, *Antibodies: A Laboratory Manual* (Cold Spring Harbor Laboratory Press 1988), which is incorporated herein by reference).

The antimicrobial activity of a cryptdin can be measured against various pathogens. As disclosed in Example III, various microorganisms were grown to an appropriate CgQ;tntration, mixed with an appropriate medium such as an agarose-trypticase soy medium and contacted with a cryptdin. Antimicrobial activity was apparent, for example, from the clear zones that surrounded the cryptdins in an agar diffusion assay. The area of the clear 7oneg was concentration dependent (see FIG. 12).

Anti-cryptdin antibodies can be used to determine the presence of cryptdin in a biological sample such as a histological sample. For example, sections of small intestine are fixed by means well known to those skilled in the art and incubated with anti-cryptdin antibodies such as an IgG fraction of antiserum. If desired, the anti-cryptdin antibody can be detectably labeled or an appropriate detectable second antibody can be used to identify the presence of the primary antibody attached to the cryptdin. Means of detection include the use of radioactive protein A or enzyme substrates such as peroxidase (see Harlow and Lane, supra, 1988).

Alternative methods of determining the presence of cryptdin in a biological sample obtained, for example, by intestinal lavage or by disrupting cells or tissues can be useful to determine the presence of inflammatory processes. In the presence of inflammatory processes, the concentration of cryptdins is significantly altered from that found in the normal cell In particular, a deviation from the normal level of cryptdins by one to two standard deviations is indicative of an inflammatory process. Such an inflammatory process can include, for example, inflammatory bowel disease, pancreatitis, malignancy, infection or ileitis.

Because of their broad range of antimicrobial activity and their ability to function within the intestinal epithelium or lumen, cryptdins are potent therapeutic agents for infections of the intestine. In particular, cryptdins are useful where the subject is immunocompromised due, for example, to malignancy, malnutrition, chemotherapy, radiation, immunosuppressive viruses, autoimmune disease or neonatality. In addition, cryptdins are useful in surgical prophylaxis, for example, by functioning to help sterilize the small bowel. Thus, cryptdins can be useful as medicaments for treating a subject having a pathology characterized, in part, by an inflammatory process A cryptdin, either purified from natural sources or synthetic, can be administered to a subject in need of such therapy by various means, including orally; preferably in a slow-release type formulation, which will avoid release within the stomach. Alternatively, cryptdins can be administered through nasogastric intubation, transabdominal catheter, intravenously or aerosol administration. Individual species of cryptdin can be administered alone or in combination Cryptdins administered in combination can be administered simultaneously or sequentially and can be repeated as necessary.

Prior to the characterization of a mouse intestinal defensin cDNA, expression of defensins was thought to be limited to professional phagocytes, i.e., neutrophils and macrophages. The presence of high levels of cryptdin mRNA in Paneth cells led to the hypothesis that defensins synthesized in intestinal epithelium may contribute to antimicrobial barrier function in the small bowel (Ouellette et al., *J. Cell Biol.* 108:1687–1695 (1989a), which is incorporated herein by reference). Isolation and characterization of six mouse cryptdin peptides, two rat cryptdin peptides and 2 human cryptdin peptides, and the demonstration of antimicrobial activity of various cryptdin peptides indicates that the cryptdins have an antimicrobial role in the gmall intestine. The immunohistochemical localization of cryptdin(s) to Paneth cells is consistent with previous in situ hybridization analysis and suggests that dtfensins produced by three cells may contribute to restricting the colonization and invasion of the small bowel by bacteria.

Figure 2A:
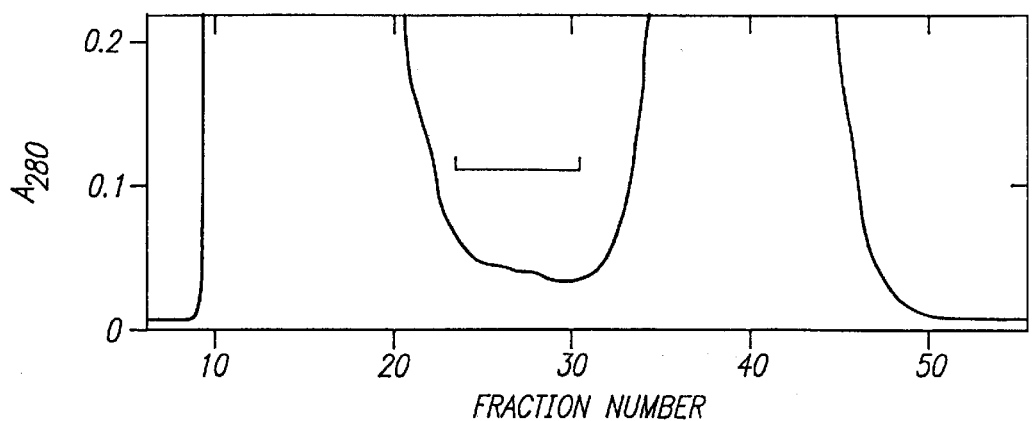
FIGS. 2.A. to 2.C, show chromatograms representing the purification of enteric cryptdins. Acid extract of jejunum and ileum was chromatographed in 30% acetic acid on a P-60 column. Fractions indicated by the bracket (FIG. 2.A.) were pooled and rechromatographed on the P-60 column (FIG. 2.B.). Cryptdin containing fractions (bracket, panel B) were pooled and further purified by reversed-phase high performance liquid chromatography (RP-HPLC) on 0.46×25 cm Vydac C-18 column. Water-acetonitrile gradient elution (--) using 0.13% (vol/vol) HFBA as modifier was used to purify cryptdins 1–5 (SEQ ID NOS: 6 to 10, respectively) The brackets in FIG. 2.C. indicate the peptide contained in each peak, and the portion of each which was subjected to a second round of RP-HPLC.
Figure 2B:
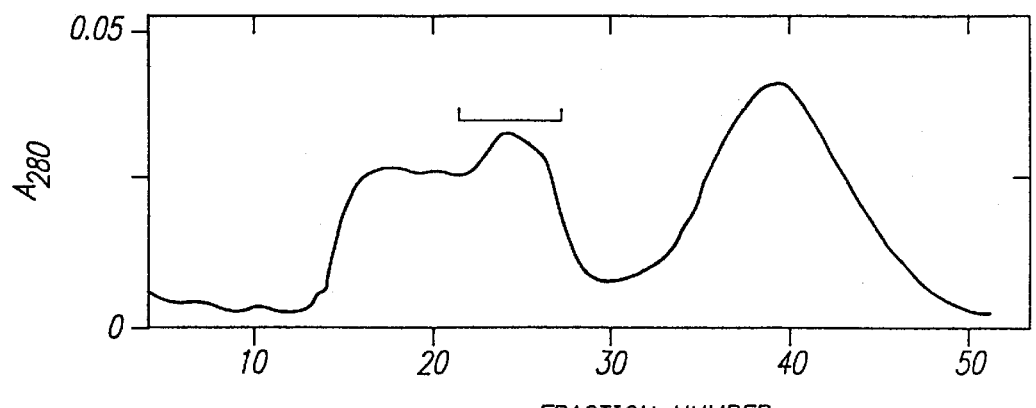
Figure 2C:
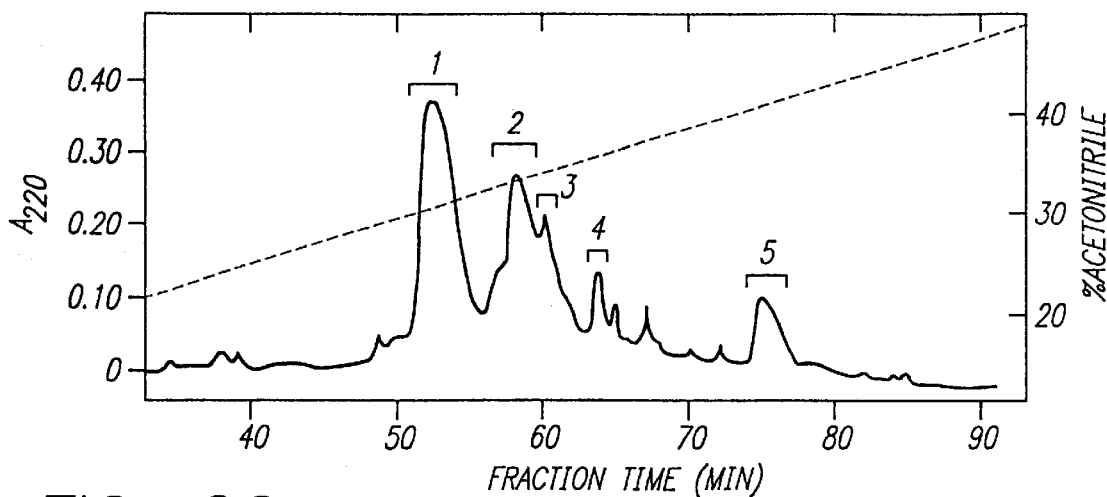
Figure 3:
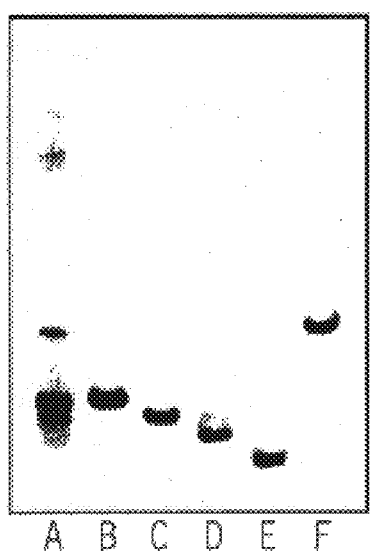
FIG. 3 shows acid-urea PAGE of purified enteric cryptdins. Samples of low molecular weight enteric peptides obtained by P-60 gel filtration (FIG. 2, panel B) and purified cryptdins were electrophoresed on a 12.5% acid-urea gel and stained with formalin-containing Coomassie Blue. Lane A: approximately 20 µg P-60 low molecular weight peptide fractions; lanes B–F: 1 µg each of cryptdins 1–5 (SEQ ID NOS: 6 to 10), respectively.

Initial efforts to purify intestinal defensins focused on the isolation of mouse cryptdin 1 (SEQ ID NO: 6), the peptide predicted from the cryptdin oDNA sequence. Since the deduced structure of the peptide is highly cationic, intestinal peptides were solubilized by homogenizing intact mouse jejunum and ileum in 30% formic acid. Acid-urea PAGE of the crude extract revealed several bands with Rf values similar to those of rabbit defensin NP-1 and cryptdin C, a folded synthetic defensin congener corresponding to residues 4 to 35 in cryptdin 1 (SEQ ID NO: 6). Peptides corresponding to these bands were purified approximately 200-fold by sequential gel filtration chromatography on Bio-Gel P-60 (FIGS. 2.A. and 2.B.). Electrophoresis of P-60 column fractions on acid-urea gels showed that five fractions eluting between two prominent peaks (FIGS. 2.A. and 2.B., brackets) contained putative cryptdin peptides (FIG. 3, lane a). Peptides in these P-60 fractions migrated with an apparent molecular mass of approximately 4 kDa on SDS-PAGE (not shown), consistent with the molecular weight of defensins. Furthermore, treatment of P-60 fraction samples with performic acid reduced the electrophoretic mobility of the five putative mouse cryptdins in acid-urea gels, behavior that is characteristic of defensins and polypeptides that contain multiple cysteine residues.

Defensins in pooled P-60 fractions were purified further using sequential rounds of RP-HPLC utilizing different ion-pair agents. Initial HPLC fractionation utilized water-acetonitrile gradients containing 0.13% heptafluorobutyric acid (HFBA) as the ion-pairing agent, whereby nach of the five peptides contained in the pooled P-60 fractions was resolved to near purity in a single run (FIG. 2.C.). Complete purification of five peptides, mouse cryptdins 1–5 (SEQ ID NOS: 6 to 10, respectively), was achieved by subsequent RP-HPLC using 0.1% trifluoroacetic acid (TFA) (FIG. 3, lanes B–F). Assuming extraction of individual peptides is equally efficient, both acid-urea gel electrophoresis and RP-HPLC of the P-60 fractions containing putative cryptdins showed that the relative abundance of the peptides is cryptdiR 1>cryptdin 2>cryptdin 5>cryptdin 3>cryptdin 4. The relative amounts of cryptdins 1–5 (SEQ ID NO: 6 to 10, respectively) have been qualitatively reproducible in every preparation of acid-extracted protein from mouse small intestine.

Using a modification of the method described above, mouse cryptdin 6, rat cryptdin 2, and human cryptdins 5 and 6 also were isolated (see Examples I and II; see, also, FIGS. 8 and 9). In addition, longer forms of mouse cryptdins 4 and 5 (compare SEQ ID NOS: 9 and 12; 10 and 13) and rat cryptdin 1 (compare SEQ ID NOS: 11 and 15) were obtained. This result suggests that the initial method of purifying cryptdin peptides resulted in partial degradation of the C-termini of some peptides. Significantly, both forms of the purified cryptdin peptides have antimicrobial activity.

Biochemical characterization of the isolated cryptdins demonstrated that these peptides are defensins. Amino acid analysis of each peptide showed their compositions (cationic peptides of about 30 to 45 amino acid residues, including 6 half-cysteines) are compatible with defensin-like molecules. The complete sequences of mouse cryptdins 1–6 (SEQ ID NOS: 23 to 28), rat cryptdins 1 and 2 (SEQ ID NOS: 11, 15 and 16) and human cryptdins 5 and 6 (SEQ ID NOS: 18 and 19) were determined by automated Edman degradation and, in some cases, by amino acid analysis of carboxyl terminal chymotryptic peptides (see FIGS. 1, 8 and 9). The primary structures of the cryptdins contain the distinctive structural features of human, rabbit, rat and guinea pig neutrophil defensins (Lehrer et al., *Cell* 64:229–230 (1991a), which is incorporated herein by reference), i.e., the six invariant cysteine residues and the glycine and glutamic acid in positions that are highly conserved in myeloid defensins.

The cryptdin peptides disclosed herein contain features that are unique and distinct from defensins of myeloid origin. For example, mouse cryptdins 1, 2, 3 and 6 (SEQ ID NOS: 23 to 25 and 28, respectively) are almost identical, differing only at two or three positions (see FIG. 9.A.). Analysis of codons from which these amino acid differenceo could arise shows that the conversion, for example, of $Ser^{10}$ to $Lys^{10}$ in cryptdin 1 (SEQ ID NO: 23) and cryptdin 3 (SEQ ID NO: 25), respectively, requires two nucleotide substitutions. On the other hand, single nucleotide changes in the codon encoding $Thr^{10}$ in cryptdiln 2 (SEQ ID NO: 24) could give rise to cryptdins 1, 3 and 6, suggesting that the cryptdin 2 gene may be an intermediate or progenitor of the cryptdin 1, 3 and 6 genes. Similarly, a single nucleotide change in the codon for $Thr^{10}$ of cryptdin 2 can account for the deduced amino acid at position 10 in cryptdins 7–17 (see FIG. 10, nucleotides 203–205; SEQ ID NOS: 46 to 56).

By homology with the structures of known myeloid defensins, the cryptdin 1 N-terminus was predicted to begin at $Leu^4$ or $Val^5$, which is 1–2 residues prior to the first conserved cysteine. However, compared to myeloid defensins, cryptdins have variably extended N-termini that contain from three (mouse cryptdin 4, SEQ ID NO: 26; rat cryptdin 1, SEQ ID NO: 11) to nine (human cryptdin 5, SEQ ID NO: 18) amino acids preceding the first cysteine. In mouse cryptdins 1–3 and 6–17 (SEQ ID NOS: 23 to 25 and 28 to 39, respectively), the N-peptidyl extensions consist of two charged internal residues flanked by amino acids with hydrophobic sidechains. Since natural variation in dofengin amino termini correlates with relative antimicrobial potency in vitro (Ganz et al., *J. Clin. Invest.* 76:1427–1435 (1985), which is incorporated herein by reference), the extended N-termini of enteric defensins may have evolved for a unique role in the bowel.

Mouse cryptdin 4 (SEQ ID NO: 9), the most cathodal and, apparently, least abundant mouse enteric defensin, was the first defensin found to contain a chain length variation between the fourth and fifth cysteine residues. Unlike the majority of previously known defensins, in which nine amino acids separate the fourth andl fifth cysteines (Lehrer et al., supra, 1991a), mouse cryptdin 4 (SEQ ID NO: 9) contains only six residues between the same two amino acids (FIG. 1). In addition, rat cryptdins 1–3 (SEQ ID NOS: 11 and 15–17) contain ten amino acid residues between the fourth and fifth cysteines. These findings indicate the defensin fold involving this stretch of the peptide chain can accommodate significant variability in the size of the loop, as compared to the invariant loop size defined by crystal and NMR structures, respectively, of human and rabbit neutrophil defensins. Also, rat cryptdins 1–3 (SEQ ID NOR: 11 and 15–17) are the only cryptdins containing three, instead of four, amino acid residues between the second and third cysteine residues.

Since cryptdin mRNA levels increase during postnatal development of mouse small bowel (Ouellette et al., supra, 1989a), it was investigated whether accumulation of enteric defensins was regulated similarly. Analysis of intestinal acid extracts from male and female mice showed that mouse cryptdino 1–3 and 5 (SEQ ID NOS: 6 to 8 and 10, respectively) are present in adult mice, regardless of gender. On the other hand, extracts from 9 day-old mice lack the peptides, consistent with postnatal accumulation of cryptdin mRNA.

Figure 5:
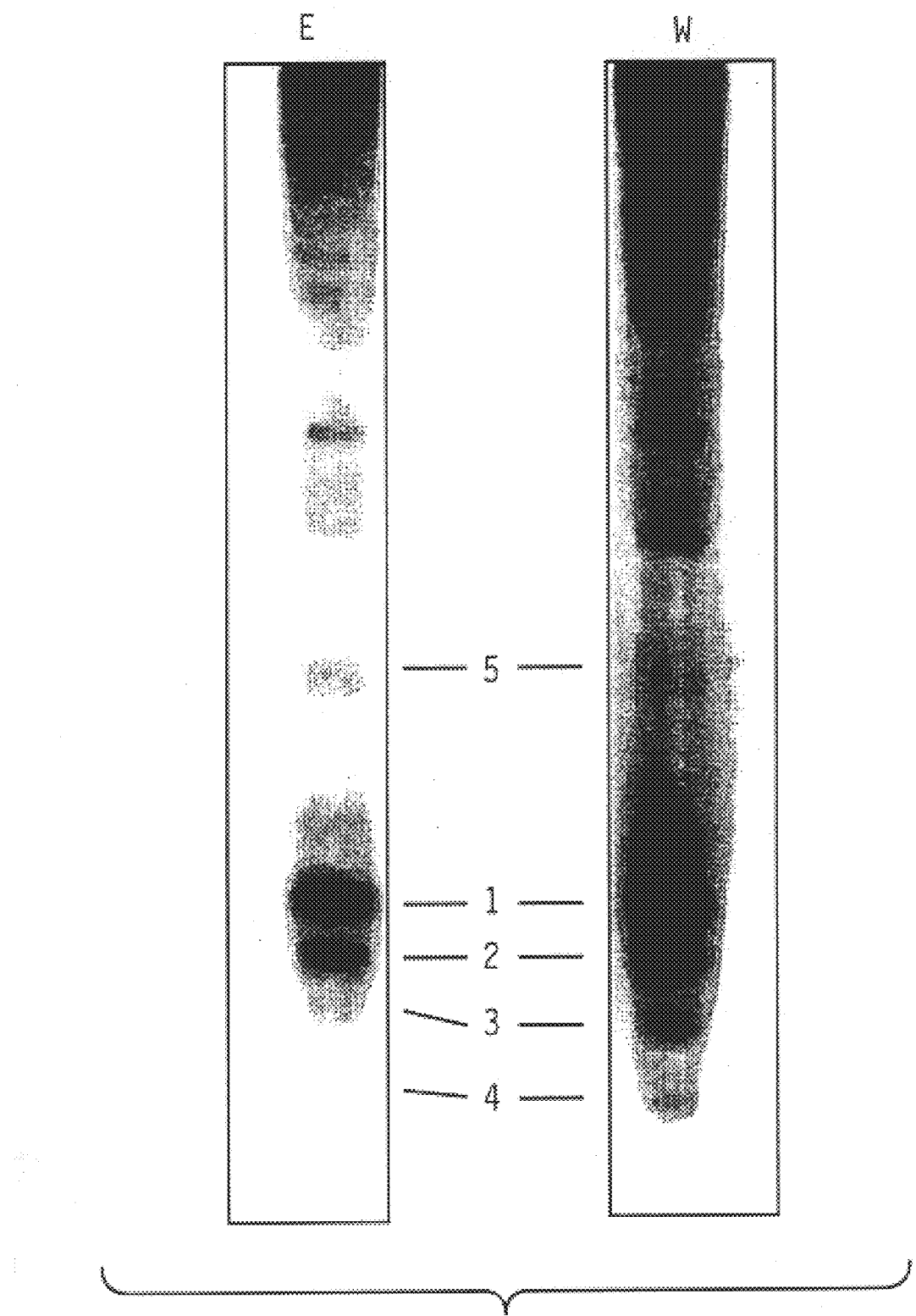
FIG. 5 shows the identification of mouse cryptdins 1–5 (SEQ ID NOS: 6 to 10, respectively) in small intestine epithelium. Acid extracts of intact, whole small intestine (w) or epithelial sheets (E) were lyophiliced, dissolved in sample solution and resolved on a 12.5% acid-urea acrylamide gel. Cryptdins 1–5 (SEQ ID NOS: 6 to 10) are identified numerically.
Figure 6A:
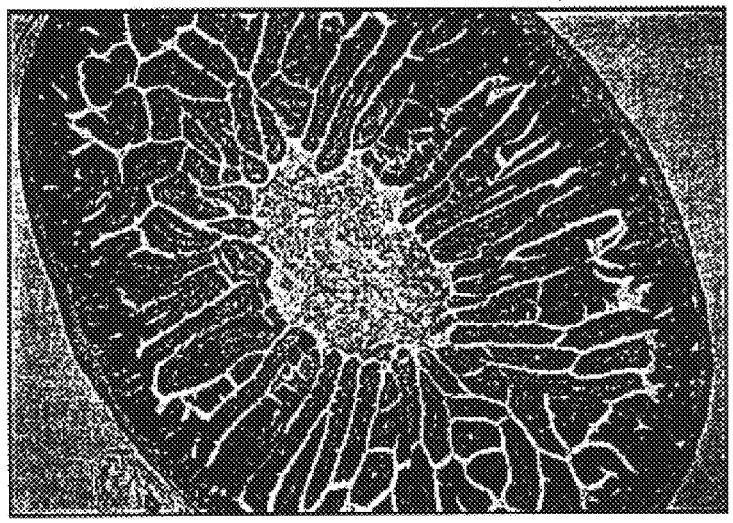
FIGS. 6.A. to 6.F. show the immunohistochemical localization of cryptdin 1 (SEQ ID NO: 6) in small intestine. Full thickness sections of adult mouse jejunem were incubated with preimmune (FIGS. 6.A., 6.C. and 6.E.) or anti-cryptdin C rabbit IgG (FIGS. 6.B., 6.D. and 6.F.) and developed using peroxidase anti-peroxidage secondary antibody magnifications.
Figure 6B:
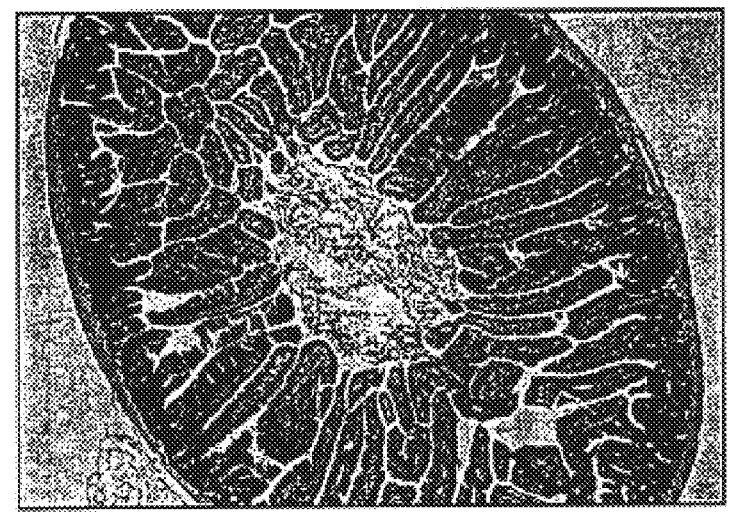
Figure 6C:
Figure 6D:
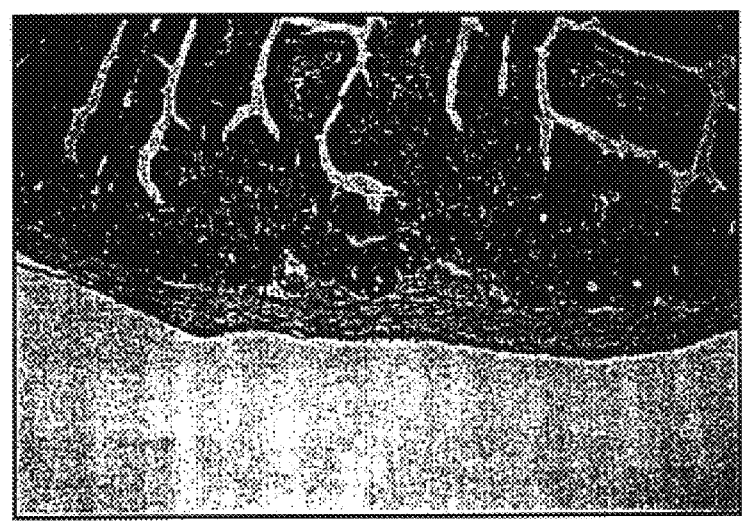
Figure 6E:
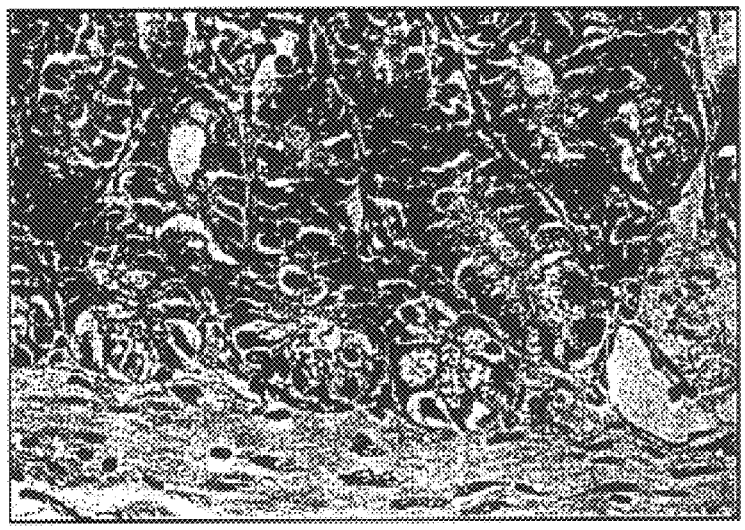
Figure 6F:

Mouse cryptdins 1–5 (SEQ ID NOS: 6 to 10) were purified from intestinal epithelial cells. In the presence of EDTA, the intestinal epithelium no longer adheres to the underlying basement membrane and floats free of the lamina propria upon gentle agitation (Bjerknes and Cheng, *Am. J. Anat.* 160:51–63 (1981), which is incorporated herein by reference). Preparations of epithelial sheets isolated in this manner were concentrated by low speed centrifugation and extracted with 30% formic acid. Peptides extracted from isolated epithelial sheets comigrate with cryptdins 1–5 (SEQ ID NOS: 6 to 10) when analyzed by acid-urea PAGE (FIG. 5), demonstrating their epithelial origin.

Immunoperoxidase staining of full-thickness sections of small intestine with an anti-cryptdin antibody demonstrate cryptdin antigen in Paneth cells, consistent with localization of cryptdin mRNA by in situ hybridization (Ouellette et al., supra, (1989a)). Incubation of sections of adult mouse jejunum and ileum with a polyclonal anti-cryptdin IgG produced by rabbits immunized with the synthetic congener cryptdin C localized the immunoperoxidase reaction to granulated cells, morphologically defined as Paneth cells, at the base of every crypt (FIG. 6). The staining pattern accentuates the granular appearance of the cytoplasm in these cells and the immunoreactivity appears particularly strong over Paneth cell granules. The antibody is specific for mouse cryptdin(s), since it is negative both for rat and human Paneth cells (data not shown). Leukocytes in the lamina propria of the villi also were negative, suggesting that related enteric defensins are not expressed by phagocytes or lymphocytes. Because of the extensive similarity of mouse cryptdins 1–3 (FIG. 1; SEQ ID NOS: 6 to 8), the polyclonal antilody produced against cryptdin C probably recognizes the three peptides. Conversely, because mouse cryptdin 4 (SEQ ID NO: 9) and cryptdin 5 (SEQ ID NO: 10) differ markedly from the other mouse cryptdins, the anti-cryptdin C antibody is unlikely to react with cryptdin 4 (SEQ ID NO: 9) and cryptdin 5 (SEQ ID NO: 10), leaving their origin in Paneth cells somewhat unresolved.

Figure 4:
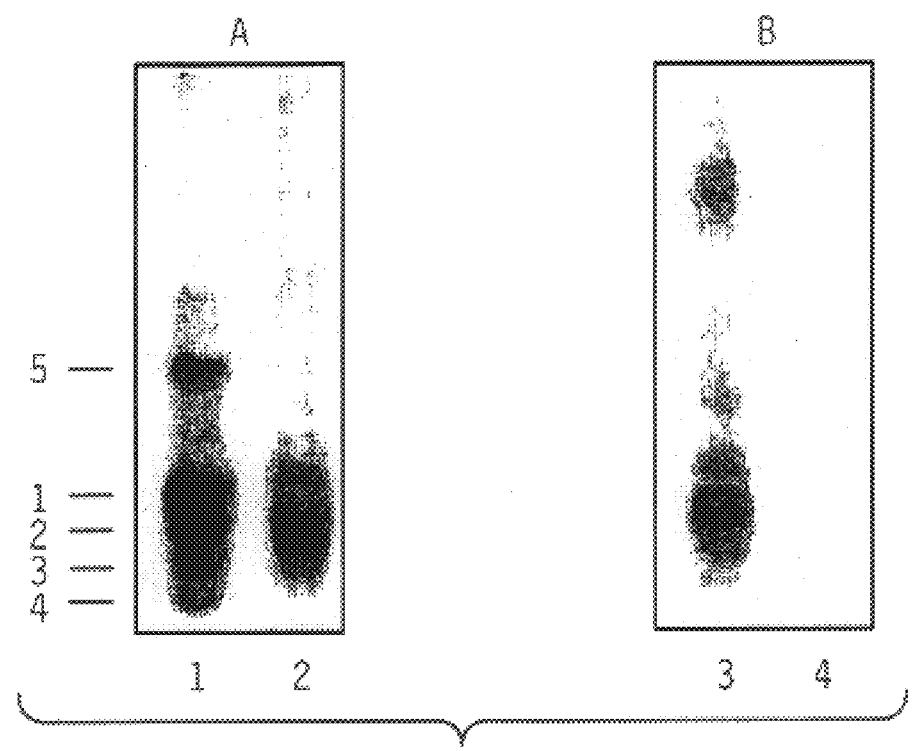
FIGS. 4.A. and 4.B. compare mouse cryptdins 1–5 (SEQ ID NOS: 6 to 10, respectively) and partially purified luminal peptides.

Immunohistochemical data suggest cryptdins are secreted into the intestinal lumen. Material in the small intestinal lumen is strongly pogitive for the antibody but negative for preimmune sera or IgG (FIGS. 6.A. and 6.B.). Although the agonist for Paneth cell defensin secretion is unknown, lysozyme, another protein constituent of Paneth cell granules, is secreted into the lumen under cholinergic regulation. Consistent with immunochemical detection of anticryptdin C positive material in the intestinal lumen, acid-urea PAGE of saline washes of adult jejunum and ileum contain peptides with mobilities very similar to but distinct from the mobility of cryptdins (FIG. 4). Nevertheless, the peptides are not identical to cryptdins 1–5 (SEQ ID NOS: 6 to 10, respectively) by either migration in acid-urea PAGE or by HPLC analysis, suggesting they may correspond to cryptdins that have been processed further. Conceivably, luminal cryptdin or cryptdin-like material could derive from exfoliated Paneth cells in the lumen, but the low rate of Paneth cell turnover suggests this is unlikely. The release of cryptdins or processed variants into the small bowel by Paneth cells contrasts with the apparent lack of defensin secretion by leukocytes, and it is inferred that a secretory pathway may exist for the constitutive delivery of defensins into the intestinal lumen by Paneth cells.

The antibacterial activity of purified mouse cryptdins 1–5 (SEQ ID NOS: 6–10) was tested against wild type and phoP mutant *S. typhimurium* using a modified plate diffusion assay (Lehrer et al., *J. Immunol. Methods* 137:167–173 (1991b), which is incorporated herein by reference). phop is a two-component regulatory locus that is essential to *S. typhimurium* virulence and survival within macrophages (Fields et al., *Science* 243:1059–1062 (1989); Miller et al., *Proc. Natl. Acad. Sci., USA* 86:5054–5058 (1989), each of which is incorporated herein by reference). Mutants in the phoP locus are particularly sensitive to rabbit defensins NP-1 and NP-2 when compared to wild type parent strains (Fields et al., supra, 1989; Miller et al., *Infect. Immun.* 58:3706–3710, (1990), which is incorporated herein by reference).

Figure 7A:
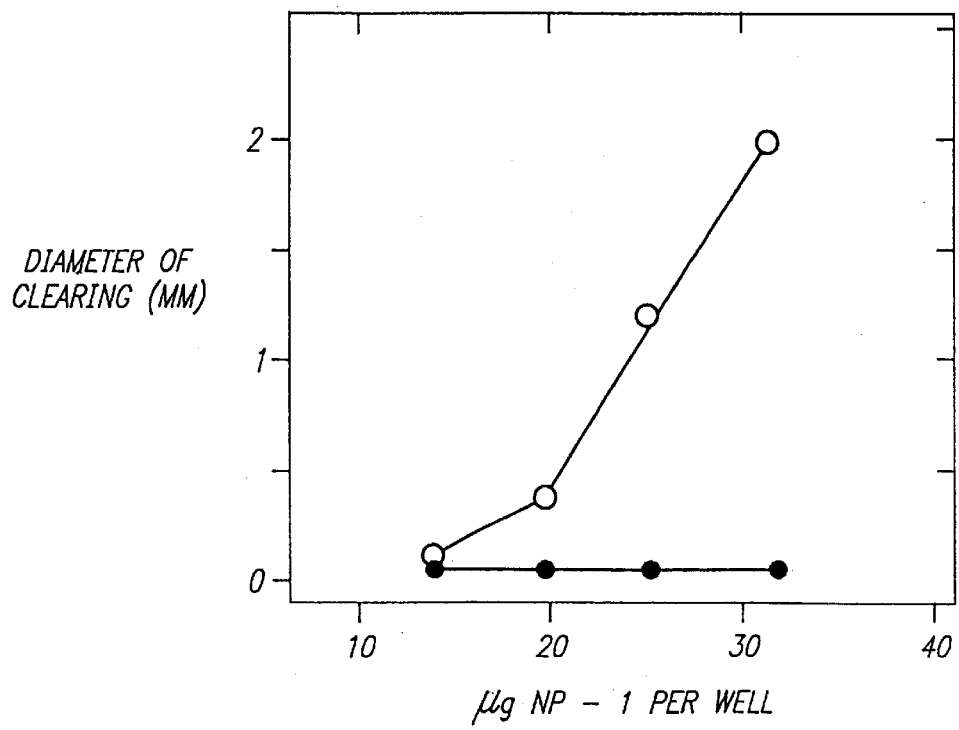
FIGS. 7.A. and 7.B. depict the antimicrobial activity of mouse cryptain 1 (SEQ ID NO: 6). Samples of purified natural mouse cryptdin 1 (FIG. 7.A.) or rabbit NP-1 (FIG. 7.B.) were dissolved in 0.01% acetic acid and pipetted into wells produced in a 0.6, agarose/0.3% tryptone plate containing 1×10⁶ log phase bacterial cells. After incubation at 37° C. for 18 hr, antimicrobial activity was evaluated by measuring the diameters of the clear zones. Closed circles denote wild type *S. typhimurium*; open circles denote the phoP⁻ mutant.
Figure 7B:
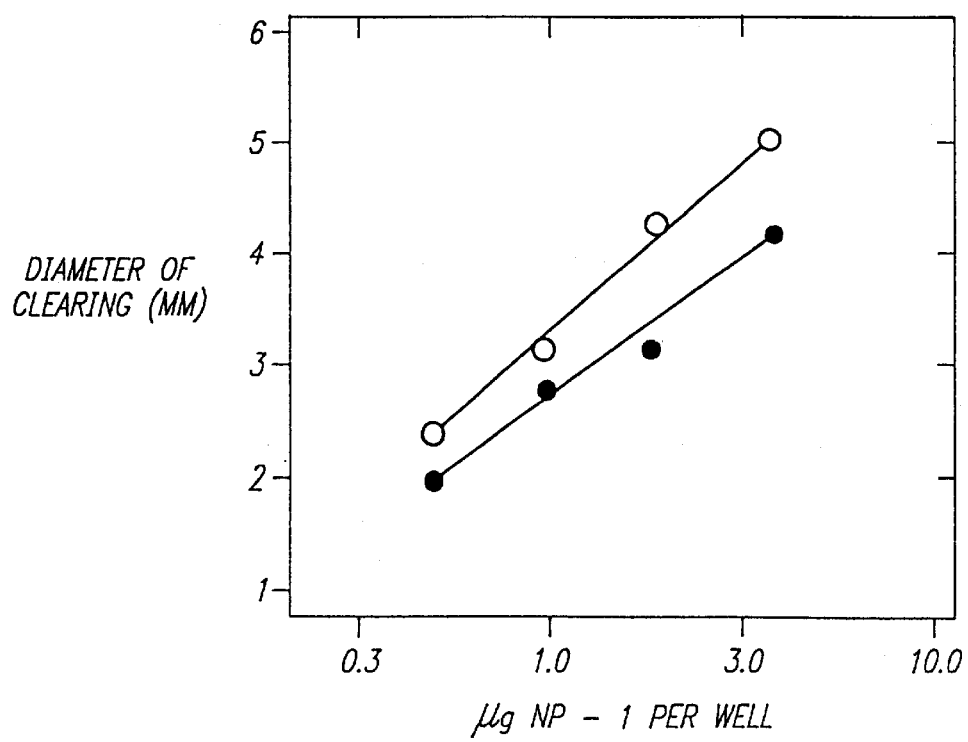

Under assay conditions using a phosphate buffer as described in Example III, the antimicrobial activity of rabbit defensin NP-1 against wild type and the phoP mutant organisms was quite similar (FIG. 7.B.). On the other hand, at concentrations of mouse cryptdin 1 (SEQ ID NO: 6) that are effective against the attenuated mutant, wild type *S. typhimurium* is completely resistant to the effects of the peptide (FIG. 7.A.).

The differential activity of cryptdin 1 (SEQ ID NO: 6) against avirulent *S. typhimurium* suggests that resistance to mucosal defensins may be important for the evolution of virulence in enteric pathogens. However, in experiments using HEPES or PIPES as buffers as described in Example III, concentrations of 100 μg/ml or 300 μg/ml cryptdin 1 were as effective as NP-1 in inhibiting the growth of wild type *S. typhimurium*. Furthermore, at these concentrations, cryptdins 4 and 5 were more effective than NP-1 in preventing the growth of mutant and wild type *S. typhimurium* (not shown).

Figure 10A:
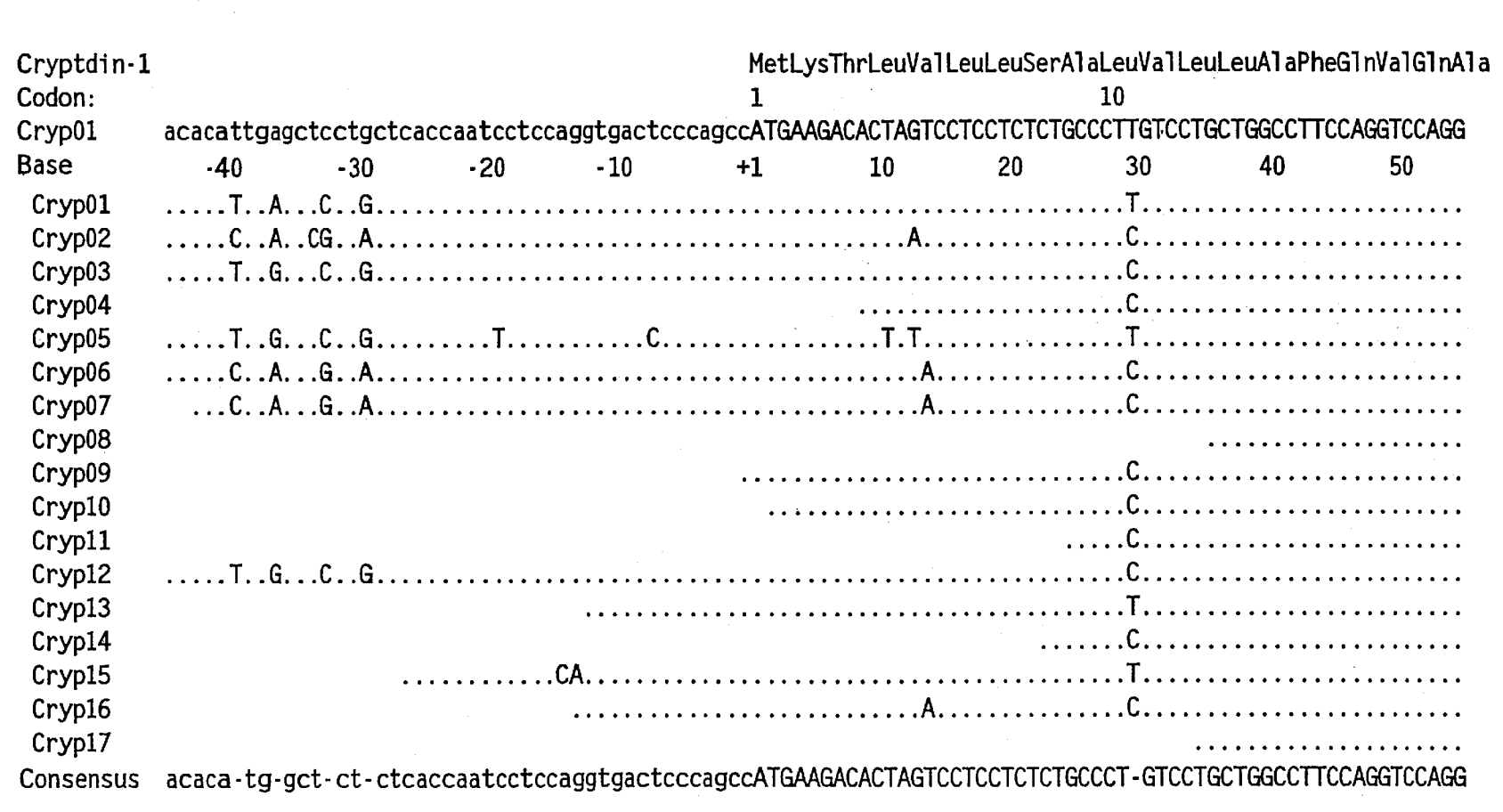
Figure 11A:
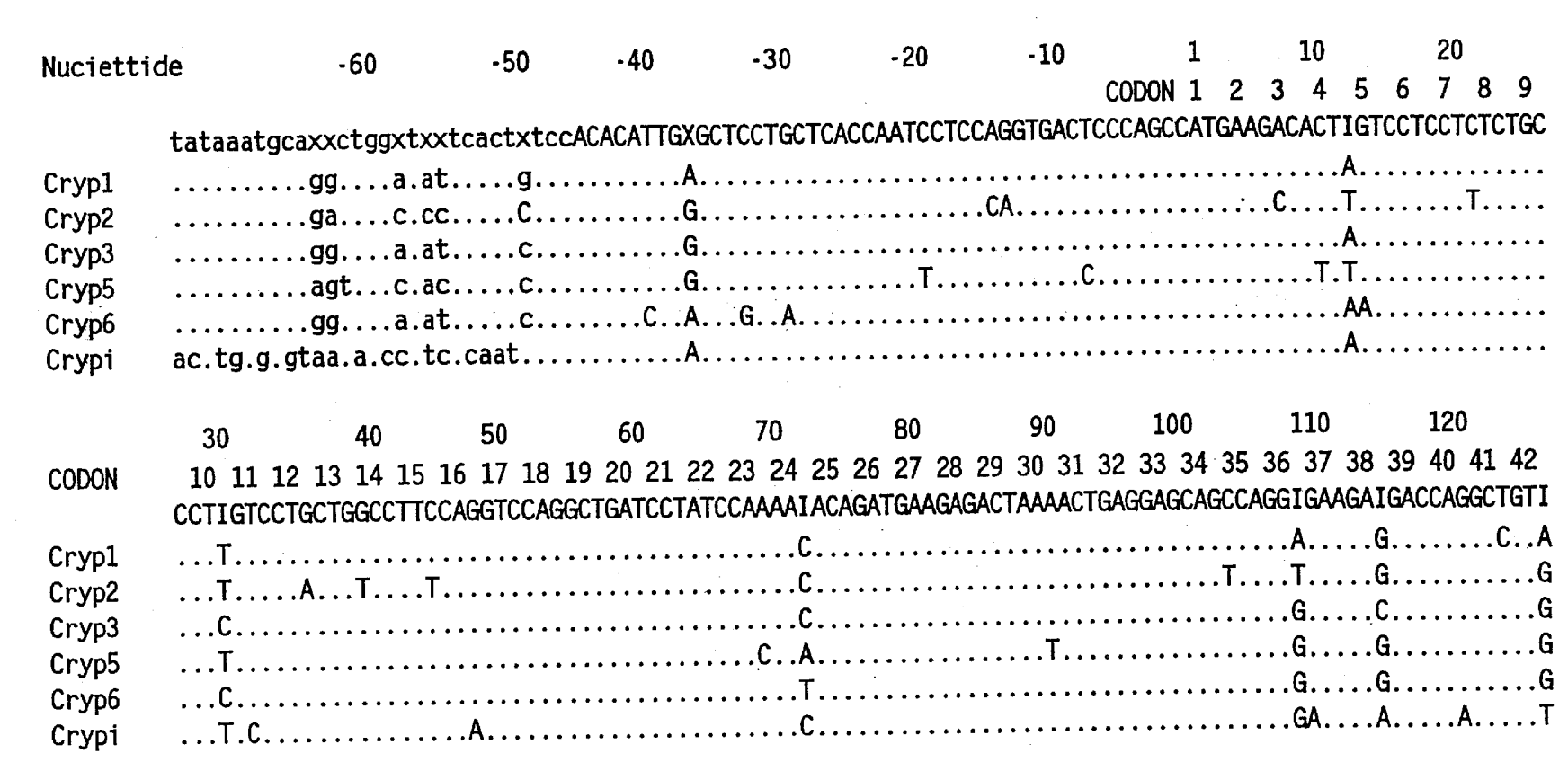

The present invention also provides substantially purified nucleic acid sequences encoding cryptdins. For example, the cDNA sequences for mouse cryptdins 1–17 (SEQ ID NOS: 40–56) are shown in FIG. 10 and the cDNA sequences for rat cryptding 1–3 (SEQ ID NOS; 65–67) are shown in FIGS. 14.A. to 14.C. In addition, the genomic DNA sequences for mouse cryptdins 1, 2, 3, 5 and 6 (SEQ ID NOS: 58–62) and for an apparently inactivated cryptdin gene, cryptdin i (SEQ ID NO: 63) are shown in FIG. 11 and the genomic DNA sequences for rat cryptdins 1–3 (SEQ ID NOS: 68–70) are shown in FIGS. 15 A. to 15.C.

The skilled artisan would recognize that various nucleotide substitutions could be made in the nucleic acid sequences shown in FIGS. 10, 11 14 and 15 without altering the amino acid sequence of the encoded cryptdin peptide due to degeneracy of the genetic code. Such nucleotide sequences, which are equivalent to the sequences shown in FIGS. 10, 11, 14 and 15 are encompassed within the claimed invention.

The invention also provides nucleotide sequences that consist of a portion of a nucleic acid sequence as shown in FIGS. 10, 11, 14 and 15. such a nucleotide sequence can be useful, for example, as a probe, which can hybridize under relatively stringent conditions to a nucleic acid molecule encoding a cryptdin peptide. For hybridization, such a nucleotide sequence should be at least about 10 nucleotides in length. One skilled in the art would know that appropriate conditions for hybridization can be determined empirically or can be calculated based, for emample, on the G:C content of the nucleotide sequence, the length of the sequence and the number of mismatches, if any, between the probe and the target sequence (see, for example, Sambrook et al., *Molecular Cloning: A laboratory manual* (Cold Spring Harbor Laboratory Press 1989), which is incorporated herein by reference).

A nucleotide sequence as described above can be detectably labeled by attaching, for example, a radioactive label or biotin, or can be unlabeled. A labeled or unlabeled sequence also can be used as a primer for the polymerase chain reaction (PCR; see, for example, Erlich, *PCR Technology: Principles and applications for DNA amplification* (Stockton Press 1989), which is incorporated herein by reference). Such a sequence can be useful, for example, to identify a nucleic acid sequence encoding a cryptdin in a cell.

A nucleic acid molecule as shown in FIGS. 10, 11, 14 and 15 or a nucleotide sequence derived therefrom also can be useful, for example, for preparing a cryptdin peptide or a portion of a cryptdin peptide using well known methods of recombinant DNA technology. For example, the nucleic acid sequence can be cloned into an expression vector such as a baculovirus vector or a viral vector, which can infect a mammalian cell and express an encoded cryptdin peptide in the cell. Expression from such a vector can be useful for producing large amounts of a cryptdin, which can be used to treat a subject having an inflammatory pathology as described herein, or for producing a cryptdin directly in a subject. Thus, the invention provides vectors containing a nucleic acid molecule as shown in FIGS. 10, 11, 14 and 15 as well as specific host cells, in which the vector can propagate or can express a cryptdin.

The following examples are intended to illustrate but not limit the invention.

EXAMPLE I

Purification of Enteric Defensins

Outbred Swiss mice, (Crl:CD-1) (ICR)BR, 45 day old males (30–35 g) or timed-pregnant dams, were obtained from Charles River Breeding Laboratories, Inc. (North Wilmington Mass.). In studies of newborn mice, litters were culled to 8 pups within 12 hr of delivery Mice were housed under 12 hr cycles of light and darkness and had free access to food and water.

Cryptdins were isolated by a modification of the method described by Selsted et al., *J. Cell. Biol.* 118:929–936 (1992); Ouellette et al., *Infect. Immun.* 62:5040–5057

(1994), each of which is incorporated herein by reference. Jejunal and ileal intestinal segments were excised from 60 mice immediately after carbon dioxide euthanasia. The tissue was washed and the lumen was flushed with ice cold water prior to homogenization in 500 ml ice cold 30% acetic acid. The homogenate was clarified by centrifugation, lyophilized, dissolved in 200 ml 30% acetic acid, clarified by filtration through Whatman 541 filter paper and aDDlied to a 10×60 cm Bio-Gel P-60 column equilibrated with 30% acetic acid. The elution rate was 100 ml/hr. Fractions containing cryptdins were identified by electrophoresis in acid-urea polyacrylamide gels (Selsted and Harwig, *Infect. Immun.* 55:2281–2285 (1987), which is incorporated herein by reference).

Cryptdin-containing fractions were pooled and lyophilized, then purification was completed by RP-HPLC. Initial separation of mouse cryptdins 2–5 was achieved by HPLC on a 1×25 cm Vydac C-18 column using a gradient of water and acetonitrile containing 0.13% HFBA. Solvents were delivered at 3 ml/min to generate the following acetonitrile gradient: 0–28% (10 min); 28–34% (20 min); and 34–40% (60 min). Cryptdins 1 and 6, which co-eluted under these conditions, were resolved by C-18 RP-HPLC using 0.1% TFA as the ion pair and a 16–21% acetonitrile gradient delivered in 35 min at 3 ml/min. To eliminate traces of residual HFBA, preparations of cryptdins 2–5 were subjected to an addition RP-HPLC step using 0.1% TFA. All peptides were lyophilized and quantitated by amino acid analysis prior to antimicrobial testing. Essentially identical methods were used to purify rat and human cryptdin peptides, except that rat cryptdins were isolated from the small intestine of adult Sprague-Dawley rats and human cryptdins were isolated from a surgically resected normal adult human male small intestine.

EXAMPLE II

Peptide Characterization

Amino acid analyses were performed on 6 N HCl hydrolysates (150° C., 2 hr) of unmodified or performic acid-oxidized peptides. Hydrolysates were derivatized with phenylisothiocyanate and the resulting phenylthiocarbamyl amino acids were quantitated ag described previously (Selsted and Harwig, supra, 1987; Selsted et al., supra, 1992; Ouellette et al., *FEBS Lett.* 304:146–148 (1992), which is incorporated herein by reference). Peptide samples were reduced with dithiothreitol (DTT) and pyridylethylated with 4-vinyl pyridine for sequencing (Henschen, In *Advanced Methods in Protein Microsequence Analysis* (Wittmann-Liebold et al., pages 244–255 (1986), which is incorporated herein by reference). Sequence determinations were performed by automated Edman degradation on an ABI model 477 system (Applied Biosystems, Ince Foster City Calif.) with on-line PTH amino acid analysis. In some cases, the C-terminus of a cryptdin peptide was confirmed by amino acid analysis of chymotryptic peptiaes. Cryptdins 4 and 5 also were analyzed by positive-ion fast atom bombardment mass spectrometry on a VG 7070E-HF instrument (Ouellette et al., supra, 1994).

EXAMPLE III

Antimicrobial Assays

Antibacterial activity was measured in an agar radial diffusion assay (Lehrer et al., supra, 1991b) using wild type *S. typhimurium* (ATCC 10428) or an isogenic phoP mutant of *S. typhimurium* (strain CS015 phoP102::Tn10d-Cam, Miller et al., supra, 1989). Cells were grown to log phase in trypticase soy broth at 37° C., harvested by centrifugation and resuspended to $1 \times 10^7$ colony forming units (CFU) per ml in 10 mM sodium phosphate buffer (pH 7.4).

A 100 μl aliquot of each organism was mixed with 10 ml 1% agarose in 0.03% (w/v) trypticase soy medium, 10 mM sodium phosphate (pH 7.4) at 42° C. Five μl samples of peptide solution were pipetted into 3 mm diameter wells formed in the agarose with a sterile punch. After 3 hr at 37° C., the inoculated agarose plate was overlayed with 1% agarose containing 6% trypticase soy medium. After 12–16 hr, antimicrobial activity was apparent as clear zones surrounding wells loaded with antibacterial samples; the sizes of the clear zones were concentration-dependent.

Cryptdin antimicrobial activity in vitro was substantially enhanced in piperazine-N,N'-bis (2-ethane sulfonic acid) (PIPES) or in N-2-hydroxyethylpiperazine-N'-2-ethanesulfonic acid (HEPES) as compared to the activity in sodium phosphate. Purified cryptdin peptides were dissolved at 3 to 300 μg/ml in 0.010% acetic acid and activity was examined against *E. coli* ML35 (ATCC). In the radial diffusion assay, 5 pl peptide solution was transferred into wells formed in plates of 1% agarose buffered with 10 mM PIPES (pH 7.4) and containing $1 \times 10^6$ log-phase bacteria grown in trypticase soy broth. After 3 hr at 37° C., the plates were overlayed with 0.8w agarose containing 2× trypticase soy broth and incubated overnight. The antibacterial activities of cryptdin peptides was compared with the activity of rabbit neutrophil defensin NP-1, which was purified from peritoneal exudates as described by Selsted et al. (*J. Biol. Chem.* 260:4579–4584 (1985), which is incorporated herein by reference). Antibacterial activity was determined by measuring the diameter of learing around each well and plotted as a function of peptide concentration.

As shown in FIG. 12, each cryptdin peptide produced a doge-depAndent zone Of clearing, which indicates that *E. coli* growth was inhibited. The potencies of the cryptdins varied, with cryptdins 1, 3 and 6 showing similar activity, which was about 3–5× greater than the activity of cryptdin 2. Cryptdin 5 waB approximately 5× moro active than rabbit NP-1 at concentration above 100 μg/ml (FIG. 12.C.) and cryptdin 4 was at least 50× more active than NP-1 when compared at 100 μg/ml and 300 μg/ml (FIG. 12.B.). These higher concentrations of cryptdins 4 and 5 also were more effective than the same concentration of NP-1 at inhibiting the growth of *S. aureus* and of wild type and mutant strains of *S. typhimurium* (not shown). These results demonstrate that various cryptdin peptides can inhibit bacterial growth.

In order to determine whether the effect of the cryptdin peptides against *E. coli* is bacteriostatic or bacteriocidal, bacterial killing was quantitated as a function of time. Bactericidal asgayg were performed by incubating $1–2 \times 10^6$ log-phase bacteria in 10 mM PIPES containing 10 μg peptide/ml. After incubation for 15 or 30 min at 37° C., aliquots were removed, serially diluted and plated on trypticase soy agar. Bactericidal activity was quantitated by counting colonies after overnight incubation at 37° C.

As shown in FIG. 13, cryptdins 1 and 3–6 rapidly killed the *E. coli* cells. In each of these cases, survival was reduced to less than 1k after only 15 min incubation. Cryptdin 2 was the only peptide tested that was not bactericidal under the assay condition. Cryptdins 2 and 3 differ only at amino acid position 10 (threonine and lysine, respectively).

The bactericidal activity of rat cryptdin 1 also was examined. *E. coli* ML35 cells, *S. areus* 502A cells or mutant or wild type *S. typhimuruim* cells were incubated with various concentrations of rat cryptdin 1 or rabbit NP-1. Ten μg/ml rat cryptdin 1 killed about 90% of the *S. areus* cells and greater than 99% of the *E. coli* and mutant *S. typhimuruim* cells, but was relatively ineffective in killing wild type *S. typhimuruim* (not shown). Rat cryptdin 1 was more effective than NP-1 in killing the *E. coli* and mutant *S. typhimuruim* cells, whereas NP-1 was more effective in killing *S. areus*.

The effect of mouse cryptdins 1–3 and 6 at inhibiting the growth of the protozoan, *Giardia lablia*, which is the most common cause of protozoan disease in the human small intestine, also was examined. Briefly, trophozoites of the C6 clone of *Giardia lamblia* WB (ATCC 30957) were grown to late log phase in TYI-S-33 medium containing bovine bile. Free-swimming trophozoites were discarded and tubes with attached trophozoites were refilled with warm Dulbecco's PBS. Trophozoites were detached by chilling 10 min on ice, then harvested by centrifugation, resuspended at $2 \times 10^7$/ml in 25 mM HEPES (pH 7.5) containing 9% (isotonic) sucrose and incubated for 2 hr at 37° C. with variqou Concentrations ot mouse cryptdins 1–3 or 6. Following incubation, trophozoite viability was determined by trypan blue exclusion.

The cryptdin peptides killed Giardia trophozoites in a dose-dependent manner (not shown). In particular, 20 μg/ml of cryptdin 2 or cryptdin 3 reduced Giardia growth by greater than 2 orders of magnitude (not shown). These results indicate that cryptdins are active against a variety of microorganisms.

EXAMPLE IV

Anti-cryptdin Antibody

A polyclonal rabbit antibody was prepared to a synthetic analogue of cryptdin 1. The peptide, termed cryptdin C, corresponding to residues 4–35 in cryptdin 1 (SEQ ID NO; 6; FIG. 1) was synthesized by solid phase chemistry using N-butoxycarbonyl protection (Kent, *Ann. Rev. Biochem.* 57:957–989 (1988), which is incorporated herein by reference). Following cleavage/deprotection of synthetic cryptdin C with TFA-trifluoromethanesulfonic acid, the peptide was precipitated in ethyl ether and dried in vacuo. A 100 mg sample was dissolved in 10 ml 6.0 M guanidine-HCl, 0.2 M Tris-HCl, pH 8.2, containing 20 mg DTT. The sample was purged with nitrogen, heated to 50° C. for 4 hr and diluted 100-fold with deionized water, then was dialyzed exhaustively, first against 0.1 M sodium phosphate (pH 8.2), 20 mM guanidine-HCl, 100 mM NaCl, then against 5% acetic acid. The sample was lyophilized, dissolved in 10 ml 51 acetic acid and subjected to RP-HPLC on a 1×25 cm Vydac C-18 column. The earliest eluting peak, representing about 0.5% of the crude peptide, was determined by amino acid analysis to have the desired composition.

A sample (1.5 mg) of cryptdin C was supplied, without conjugation to carrier, to Berkeley Antibody company (Berkeley, Calif.) for immunization of 2 New Zealand White rabbits. Serum samples were collected for 12 weeks, until the anti-cryptdin C titer, determined by ELISA, reached about 1:10,000 for each rabbit. IgG was isolated from antiserum using DEAR Econo-Pac chromatography (Bio-Rad; Richmond Calif.) as described by the manufacturer.

EXAMPLE V

Immunohistochemistry

Paraffin sections of formalin-fixed mouse mid-small bowel were deparaffinized, treated with 1.1% hydrogen peroxide for 40 min, then washed extensively with water followed by PBS. Slides were treated for 20 min at 37° C. with 500 μg/ml trypsin in PBS, washed twice with PBS, and blocked by incubation for 20 min with 50 porcine serum. Slides were incubated for 20 min in rabbit anti-cryptdin IgG (1:10 dilution relative to serum IgG concentration), then washed with blocking serum. Porcine anti-rabbit IgG was used as linking reagent between the primary antibody and rabbit antiperoxidase-peroxidase conjugate (Dako; Carpinteria Calif.). Diaminobenzidine was used as peroxidase substrate and parallel incubations were performed using equivalent dilutions of rabbit preimmune IgG as the primary antibody.

EXAMPLE VI

Preparation of Synthetic Cryotdin 1

This example provides a method for synthesizing, purifying and characterizing synthetic cryptdin 1.

A. Synthesis

Synthesis was initiated at the 0.13 mmole scale using Wang resin coupled to flourenylmethoxycarbonyl (Fmoc)-arginine using an acid labile linker. Synthesis was carried out in dimethylformamide (DMF) using (relative to resin substitution) a 3-fold excess of Fmoc-amino acids activated in situ with a 3-fold excess of BOP (benzotriazol-1-yl-oxy-tris (dimethylamino) phosphonium hexafluorophosphate) and HOBt (hydroxybenzotriazole) and a 6-fold molar excess of N-methylmorpholine (Nmm). Fmoc removal during synthetic cycles was achieved using cycles of 50% and 25% piperidine in DMF. The side-chain protection scheme utilized the following Fmoc-amino acids: OtBut-aspartic acid, Pmc-arginine, tBut-tyrosine, tBut-serine, Trt-cysteine, tBoc-lysine, OtBut-glutamic acid, Trt-asparagine, tBut-threonine and Trt-histidine.

The peptide chain was assembled in a Synostat batch synthesizer using single couplings at all additions except at leucine and valine which were double coupled. The cycle sequence is as follows:

1. Wash with DMF 4× for 2 min;
2. Deblock: 50% piperidine 1× for 5 min;
3. Deblock: 25% piperidine 1× for 15 min;
4. Wash with DMF 4× for 2 min;
5. Dissolve amino acids+BOP+HOBt in DMF and transfer to reaction vessel;
6. Add Nmm to RV an d mix for 60 min; and
7. Wash with DMF 1× for 2 min.

After coupling of the amino terminal residue, the terminal Fmoc group was removed using the following cycle:

1. Wash with DMF 4× for 2 min;
2. Deblock: 50% piperidine 1× for 5 min;
3. Deblock: 25% piperidine 1× for 15 min;
4. Wash with DMF 4× for 2 min;
5. Wash with dichloromethane 1× for 5 min;
6. Wash with isopropanol 4× for 5 min;
7. Dry under stream of $N_2$ 1× for 10–20 min; and
8. Dry under vacuum 1× for 12 hr.

The peptide-resin was weighed to determine mass increase. To cleave and deprotect the peptide-resin, it was first reswelled in dichloromethane, then cleaved and deprotected by addition of reagent R (90% trifluoroacetic acid, 15% thioanisole, 3% ethanedithiol, 2% anisole) at a ratio of 10 ml/g peptide-resin. Cleavage/deprotection was carried out under nitrogen for 18 hr at RT.

B. Purification

The cleavage mixture was separated from resin by filtration through a scintered glass funnel, washed with 1–2 ml fresh reagent R and diluted 5-fold with 50% acetic acid. Glacial acetic acid was added to a final acetic acid concentration of 50%. The resulting solution was extracted 3× with 0.33 vol methylene chloride and the aqueous phase was lyophilized to dryness, then dissolved in 50% acetic acid and relyophilized. The extraction and lyophilization steps were repeated 3–4 times, then the dry peptide was dissolved in 30% acetic acid at a concentration of 20 mg/ml and passed over an 800 ml Sephadex G-10 column equilibrated in 30% acetic acid. Peptide-containing fractions were pooled, lyophilized, dissolved in 5% acetic acid, then diluted tenfold with water to a final protein concentration of about 1 mg/ml. The solution was adjusted to pH 8.0 with ammonium hydroxide and mixed rapidly with a magnetic stirrer at RT in a beaker open to room air. The pH was adjusted periodically to pH 8.0 over a period of 4 days. The solution was then acidified with acetic acid to pH 3.5 and lyophilized.

C-18 RP-HPLC using 0.1% TFA-water/acetonitrile gradients was used to purify the folded peptide. Fractions were analyzed on acid-urea gels and compared to natural cryptdin 1. The yield from an initial crude pgptide apreparation of 500 mg was approximately 30 mg.

C. Characterization

Synthetic cryptin 1 was compared to natural peptide on analytical RP-HPLC, SDS-PAGE and under three different conditions on acid-urea PAGE. For analysis on acid-urea PAGE, peptide was electrophoresed either without modification, after reduction with DTT or after performic acid oxidation. Under all conditions described, native and synthetic cryptdin 1 behaved identically. The amino acid compositions of natural and synthetic cryptdin 1 were indistinguishable.

EXAMPLE VII

Cloning of Nucleic Acid Molecules Encoding Cryptdins

Individual crypts were isolated using a modification of the EDTA elution method of Bjerknes and Cheng, supra, 1981, as described by Cano-Gauci et al., *Expt. Cell Res.* 208:344–349 (1993), which is incorporated herein by reference. Briefly, the central 10 cm of small intestine from an adult C3H/HeJ mouse was everted on a Buchler gradient-making apparatus, then intact crypts were dislodged by vibration in ice cold 30 mM EDTA in calcium-free, magnesium-free PBS. Isolated crypts were disrupted in a sonicating water bath prior to cDNA synthesis.

The crypt library was constructed by mRNA-directed PCR amplification (Cano-Gauci et al., supra, 1992). Phage were screened at a density of approximately 300 PFU/dish using the partial cDNA clone, asb4/134, as a probe (Ouellette et al., supra, 1989a). Positive phage were collected and denatured plasmid cDNA was sequenced by the dideoxynucleotide termination method using Sequenase™ (U.S. Biochemical Corp.; Cleveland Ohio). Sequencing primers included T3 and T7 promoter primers and Defcr$_{p130}$, which is a 16-mer that corresponds to nucleotides 90–105 in cryptdin 1 mRNA (Huttner et al., *Genomics* 19: 448–453 (1994), which is incorporated herein by reference). Reaction mixtures were separated by electrophoresis in gels consisting of 5% Long Ranger™ (AT Biochem, Inc.; Malvern Pa.) and DNA sequence data were analyzed (Ouellette et al., supra, 1994). Computations for similarity searches of DNA sequences in nonredundant nucleic acid and protein sequence databases were performed at the National Center for Biotechnology Information with the BLAST network service (Ouellette et al., supra, 1994).

A cDNA library also was prepared by amplification of cryptdin mRNA (Huttner et al., supra, 1994). Total RNA was isolated from the small intestine of a male 129/SVJ mouse using RNaZOl™ (Biotecx Lab; Houston Tex.). First strand cDNA synthesis was performed using the cDNA Cycle Kit (Invitrogen; San Diego Calif.). Amplification of 5' ends was performed using the 5' RACE method (Frohman et al., *Proc. Natl. Acad. Sci. USA* 85:8998–9002 (1988), which is incorporated herein by reference) with a reverse primer that was specific for a conserved region of the cryptdin 3'-untranslated sequence (UTS).

Blot hybridization of the PCI products using an oligonucleotide probe specific for the cryptdin preprocoding region detected a single band. DNA from the band was Isolated using the Geneclean II™ kit (Biolol; La Jolla Calif.) subcloned into the Bluescript II plasmid using the pCR-Script SK(+) cloning kit (Stratagene) and transfected into competent XL-1 Blue cells (Stratagene). Colonies containing cryptdin-related sequences were identified by hybridization to a labeled asb4/134 probe. DNA sequence analysis of the positive clones was performed as described above, except that internal primers were utilized as required.

Using these methods, cDNA sequences encoding 17 distinct mouse cryptdin peptides were identified (FIG. 10; SEQ ID NOS: 40–56). The various mouse cryptdin cDNA sequences share 93–100% nucleotide sequence identity with cryptdin 1, except cryptdin 5 and cryptdin 4 share 73% and 69% sequence identity, respectively, with cryptdin 1.

The amino acid sequencek were deduced from the cDNA sequences for the 17 mouse cryptdins (see FIG. 9.A.; SEQ ID NOS: 23 to 39). As shown in FIG. 9.A., the cDNA sequences encode ptprto-cryptdin peptides consisting of a signal peptide, a propiece and the cryptdin peptide. The prepro-cryptdins, including the mature cryptdin peptide, share signif icant amino acid sequence identity with cryptdin 1, although cryptdins 4 and 5 are less homologous (FIG. 9.B.). Amino acid variability was most striking at position 10 of the mature cryptdin peptide, where either serine, threonine, alanine, isoleucine or lysine can be found. Interestingly, a single nucleotide change in the sequence of cryptdin 2 can account for each of these amino acids. In addition, position 15 can contain arginine or lysine. The amino acid variability among cryptdin peptides can be involved in conferring different antimicrobial properties to the cryptdins.

Mouse cryptdin genomic clones also were obtained and sequenced (Huttner et al., supra, 1994). Asb4/134 was used as a probe to screen a custom-made 129/SVJ mouse genomic library constructed in lambda DASH II (Stratagene Cloning Systems, Inc.; La Jolla Calif.). Approximately 1×10$^6$ phage were screened in duplicate and 25 positive phage were identified. Ten clones were purified and phage DNA was isolated using Qiagen 100 columns (Qiagen, Inc.; Chatsworth Calif.). Southern blots of Eco RI-digested DNA from individual phage were hybridized to asb4/134 and hybridizing fragments m were subcloned into Bluescript II SK™ (Stratagene) or pUC18 (BRL; Gaithersburg Md.) for sequencing.

Sequencing was performed as described above, except that primers were selected based on the cryptdin 1 cDNA sequence and with the expectation that mouse cryptdin genes would be structurally homologous to the rabbit MCP-1 and MCP-2 defensin genes (see Huttner et al., supra, 1994). DNA sequence data were analyzed using the programs of Staden (*Biochem. Soc. Trans.* 12:1005–1008 (1984) and the University of Wisconsin Genetics Computer Group (Devereux et al., *Nucl. Acids Res.* 12:387–395 (1985)). Searches for homology were performed as described above.

As shown in FIG. 11, screening of the genomic library produced nucleic acid sequences that contained the complete coding sequences for mouse cryptdins 1, 2, 3, 5 and (SEQ ID NOS: 58–62) In addition, a homologous gene, designated cryptdin i (Crypi; SEQ ID NO: 63), which apparently was inactivated due to a point mutation that changed a cysteine codon to an in-frame stop codon, was isolated. Examination of the nucleic acid sequences revealed that the cryptdin genes contain two exons, the first of which codes for the 5'-UTS and the prepro-coding region and the second of which encodes the mature cryptdin peptide and the 3'-UTS (not shown; but see FIG. 11.A.). A similar structure has been described for the human cryptdin genes (Jones and Bevins, *J. Biol. Chem.* 267:23216–23225 (1992)).

Similar methods as described above were used to obtain the cDNA sequences encoding rat cryptdins 1–3 (FIGS. 14.A. to 14.C.; SEQ ID NOS: 65–67, respectively), except that RNA was obtained from the small intestine of Sprague-Dawley rats. In addition, genomic DNA sequences encoding rat cryptdins 1–3 (FIGS. 15.A. to 15.C.; SEQ ID NOS: 68–70, respectively) were obtained using methods as described above, except that a genomic library containing Sprague-Dawley DNA cloned in EMBL3 was purchased from Clontech (Palo Alto Calif.).

Although the invention has been described with reference to the disclosed embodiments, it should be understood that various modifications can be made without departing from the spirit of the invention. Accordingly, the invention is limited only by the following claims.

We claim:

1. An aqueous solution comprising a substantially purified cryptdin peptide having an amino acid sequence as follows:

$$X_1\text{-Cys-}X_2\text{-Cys-Arg-}X_3\text{-Cys-}X_4\text{-Glu-}X_5\text{-Cys-}X_6\text{-Cys-Cys-}X_7$$

wherein $X_1$ is 3 to 9 amino acids;
$X_2$ is 1 amino acid;
$X_3$ is 2 or 3 amino acids;
$X_4$ is 3 amino acids;
$X_5$ is 5 amino acids;
$X_6$ is 6 to 10 amino acids; and
$X_7$ is 0 to 9 amino acids.

2. The aqueous solution of claim 1, further comprising a physiologically acceptable carrier.

3. An aqueous solution comprising a substantially purified mouse cryptdin peptide having an amino acid sequence as follows:

$$X_1\text{-Leu-}X_2\text{-Cys-Tyr-Cys-Arg-}X_3\text{-Cys-Lys-}X_4\text{-Glu-}X_5\text{-Gly-Thr-Cys-}X_6\text{-Cys-Cys-}X_7$$

wherein $X_1$ is 3 or 4 amino acids;
$X_2$ is 1 amino acid;
$X_3$ is 3 amino acids;
$X_4$ is 2 amino acids;
$X_5$ is 3 amino acids;
$X_6$ is 6 to 9 amino acids; and
$X_7$ is 0 to 3 amino acids.

4. The aqueous solution of claim 3, wherein $X_1$ of said substantially purified cryptdin peptide is selected from the groups consisting of Leu-Arg-Asp, Gly and Leu-Ser-Lys-Lys (SEQ ID NO: 1).

5. The aqueous solution of claim 3, wherein $X_2$ of said substantially purified cryptdin is selected from the group consisting of Val, Leu and Ile.

6. The aqueous solution of claim 3, wherein $X_3$ of said substantially purified cryptdin is selected from the group consisting of Lys-Gly-His and *Arg-Gly, wherein * is selected from the group consisting of Ser, Thr, Lys, Ile and Ala.

7. The aqueous solution of claim 3, wherein $X_4$ of said substantially purified cryptdin is selected from the group consisting of Gly-Arg, Arg-Arg and Arg-Gly.

8. The aqueous solution of claim 3, wherein $X_5$ of said substantially purified cryptdin is selected from the group consisting of Arg-Met-Asn, Arg-Val-Arg, Arg-Val-Phe, His-Met-Asn and His-Ile-Asn.

9. The aqueous solution of claim 3, wherein $X_6$ of said substantially purified cryptdin is selected from the group consisting of Gly-Ile-Arg-Phe-Leu-Tyr (SEQ ID NO: 2), Arg-Asn-Leu-Phe-Lau-Thr-Phe-Val-Phe (SEQ ID NO; 3), Arg-Arg-Gly-His-Leu-Met-Tyr-Thr-Leu (SEQ ID NO 4) and Arg-Lys-Gly-His-Leu-*-Tyr-Thr-* (SEQ ID NO: 5), wherein * indicates leu or met independently.

10. The aqueous solution of claim 3, wherein $X_7$ of said substantially purified cryptdin is selected from the group consisting of Arg, Ser and Pro-Arg-Arg.

11. The aqueous solution of claim 3, wherein the amino acid sequences $X_1$, Leu, $X_2$ of said substantially purified cryptdin are absent.

12. The aqueous solution of claim 11, further comprising a physiologically acceptable carrier.

13. An aqueous solution comprising a substantially purified cryptdin peptide having an amino acid sequence selected from the group consisting of:

Gly-Leu-Leu-Cys-Tyr-Cys-Arg-Lys-Gly-His-Cys-Lys-Arg-Gly-Glu-Arg-Val-Arg-Gly-Thr-Cys-Gly-Ile-Arg-Phe-Leu-Tyr-Cys-Cys-Pro-Arg-Arg (SEQ ID NO: 12);

Leu-Ser-Lys-Lys-Leu-Ile-Cys-Tyr-Cys-Arg-Ile-Arg-Gly-Cys-Lys-Arg-Arg-Glu-Arg-Val-Phe-Gly-Thr-Cys-Arg-Asn-Leu-Phe-Leu-Thr-Phe- Val-Phe-Cys-Cys-Ser (SEQ ID NO: 13);

Leu-Arg-Asp-Leu-Val-Cys-Tyr-Cys-Arg-Ala-Arg-Gly-Cys-Lys-Gly-Arg-Glu-Arg-Met-Asn-Gly-Thr-cys-Arg-Lys-Gly-His-Leu-Leu-Tyr-Met-Leu-Cys-tys-Arg (SEQ ID NO: 14)

Leu-Lys-Gln-Cys-His-Cys-Arg-Lys-Phe-Cys-Arg-Pro-Tyr-Glu-Lys-Ala-Glu-Gly-Ser-Cys-Arg-Pro-Gly-Leu-Phe-Ile-Lys-Arg-Lys-Ile-Cys- Cys-Ile-Gln-Gln-Trp-Thr-Pro-Gly-Arg-Thr (SEQ ID NO: 15)

Ile-Gly-Arg-Pro-Val-Arg-Arg-Cys-Arg-Cys-Arg-Ala-Asn-Cys-Gly-Pro-Lys-Glu-Tyr-Ala-Thr-Ala-Phe-Cys-Ala-Gln-Gly-Pro-Phe-Lys-Gln- Phe-Lys-Phe-Cys-Cys-Thr (SEQ ID NO: 16)

Ile-Arg-Trp-Pro-Trp-Lys-Arg-Cys-His-Cys-Arg-Ser-Phe-Cys-Arg-Pro-Tyr-Glu-Asn-Ala-Thr-Ser-Phe-Cys-Ala-Gln-Gly-Leu-Phe-Lys-Gln- His-Lys-Phe-Cys-Cys-Leu-Asp-Thr-Trp-Pro-Pro-Arg-Met-Lys (SEQ ID NO: 10)

Thr-Ser-Gly-Ser-Gln-Ala-Arg-Ala-Thr-Cys-Tyr-Cys-Arg-Thr-Gly-Arg-Cys-Ala-Thr-Arg-Glu-Ser-Leu-Ser-Gly-Val-Cys-Glu-Ile-Ser-Gly- Arg-Leu-Tyr-Arg-Leu-Cys-Cys-Arg (SEQ ID NO:18) and Ala-Phe-Thr-Cys-His-Cys-Arg-Arg-Ser-Cys-Tyr-Ser-Thr-Glu-Tyr-Ser-Tyr-Gly-Thr-Cys-Thr-Val-Met-Gly-Ile-Asn-His-Arg-Phe-Cys-Cys-Leu (SEQ ID NO:19).

14. The aqueous solution of claim 13, further comprising a physiologically acceptable carrier.

15. An aqueous solution comprising a substantially purified mouse cryptdin peptide having an amino acid sequence as follows:

$$X_1\text{-Leu-}X_2\text{-Cys-Tyr-Cys-Arg-}X_3\text{-Cys-Lys-}X_4\text{-Glu-}X_5\text{-Gly-Thr-Cys-}X_6\text{-Cys-Cys-}X_7$$

wherein $X_1$ is selected from the group consisting of Leu-Arg-Asp, Leu-Ser-Lys-Lys (SEQ ID NO:1) or Leu-Arg-Gly;

$X_2$ is selected from the group consisting of Val, Leu or Ile;

$X_3$ is selected from the group consisting of Lys-Gly-His or *Arg-Gly, where * is Ser, Thr, Lys, Ile or Ala;

$X_4$ is selected from the group consisting of Gly-Arg, Arg-Arg or Arg-Gly;

$X_5$ is selected from the group consisting of Arg-met-Asn, Arg-Val-Arg, Arg-Val-Phe, His-Met-Asn or His-Ile-Asn;

$X_6$ is selected from the group consisting of Gly-Ile-Arg-Phe-Leu-Tyr (SEQ ID NO: 2), Arg-Arg-Gly-His-Leu-Met-Tyr-Thr-Leu (SEQ ID NO: 4) or Arg-Asn-Leu-Phe-Leu-Thr-Phe-Val-Phe (SEQ ID NO: 3) or Arg-Lys-Gly-His-Leu*Tyr-Thr*Arg-Lys-Gly-His-Leu-*-Tyr-Thr-* (SEQ ID NO: 5), where * independently is Leu or Met; and $X_7$ is selected from the group consisting of Arg, Ser or Pro-Arg-Arg.

* * * * *

UNITED STATES PATENT AND TRADEMARK OFFICE
CERTIFICATE OF CORRECTION

PATENT NO. : 6,300,470 B1
DATED : October 9, 2001
INVENTOR(S) : Selsted et al.

It is certified that error appears in the above-identified patent and that said Letters Patent is hereby corrected as shown below:

Title page,
Item [73], Assignee, please delete "CA (US)", replace therefor with -- CA (US); The Shriner's Hospital for Crippled Children, Tampa, FL (6US) --.

Column 70,
Line 12, after "Asn-Gly-Thr", please delete "-cys-" and replace therefor with -- Cys --.
Line 13, after "Met-Leu-Cys", please delete "-tys-" and replace therefor with -- Cys --.
Line 50, please delete "Arg-met-Asn," and replace therefore with -- Arg-Met-Asn, --.

Signed and Sealed this

Thirteenth Day of July, 2004

JON W. DUDAS
*Acting Director of the United States Patent and Trademark Office*

```
                         SEQUENCE LISTING (1) GENERAL INFORMATION:

(iii) NUMBER OF SEQUENCES: 70

(2) INFORMATION FOR SEQ ID NO:1:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:1:

Leu Ser Lys Lys
1

(2) INFORMATION FOR SEQ ID NO:2:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO:2:

Gly Ile Arg Phe Leu Tyr
1               5

(2) INFORMATION FOR SEQ ID NO:3:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:3:

Arg Asn Leu Phe Leu Thr Phe Val Phe
1               5

(2) INFORMATION FOR SEQ ID NO:4:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:4:

Arg Arg Gly His Leu Met Tyr Thr Leu
1               5
```

```
(2) INFORMATION FOR SEQ ID NO:5:

(i) SEQUENCE CHARACTERISTICS:
        (A) LENGTH: 9 amino acids
        (B) TYPE: amino acid
        (D) TOPOLOGY: linear (ix) FEATURE:
        (A) NAME/KEY: Peptide
        (B) LOCATION: 6
        (D) OTHER INFORMATION: /note= "Xaa = Amino acid is
            independently L or M."

(ix) FEATURE:
        (A) NAME/KEY: Peptide
        (B) LOCATION: 9
        (D) OTHER INFORMATION: /note= "Xaa = Amino acid is
            independently L or M"

(xi) SEQUENCE DESCRIPTION: SEQ ID NO:5:

Arg Lys Gly His Leu Xaa Tyr Thr Xaa
1               5

(2) INFORMATION FOR SEQ ID NO:6:

(i) SEQUENCE CHARACTERISTICS:
        (A) LENGTH: 35 amino acids
        (B) TYPE: amino acid
        (D) TOPOLOGY: linear (xi) SEQUENCE DESCRIPTION: SEQ ID NO:6:

Leu Arg Asp Leu Val Cys Tyr Cys Arg Ser Arg Gly Cys Lys Gly Arg
1               5                   10                  15

Glu Arg Met Asn Gly Thr Cys Arg Lys Gly His Leu Leu Tyr Thr Leu
                20                  25                  30

Cys Cys Arg
        35

(2) INFORMATION FOR SEQ ID NO:7:

(i) SEQUENCE CHARACTERISTICS:
        (A) LENGTH: 35 amino acids
        (B) TYPE: amino acid
        (D) TOPOLOGY: linear (xi) SEQUENCE DESCRIPTION: SEQ ID NO:7:

Leu Arg Asp Leu Val Cys Tyr Cys Arg Thr Arg Gly Cys Lys Arg Arg
1               5                   10                  15

Glu Arg Met Asn Gly Thr Cys Arg Lys Gly His Leu Met Tyr Thr Leu
                20                  25                  30

Cys Cys Arg
        35

(2) INFORMATION FOR SEQ ID NO:8:

(i) SEQUENCE CHARACTERISTICS:
        (A) LENGTH: 35 amino acids
        (B) TYPE: amino acid
        (D) TOPOLOGY: linear (xi) SEQUENCE DESCRIPTION: SEQ ID NO:8:

Leu Arg Asp Leu Val Cys Tyr Cys Arg Lys Arg Gly Cys Lys Arg Arg
1               5                   10                  15

Glu Arg Met Asn Gly Thr Cys Arg Lys Gly His Leu Met Tyr Thr Leu
                20                  25                  30

Cys Cys Arg
```

35

(2) INFORMATION FOR SEQ ID NO:9:

(i) SEQUENCE CHARACTERISTICS:
        (A) LENGTH: 31 amino acids
        (B) TYPE: amino acid
        (D) TOPOLOGY: linear (xi) SEQUENCE DESCRIPTION: SEQ ID NO:9:

```
Gly Leu Leu Cys Tyr Cys Arg Lys Gly His Cys Lys Arg Gly Glu Arg
1               5                   10                  15

Val Arg Gly Thr Cys Gly Ile Arg Phe Leu Tyr Cys Cys Pro Arg
            20                  25                  30
```

(2) INFORMATION FOR SEQ ID NO:10:

(i) SEQUENCE CHARACTERISTICS:
        (A) LENGTH: 35 amino acids
        (B) TYPE: amino acid
        (D) TOPOLOGY: linear (xi) SEQUENCE DESCRIPTION: SEQ ID NO:10:

```
Leu Ser Lys Lys Leu Ile Cys Tyr Cys Arg Ile Arg Gly Cys Lys Arg
1               5                   10                  15

Arg Glu Arg Val Phe Gly Thr Cys Arg Asn Leu Phe Leu Thr Phe Val
            20                  25                  30

Phe Cys Cys
        35
```

(2) INFORMATION FOR SEQ ID NO:11:

(i) SEQUENCE CHARACTERISTICS:
        (A) LENGTH: 39 amino acids
        (B) TYPE: amino acid
        (D) TOPOLOGY: linear (xi) SEQUENCE DESCRIPTION: SEQ ID NO:11:

```
Leu Lys Gln Cys His Cys Arg Lys Phe Cys Arg Pro Tyr Glu Lys Ala
1               5                   10                  15

Glu Gly Ser Cys Arg Pro Gly Leu Phe Ile Lys Arg Lys Ile Cys Cys
            20                  25                  30

Ile Gln Gln Trp Thr Pro Gly
        35
```

(2) INFORMATION FOR SEQ ID NO:12:

(i) SEQUENCE CHARACTERISTICS:
        (A) LENGTH: 32 amino acids
        (B) TYPE: amino acid
        (D) TOPOLOGY: linear (xi) SEQUENCE DESCRIPTION: SEQ ID NO:12:

```
Gly Leu Leu Cys Tyr Cys Arg Lys Gly His Cys Lys Arg Gly Glu Arg
1               5                   10                  15

Val Arg Gly Thr Cys Gly Ile Arg Phe Leu Tyr Cys Cys Pro Arg Arg
            20                  25                  30
```

(2) INFORMATION FOR SEQ ID NO:13:

(i) SEQUENCE CHARACTERISTICS:
        (A) LENGTH: 36 amino acids
        (B) TYPE: amino acid
        (D) TOPOLOGY: linear (xi) SEQUENCE DESCRIPTION: SEQ ID NO:13:

Leu Ser Lys Lys Leu Ile Cys Tyr Cys Arg Ile Arg Gly Cys Lys Arg
1               5                   10                  15

Arg Glu Arg Val Phe Gly Thr Cys Arg Asn Leu Phe Leu Thr Phe Val
                20                  25                  30

Phe Cys Cys Ser
            35

(2) INFORMATION FOR SEQ ID NO:14:

(i) SEQUENCE CHARACTERISTICS:
        (A) LENGTH: 35 amino acids
        (B) TYPE: amino acid
        (D) TOPOLOGY: linear (xi) SEQUENCE DESCRIPTION: SEQ ID NO:14:

Leu Arg Asp Leu Val Cys Tyr Cys Arg Ala Arg Gly Cys Lys Gly Arg
1               5                   10                  15

Glu Arg Met Asn Gly Thr Cys Arg Lys Gly His Leu Leu Tyr Met Leu
                20                  25                  30

Cys Cys Arg
        35

(2) INFORMATION FOR SEQ ID NO:15:

(i) SEQUENCE CHARACTERISTICS:
        (A) LENGTH: 41 amino acids
        (B) TYPE: amino acid
        (D) TOPOLOGY: linear (xi) SEQUENCE DESCRIPTION: SEQ ID NO:15:

Leu Lys Gln Cys His Cys Arg Lys Phe Cys Arg Pro Tyr Glu Lys Ala
1               5                   10                  15

Glu Gly Ser Cys Arg Pro Gly Leu Phe Ile Lys Arg Lys Ile Cys Cys
                20                  25                  30

Ile Gln Gln Trp Thr Pro Gly Arg Thr
        35                  40

(2) INFORMATION FOR SEQ ID NO:16:

(i) SEQUENCE CHARACTERISTICS:
        (A) LENGTH: 37 amino acids
        (B) TYPE: amino acid
        (D) TOPOLOGY: linear (xi) SEQUENCE DESCRIPTION: SEQ ID NO:16:

Ile Gly Arg Pro Val Arg Arg Cys Arg Cys Arg Ala Asn Cys Gly Pro
1               5                   10                  15

Lys Glu Tyr Ala Thr Ala Phe Cys Ala Gln Gly Pro Phe Lys Gln Phe
                20                  25                  30

Lys Phe Cys Cys Thr
            35

(2) INFORMATION FOR SEQ ID NO:17:

(i) SEQUENCE CHARACTERISTICS:
        (A) LENGTH: 45 amino acids
        (B) TYPE: amino acid
        (D) TOPOLOGY: linear (xi) SEQUENCE DESCRIPTION: SEQ ID NO:17:

```
Ile Arg Trp Pro Trp Lys Arg Cys His Cys Arg Ser Phe Cys Arg Pro
1               5                   10                  15

Tyr Glu Asn Ala Thr Ser Phe Cys Ala Gln Gly Leu Phe Lys Gln His
                20                  25                  30

Lys Phe Cys Cys Leu Asp Thr Trp Pro Pro Arg Met Lys
                35                  40                  45
```

(2) INFORMATION FOR SEQ ID NO:18:

(i) SEQUENCE CHARACTERISTICS:
        (A) LENGTH: 39 amino acids
        (B) TYPE: amino acid
        (D) TOPOLOGY: linear (xi) SEQUENCE DESCRIPTION: SEQ ID NO:18:

```
Thr Ser Gly Ser Gln Ala Arg Ala Thr Cys Tyr Cys Arg Thr Gly Arg
1               5                   10                  15

Cys Ala Thr Arg Glu Ser Leu Ser Gly Val Cys Glu Ile Ser Gly Arg
                20                  25                  30

Leu Tyr Arg Leu Cys Cys Arg
        35
```

(2) INFORMATION FOR SEQ ID NO:19:

(i) SEQUENCE CHARACTERISTICS:
        (A) LENGTH: 32 amino acids
        (B) TYPE: amino acid
        (D) TOPOLOGY: linear (xi) SEQUENCE DESCRIPTION: SEQ ID NO:19:

```
Ala Phe Thr Cys His Cys Arg Arg Ser Cys Tyr Ser Thr Glu Tyr Ser
1               5                   10                  15

Tyr Gly Thr Cys Thr Val Met Gly Ile Asn His Arg Phe Cys Cys Leu
                20                  25                  30
```

(2) INFORMATION FOR SEQ ID NO:20:

(i) SEQUENCE CHARACTERISTICS:
        (A) LENGTH: 103 amino acids
        (B) TYPE: amino acid
        (D) TOPOLOGY: linear (xi) SEQUENCE DESCRIPTION: SEQ ID NO:20:

```
Met Lys Thr Leu Val Leu Leu Ser Ala Leu Val Leu Ala Phe Gln
1               5                   10                  15

Val Gln Ala Asp Pro Ile Gln Glu Ala Glu Glu Thr Lys Thr Glu
                20                  25                  30

Glu Gln Pro Ala Asp Glu Asp Gln Asp Val Ser Val Ser Phe Glu Gly
                35                  40                  45

Pro Glu Pro Ser Ala Leu Gln Asn Leu Glu Ile Gly Trp Pro Leu Lys
        50                  55                  60

Gln Cys His Cys Arg Lys Phe Cys Arg Pro Tyr Glu Lys Ala Glu Gly
65              70                  75                  80

Ser Cys Arg Pro Gly Leu Phe Ile Lys Arg Lys Ile Cys Cys Ile Gln
                85                  90                  95

Gln Trp Thr Pro Gly Arg Thr
            100
```

(2) INFORMATION FOR SEQ ID NO:21:

(i) SEQUENCE CHARACTERISTICS:

(A) LENGTH: 96 amino acids
    (B) TYPE: amino acid
    (D) TOPOLOGY: linear (xi) SEQUENCE DESCRIPTION: SEQ ID NO:21:

Met Lys Thr Leu Val Leu Leu Ser Ala Leu Val Leu Val Ala Tyr Gln
1               5                   10                  15

Val Gln Ala Asp Pro Ile Gln Gly Ala Glu Glu Thr Lys Thr Glu
            20                  25                  30

Glu Gln Pro Ser Asp Glu Asp Gln Asp Val Ser Val Ser Phe Glu Gly
                35                  40                  45

Pro Glu Ala Ser Ala Leu Gln Asp Phe Glu Ile Gly Arg Pro Val Arg
    50                  55                  60

Arg Cys Arg Cys Arg Ala Asn Cys Gly Pro Lys Glu Tyr Ala Thr Ala
65                  70                  75                  80

Phe Cys Ala Gln Gly Pro Phe Lys Gln Phe Lys Arg Phe Cys Cys Thr
                85                  90                  95

(2) INFORMATION FOR SEQ ID NO:22:

(i) SEQUENCE CHARACTERISTICS:
    (A) LENGTH: 103 amino acids
    (B) TYPE: amino acid
    (D) TOPOLOGY: linear (xi) SEQUENCE DESCRIPTION: SEQ ID NO:22:

Met Lys Thr Leu Val Leu Leu Ser Ala Leu Val Leu Leu Ala Phe Gln
1               5                   10                  15

Ile Gln Ala Asp Pro Ile Gln Glu Ala Glu Glu Thr Lys Thr Glu
            20                  25                  30

Glu Gln Pro Ala Asp Glu Asp Gln Asp Val Ser Val Ser Phe Glu Gly
                35                  40                  45

Pro Glu Pro Ser Ala Leu Gln Asn Leu Glu Ile Arg Trp Pro Trp Lys
    50                  55                  60

Arg Cys His Cys Arg Ser Phe Cys Arg Pro Tyr Glu Asn Ala Thr Ser
65                  70                  75                  80

Phe Cys Ala Gln Gly Leu Phe Lys Gln His Lys Phe Cys Cys Leu Asp
                85                  90                  95

Thr Trp Pro Pro Arg Met Lys
                100

(2) INFORMATION FOR SEQ ID NO:23:

(i) SEQUENCE CHARACTERISTICS:
    (A) LENGTH: 93 amino acids
    (B) TYPE: amino acid
    (D) TOPOLOGY: linear (xi) SEQUENCE DESCRIPTION: SEQ ID NO:23:

Met Lys Thr Leu Val Leu Leu Ser Ala Leu Val Leu Leu Ala Phe Gln
1               5                   10                  15

Val Gln Ala Asp Pro Ile Gln Asn Thr Asp Glu Glu Thr Lys Thr Glu
            20                  25                  30

Glu Gln Pro Gly Glu Asp Asp Gln Ala Val Ser Val Ser Phe Gly Asp
                35                  40                  45

Pro Glu Gly Thr Ser Leu Gln Glu Glu Ser Leu Arg Asp Leu Val Cys
    50                  55                  60

Tyr Cys Arg Ser Arg Gly Cys Lys Gly Arg Glu Arg Met Asn Gly Thr
65                  70                  75                  80

```
Cys Arg Lys Gly His Leu Leu Tyr Thr Leu Cys Cys Arg
                85                  90
```

(2) INFORMATION FOR SEQ ID NO:24:

(i) SEQUENCE CHARACTERISTICS:
       (A) LENGTH: 93 amino acids
       (B) TYPE: amino acid
       (D) TOPOLOGY: linear (xi) SEQUENCE DESCRIPTION: SEQ ID NO:24:

```
Met Lys Thr Leu Ile Leu Leu Ser Ala Leu Val Leu Ala Phe Gln
1               5                   10                  15

Val Gln Ala Asp Pro Ile Gln Asn Thr Asp Glu Glu Thr Lys Thr Glu
            20                  25                  30

Lys Gln Pro Gly Glu Glu Asp Gln Ala Val Ser Val Ser Phe Gly Asp
        35                  40                  45

Pro Glu Gly Ser Ser Leu Gln Glu Glu Ser Leu Arg Asp Leu Val Cys
    50                  55                  60

Tyr Cys Arg Thr Arg Gly Cys Lys Arg Arg Glu Arg Met Asn Gly Thr
65                  70                  75                  80

Cys Arg Lys Gly His Leu Met Tyr Thr Leu Cys Cys Arg
                85                  90
```

(2) INFORMATION FOR SEQ ID NO:25:

(i) SEQUENCE CHARACTERISTICS:
       (A) LENGTH: 93 amino acids
       (B) TYPE: amino acid
       (D) TOPOLOGY: linear (xi) SEQUENCE DESCRIPTION: SEQ ID NO:25:

```
Met Lys Thr Leu Val Leu Leu Ser Ala Leu Val Leu Ala Phe Gln
1               5                   10                  15

Val Gln Ala Asp Pro Ile Gln Asn Thr Asp Glu Glu Thr Lys Thr Glu
            20                  25                  30

Glu Gln Pro Gly Glu Asp Asp Gln Ala Val Ser Val Ser Phe Gly Asp
        35                  40                  45

Pro Glu Gly Ser Ser Leu Gln Glu Glu Ser Leu Arg Asp Leu Val Cys
    50                  55                  60

Tyr Cys Arg Lys Arg Gly Cys Lys Arg Arg Glu Arg Met Asn Gly Thr
65                  70                  75                  80

Cys Arg Lys Gly His Leu Met Tyr Thr Leu Cys Cys Arg
                85                  90
```

(2) INFORMATION FOR SEQ ID NO:26:

(i) SEQUENCE CHARACTERISTICS:
       (A) LENGTH: 92 amino acids
       (B) TYPE: amino acid
       (D) TOPOLOGY: linear (ix) FEATURE:
       (A) NAME/KEY: Peptide
       (B) LOCATION: 79
       (D) OTHER INFORMATION: /note= "Xaa = Amino acid is
           independently L or M."

(ix) FEATURE:
       (A) NAME/KEY: Peptide
       (B) LOCATION: 80
       (D) OTHER INFORMATION: /note= "Xaa = Amino acid is
           independently L or M."

(ix) FEATURE:
              (A) NAME/KEY: Peptide
              (B) LOCATION: 82
              (D) OTHER INFORMATION: /note= "Xaa = Amino acid is
                  independently L or M."

(xi) SEQUENCE DESCRIPTION: SEQ ID NO:26:

Leu Val Leu Leu Ser Ala Leu Val Leu Leu Ala Phe Gln Val Gln Ala
1               5                   10                  15

Asp Pro Ile Gln Asn Thr Asp Glu Thr Lys Thr Glu Glu Gln Pro
            20                  25                  30

Gly Glu Glu Asp Gln Ala Val Ser Ile Ser Phe Gly Gly Gln Glu Gly
                35                  40                  45

Ser Ala Leu His Glu Lys Ser Leu Arg Gly Leu Leu Cys Tyr Cys Arg
            50                  55                  60

Lys Gly His Cys Lys Arg Gly Glu Arg Val Arg Gly Thr Cys Xaa Xaa
65                  70                  75                  80

Gly Xaa Ile Arg Phe Leu Tyr Cys Cys Pro Arg Arg
                85                  90

(2) INFORMATION FOR SEQ ID NO:27:

(i) SEQUENCE CHARACTERISTICS:
              (A) LENGTH: 93 amino acids
              (B) TYPE: amino acid
              (D) TOPOLOGY: linear (xi) SEQUENCE DESCRIPTION: SEQ ID NO:27:

Met Lys Thr Phe Val Leu Leu Ser Ala Leu Val Leu Leu Ala Phe Gln
1               5                   10                  15

Val Gln Ala Asp Pro Ile His Lys Thr Asp Glu Glu Thr Asn Thr Glu
            20                  25                  30

Glu Gln Pro Gly Glu Glu Asp Gln Ala Val Ser Ile Ser Phe Gly Gly
                35                  40                  45

Gln Glu Gly Ser Ala Leu His Glu Glu Leu Ser Lys Lys Leu Ile Cys
            50                  55                  60

Tyr Cys Arg Ile Arg Gly Cys Lys Arg Arg Glu Arg Val Phe Gly Thr
65                  70                  75                  80

Cys Arg Asn Leu Phe Leu Thr Phe Val Phe Cys Cys Ser
                85                  90

(2) INFORMATION FOR SEQ ID NO:28:

(i) SEQUENCE CHARACTERISTICS:
              (A) LENGTH: 93 amino acids
              (B) TYPE: amino acid
              (D) TOPOLOGY: linear (xi) SEQUENCE DESCRIPTION: SEQ ID NO:28:

Met Lys Thr Leu Val Leu Leu Ser Ala Leu Val Leu Leu Ala Phe Gln
1               5                   10                  15

Val Gln Ala Asp Pro Ile Gln Asn Thr Asp Glu Glu Thr Lys Thr Glu
            20                  25                  30

Glu Gln Pro Gly Glu Glu Asp Gln Ala Val Ser Val Ser Phe Gly Asp
                35                  40                  45

Pro Glu Gly Thr Ser Leu Gln Glu Glu Ser Leu Arg Asp Leu Val Cys
            50                  55                  60

Tyr Cys Arg Ala Arg Gly Cys Lys Gly Arg Glu Arg Met Asn Gly Thr
65                  70                  75                  80

Cys Arg Lys Gly His Leu Leu Tyr Met Leu Cys Cys Arg
                85                  90

(2) INFORMATION FOR SEQ ID NO:29:

(i) SEQUENCE CHARACTERISTICS:
        (A) LENGTH: 93 amino acids
        (B) TYPE: amino acid
        (D) TOPOLOGY: linear (xi) SEQUENCE DESCRIPTION: SEQ ID NO:29:

Met Lys Thr Leu Ile Leu Leu Ser Ala Leu Val Leu Ala Phe Gln
1               5                   10                  15

Val Gln Ala Asp Pro Ile Gln Asn Thr Asp Glu Glu Thr Lys Thr Glu
            20                  25                  30

Glu Gln Pro Gly Glu Asp Asp Gln Ala Val Ser Val Ser Phe Gly Asp
        35                  40                  45

Pro Glu Gly Ser Ser Leu Gln Glu Glu Ser Leu Arg Asp Leu Val Cys
    50                  55                  60

Tyr Cys Arg Thr Arg Gly Cys Lys Arg Glu His Met Asn Gly Thr
65                  70                  75                  80

Cys Arg Lys Gly His Leu Met Tyr Thr Leu Cys Cys Arg
                85                  90

(2) INFORMATION FOR SEQ ID NO:30:

(i) SEQUENCE CHARACTERISTICS:
        (A) LENGTH: 93 amino acids
        (B) TYPE: amino acid
        (D) TOPOLOGY: linear (xi) SEQUENCE DESCRIPTION: SEQ ID NO:30:

Met Lys Thr Leu Val Leu Leu Ser Ala Leu Val Leu Ala Phe Gln
1               5                   10                  15

Val Gln Ala Asp Pro Ile Gln Asn Thr Asp Glu Glu Thr Lys Thr Glu
            20                  25                  30

Glu Gln Pro Gly Glu Glu Asp Gln Ala Val Ser Val Ser Phe Gly Asp
        35                  40                  45

Pro Glu Gly Ser Ser Leu Gln Glu Glu Ser Leu Arg Asp Leu Val Cys
    50                  55                  60

Tyr Cys Arg Lys Arg Gly Cys Lys Arg Arg Glu His Met Asn Gly Thr
65                  70                  75                  80

Cys Arg Lys Gly His Leu Leu Tyr Met Leu Cys Cys Arg
                85                  90

(2) INFORMATION FOR SEQ ID NO:31:

(i) SEQUENCE CHARACTERISTICS:
        (A) LENGTH: 81 amino acids
        (B) TYPE: amino acid
        (D) TOPOLOGY: linear (xi) SEQUENCE DESCRIPTION: SEQ ID NO:31:

Leu Ala Phe Gln Val Gln Ala Asp Pro Ile Gln Asn Thr Asp Glu Glu
1               5                   10                  15

Thr Lys Thr Glu Glu Gln Pro Gly Glu Asp Asp Gln Ala Val Ser Val
            20                  25                  30

Ser Phe Gly Asp Pro Glu Gly Ser Ser Leu Gln Glu Glu Ser Leu Arg
        35                  40                  45

```
Asp Leu Val Cys Tyr Cys Arg Lys Arg Gly Cys Lys Arg Arg Glu His
    50              55                  60
Met Asn Gly Thr Cys Arg Lys Gly His Leu Met Tyr Thr Leu Cys Cys
65              70                  75                  80
Arg
```

(2) INFORMATION FOR SEQ ID NO:32:

(i) SEQUENCE CHARACTERISTICS:
        (A) LENGTH: 92 amino acids
        (B) TYPE: amino acid
        (D) TOPOLOGY: linear (xi) SEQUENCE DESCRIPTION: SEQ ID NO:32:

```
Lys Thr Leu Val Leu Leu Ser Ala Leu Val Leu Leu Ala Phe Gln Val
1               5                   10                  15
Gln Ala Asp Pro Ile Gln Asn Thr Asp Glu Glu Thr Lys Thr Glu Glu
            20                  25                  30
Gln Pro Gly Glu Asp Asp Gln Ala Val Ser Val Ser Phe Gly Asp Pro
        35                  40                  45
Glu Gly Ser Ser Leu Gln Glu Glu Ser Leu Arg Asp Leu Val Cys Tyr
    50                  55                  60
Cys Arg Lys Arg Gly Cys Lys Gly Arg Glu Arg Met Asn Gly Thr Cys
65              70                  75                  80
Arg Lys Gly His Leu Leu Tyr Thr Leu Cys Cys Arg
                85                  90
```

(2) INFORMATION FOR SEQ ID NO:33:

(i) SEQUENCE CHARACTERISTICS:
        (A) LENGTH: 85 amino acids
        (B) TYPE: amino acid
        (D) TOPOLOGY: linear (xi) SEQUENCE DESCRIPTION: SEQ ID NO:33:

```
Ala Leu Val Leu Leu Ala Phe Gln Val Gln Ala Asp Pro Ile Gln Asn
1               5                   10                  15
Thr Asp Glu Glu Thr Lys Thr Glu Glu Gln Pro Gly Glu Glu Asp Gln
            20                  25                  30
Ala Val Ser Val Ser Phe Gly Asp Pro Glu Gly Thr Ser Leu Gln Glu
        35                  40                  45
Glu Ser Leu Arg Asp Leu Val Cys Tyr Cys Arg Ser Arg Gly Cys Lys
    50                  55                  60
Gly Arg Glu Arg Met Asn Gly Thr Cys Arg Lys Gly His Leu Leu Tyr
65              70                  75                  80
Met Leu Cys Cys Arg
                85
```

(2) INFORMATION FOR SEQ ID NO:34:

(i) SEQUENCE CHARACTERISTICS:
        (A) LENGTH: 93 amino acids
        (B) TYPE: amino acid
        (D) TOPOLOGY: linear (xi) SEQUENCE DESCRIPTION: SEQ ID NO:34:

```
Met Lys Thr Leu Ile Leu Leu Ser Ala Leu Val Leu Leu Ala Phe Gln
1               5                   10                  15
Val Gln Ala Asp Pro Ile Gln Asn Thr Asp Glu Glu Thr Lys Thr Glu
            20                  25                  30
```

```
Glu Gln Pro Gly Glu Glu Asp Gln Ala Val Ser Val Ser Phe Gly Asp
            35                  40                  45

Pro Glu Gly Thr Ser Leu Gln Glu Glu Ser Leu Arg Asp Leu Val Cys
 50                  55                  60

Tyr Cys Arg Ala Arg Gly Cys Lys Gly Arg Glu Arg Met Asn Gly Thr
 65                  70                  75                  80

Cys Arg Lys Gly His Leu Met Tyr Thr Leu Cys Cys Arg
                 85                  90

(2) INFORMATION FOR SEQ ID NO:35:

(i) SEQUENCE CHARACTERISTICS:
        (A) LENGTH: 93 amino acids
        (B) TYPE: amino acid
        (D) TOPOLOGY: linear (xi) SEQUENCE DESCRIPTION: SEQ ID NO:35:

Met Lys Thr Leu Val Leu Leu Ser Ala Leu Val Leu Ala Phe Gln
 1               5                  10                  15

Val Gln Ala Asp Pro Ile Gln Asn Thr Asp Glu Glu Thr Lys Thr Glu
            20                  25                  30

Glu Gln Pro Gly Glu Glu Asp Gln Ala Val Ser Val Ser Phe Gly Asp
            35                  40                  45

Pro Glu Gly Thr Ser Leu Gln Glu Glu Ser Leu Arg Asp Leu Val Cys
 50                  55                  60

Tyr Cys Arg Lys Arg Gly Cys Lys Arg Arg Glu His Met Asn Gly Thr
 65                  70                  75                  80

Cys Arg Arg Gly His Leu Met Tyr Thr Leu Cys Cys Arg
                 85                  90

(2) INFORMATION FOR SEQ ID NO:36:

(i) SEQUENCE CHARACTERISTICS:
        (A) LENGTH: 85 amino acids
        (B) TYPE: amino acid
        (D) TOPOLOGY: linear (xi) SEQUENCE DESCRIPTION: SEQ ID NO:36:

Ala Leu Val Leu Leu Ala Phe Gln Val Gln Ala Asp Pro Ile Gln Asn
 1               5                  10                  15

Thr Asp Glu Glu Thr Lys Thr Glu Glu Gln Pro Gly Glu Glu Asp Gln
            20                  25                  30

Ala Val Ser Val Ser Phe Gly Asp Pro Glu Gly Ser Ser Leu Gln Glu
            35                  40                  45

Glu Ser Leu Arg Asp Leu Val Cys Tyr Cys Arg Thr Arg Gly Cys Lys
 50                  55                  60

Arg Arg Glu Arg Met Asn Gly Thr Cys Arg Lys Gly His Leu Met His
 65                  70                  75                  80

Thr Leu Cys Cys Arg
            85

(2) INFORMATION FOR SEQ ID NO:37:

(i) SEQUENCE CHARACTERISTICS:
        (A) LENGTH: 93 amino acids
        (B) TYPE: amino acid
        (D) TOPOLOGY: linear (xi) SEQUENCE DESCRIPTION: SEQ ID NO:37:
```

-continued

```
Met Lys Thr Leu Val Leu Leu Ser Ala Leu Val Leu Ala Phe Gln
1               5                   10                  15

Val Gln Ala Asp Pro Ile Gln Asn Thr Asp Glu Glu Thr Lys Thr Glu
            20                  25                  30

Glu Gln Pro Gly Glu Asp Gln Ala Val Ser Val Ser Phe Gly Asp
            35                  40                  45

Pro Glu Gly Ser Ser Leu Gln Glu Glu Ser Leu Arg Asp Leu Val Cys
    50                  55                  60

Tyr Cys Arg Lys Arg Gly Cys Lys Arg Arg Glu His Ile Asn Gly Thr
65                  70                  75                  80

Cys Arg Lys Gly His Leu Leu Tyr Met Leu Cys Cys Arg
                85                  90
```

(2) INFORMATION FOR SEQ ID NO:38:

(i) SEQUENCE CHARACTERISTICS:
        (A) LENGTH: 93 amino acids
        (B) TYPE: amino acid
        (D) TOPOLOGY: linear (xi) SEQUENCE DESCRIPTION: SEQ ID NO:38:

```
Met Lys Thr Leu Ile Leu Leu Ser Ala Leu Val Leu Ala Phe Gln
1               5                   10                  15

Val Gln Ala Asp Pro Ile Gln Asn Thr Asp Glu Glu Thr Lys Thr Glu
            20                  25                  30

Glu Gln Pro Gly Glu Glu Asp Gln Ala Val Ser Val Ser Phe Gly Asp
            35                  40                  45

Pro Glu Gly Thr Ser Leu Gln Glu Glu Ser Leu Arg Asp Leu Val Cys
    50                  55                  60

Tyr Cys Arg Ser Arg Gly Cys Lys Gly Arg Glu Arg Met Asn Gly Thr
65                  70                  75                  80

Cys Arg Lys Gly His Leu Met Tyr Thr Leu Cys Cys Arg
                85                  90
```

(2) INFORMATION FOR SEQ ID NO:39:

(i) SEQUENCE CHARACTERISTICS:
        (A) LENGTH: 82 amino acids
        (B) TYPE: amino acid
        (D) TOPOLOGY: linear (xi) SEQUENCE DESCRIPTION: SEQ ID NO:39:

```
Leu Leu Ala Phe Gln Val Gln Ala Asp Pro Ile Gln Asn Thr Asp Glu
1               5                   10                  15

Glu Thr Lys Thr Glu Glu Gln Pro Gly Glu Asp Gln Ala Val Ser
            20                  25                  30

Val Ser Phe Gly Asp Pro Glu Gly Thr Ser Leu Gln Glu Glu Ser Leu
            35                  40                  45

Arg Asp Leu Val Cys Tyr Cys Arg Lys Arg Gly Cys Lys Arg Arg Glu
    50                  55                  60

His Met Asn Gly Thr Cys Arg Lys Gly His Leu Leu Tyr Thr Leu Cys
65                  70                  75                  80

Cys Arg
```

(2) INFORMATION FOR SEQ ID NO:40:

(i) SEQUENCE CHARACTERISTICS:
        (A) LENGTH: 422 base pairs
        (B) TYPE: nucleic acid (C) STRANDEDNESS: double
        (D) TOPOLOGY: linear (xi) SEQUENCE DESCRIPTION: SEQ ID NO:40:

ACACATTGAG CTCCTGCTCA CCAATCCTCC AGGTGACTCC CAGCCATGAA GACACTAGTC    60

CTCCTCTCTG CCCTTGTCCT GCTGGCCTTC CAGGTCCAGG CTGATCCTAT CCAAAACACA   120

GATGAAGAGA CTAAAACTGA GGAGCAGCCA GGGGAAGACG ACCAGGCCGT ATCTGTCTCC   180

TTTGGAGACC CAGAAGGCAC TTCTCTTCAA GAGGAATCGT TGAGAGATCT GGTATGCTAT   240

TGTAGATCAA GAGGCTGCAA AGGAAGAGAA CGCATGAATG GGACCTGCAG AAAGGGTCAT   300

TTATTGTACA CGCTCTGCTG TCGCTGAACA TGGAGACCAC AGAGGACAAG ACGAACATGA   360

GTACTGAGGC CACTGATGCT GGTGCCTGAT GACCACTTCG CAATAAATTG TTCGCAATAT   420

GC                                                                 422

(2) INFORMATION FOR SEQ ID NO:41:

(i) SEQUENCE CHARACTERISTICS:
        (A) LENGTH: 422 base pairs
        (B) TYPE: nucleic acid
        (C) STRANDEDNESS: double
        (D) TOPOLOGY: linear (xi) SEQUENCE DESCRIPTION: SEQ ID NO:41:

ACACACTGAG CCGCTACTCA CCAATCCTCC AGGTGACTCC CAGCCATGAA GACACTAATC    60

CTCCTCTCTG CCCTCGTCCT GCTGGCCTTC CAGGTCCAGG CTGATCCTAT CCAAAATACA   120

GATGAAGAGA CTAAAACTGA GAAGCAGCCA GGGGAAGAGG ACCAGGCCGT ATCTGTCTCC   180

TTTGGAGACC CAGAAGGCTC TTCTCTTCAA GAGGAATCGT TGAGAGATCT GGTATGCTAT   240

TGTAGAACAA GAGGCTGCAA AAGAAGAGAA CGCATGAATG GGACCTGCAG AAAGGGTCAT   300

TTAATGTACA CGCTCTGCTG TCGCTGAACA TGGAGACCAC AGAGGACAAG ATGACCATGA   360

GTACTGAGGC CACTGATGCT GGTGCCTGAT GACCACTTCG CAATAAATTG CTTGCAATAT   420

GC                                                                 422

(2) INFORMATION FOR SEQ ID NO:42:

(i) SEQUENCE CHARACTERISTICS:
        (A) LENGTH: 422 base pairs
        (B) TYPE: nucleic acid
        (C) STRANDEDNESS: double
        (D) TOPOLOGY: linear (xi) SEQUENCE DESCRIPTION: SEQ ID NO:42:

ACACATTGGG CTCCTGCTCA CCAATCCTCC AGGTGACTCC CAGCCATGAA GACACTAGTC    60

CTCCTCTCTG CCCTCGTCCT GCTGGCCTTC CAGGTCCAGG CTGATCCTAT CCAAAACACA   120

GATGAAGAGA CTAAAACTGA GGAGCAGCCA GGGGAAGACG ACCAGGCCGT ATCTGTCTCC   180

TTTGGAGACC CAGAAGGCTC TTCTCTTCAA GAGGAATCGT TGAGAGATCT GGTATGCTAT   240

TGTAGAAAAA GAGGCTGCAA AAGAAGAGAA CGCATGAATG GGACCTGCAG AAAGGGTCAT   300

TTAATGTACA CACTCTGCTG TCGCTGAACA TGGAGACCAC AGAGGACAAG ACGAACATGA   360

GTACTGAGGC CACTGATGCT GGTGCCTGAT GACCACTTCG CAATAAATTG TTCGCAATAT   420

GC                                                                 422

(2) INFORMATION FOR SEQ ID NO:43:

(i) SEQUENCE CHARACTERISTICS:

(A) LENGTH: 365 base pairs
        (B) TYPE: nucleic acid
        (C) STRANDEDNESS: double
        (D) TOPOLOGY: linear (xi) SEQUENCE DESCRIPTION: SEQ ID NO:43:

ACTAGTCCTC CTCTCTGCCC TCGTCCTGCT GGCCTTCCAG GTCCAGGCTG ATCCTATCCA    60

AAATACAGAT GAAGAGACTA AAACTGAGGA GCAGCCAGGG GAAGAGGACC AGGCCGTATC   120

TGTCTCCTTT GGAGACCCAG AAGGCTCTGC TCTTCATGAA AAATCTTTGA GAGGTTTGTT   180

ATGCTATTGT AGAAAAGGAC ACTGCAAAAG AGGAGAACGA GTTCGTGGGA CTTGTGGAAT   240

ACGATTTTTG TACTGCTGCC CCCGCCGCTG AACATGCAGA TGACAAAGAT ATGACAACCA   300

TTGTCTCTGA GGCCGCTGAT GCCGGGGCCT GATGACCACT TCTCAAGAAA TGTTTGCAAT   360

ATGCA                                                              365

(2) INFORMATION FOR SEQ ID NO:44:

(i) SEQUENCE CHARACTERISTICS:
        (A) LENGTH: 421 base pairs
        (B) TYPE: nucleic acid
        (C) STRANDEDNESS: double
        (D) TOPOLOGY: linear (xi) SEQUENCE DESCRIPTION: SEQ ID NO:44:

ACACATTGGG CTCCTGCTCA CCAATTCTCC AGGTGACCCC CAGCCATGAA GACATTTGTC    60

CTCCTCTCTG CCCTTGTCCT GCTGGCCTTC CAGGTCCAGG CTGATCCTAT CCACAAAACA   120

GATGAAGAGA CTAATACTGA GGAGCAGCCA GGGGAAGAGG ACCAGGCCGT ATCTATCTCC   180

TTTGGAGGCC AAGAAGGGTC TGCTCTTCAT GAGGAATTGT CAAAAAAGCT GATATGCTAT   240

TGTAGAATAA GAGGCTGCAA AAGAAGAGAA CGCGTTTTTG GGACCTGCAG AAATCTTTTT   300

TTAACTTTCG TATTCTGCTG CAGCTGAATA TGCAGATGAC AAAGATATGA CAACCATCAG   360

CACTGAGGCC ACTGATGCTG GGTCTGATG ATCACCTCGC AATAAATTGT TCGCAATATG    420

C                                                                  421

(2) INFORMATION FOR SEQ ID NO:45:

(i) SEQUENCE CHARACTERISTICS:
        (A) LENGTH: 422 base pairs
        (B) TYPE: nucleic acid
        (C) STRANDEDNESS: double
        (D) TOPOLOGY: linear (xi) SEQUENCE DESCRIPTION: SEQ ID NO:45:

ACACACTGAG CTGCTACTCA CCAATCCTCC AGGTGACTCC CAGCCATGAA GACACTAATC    60

CTCCTCTCTG CCCTCGTCCT GCTGGCCTTC CAGGTCCAGG CTGATCCTAT CCAAAATACA   120

GATGAAGAGA CTAAAACTGA GGAGCAGCCA GGGGAAGAGG ACCAGGCCGT ATCTGTCTCC   180

TTTGGAGACC CAGAAGGCAC TTCTCTTCAA GAGGAATCAT TGAGATATCT GGTATGCTAT   240

TGTAGAGCAA GAGGCTGCAA AGGAAGAGAA CGCATGAATG GGACCTGCAG AAAGGGTCAT   300

TTATTGTACA TGCTCTGCTG TCGCTGAACA TGGAGACCTC AGAGAACAAG ACGACCATGA   360

GTACTGAGGC CACTGATGCT GGTGCCTGAT GACCACTTCG CAATACATTG TTCGCAATAT   420

GC                                                                 422

(2) INFORMATION FOR SEQ ID NO:46:

(i) SEQUENCE CHARACTERISTICS:

(A) LENGTH: 420 base pairs
        (B) TYPE: nucleic acid
        (C) STRANDEDNESS: double
        (D) TOPOLOGY: linear (xi) SEQUENCE DESCRIPTION: SEQ ID NO:46:

ACACTGAGCT GCTACTCACC AATCCTCCAG GTGACTCCCA GCCATGAAGA CACTAATCCT    60

CCTCTCTGCC CTCGTCCTGC TGGCCTTCCA GGTCCAGGCT GATCCTATCC AAAACACAGA    120

TGAAGAGACT AAAACTGAGG AGCAGCCAGG GGAAGACGAC CAGGCCGTAT CTGTCTCCTT    180

TGGAGACCCA GAAGGCTCTT CTCTTCAAGA GGAATCGTTG AGAGATCTGG TATGCTATTG    240

TAGAACAAGA GGCTGCAAAA GAAGAGAACA CATGAATGGG ACCTGCAGAA AGGGTCATTT    300

AATGTACACG CTCTGCTGTC GCTGAACATG GAGACCTCAG AGAACAAGAC GACCATGAGT    360

ACTGAGGCCA CTGATGCTGG TGCCTGATGA CCACTTCGCA ATAAATTGTT CGCAATATGC    420

(2) INFORMATION FOR SEQ ID NO:47:

(i) SEQUENCE CHARACTERISTICS:
        (A) LENGTH: 342 base pairs
        (B) TYPE: nucleic acid
        (C) STRANDEDNESS: double
        (D) TOPOLOGY: linear (xi) SEQUENCE DESCRIPTION: SEQ ID NO:47:

GCTGGCCTTC CAGGTCCAGG CTGATCCTAT CCAAAACACA GATGAAGAGA CTAAAACTGA    60

GGAGCAGCCA GGGGAAGACG ACCAGGCCGT ATCTGTCTCC TTTGGAGACC CAGAAGGCTC    120

TTCTCTTCAA GAGGAATCGT TGAGAGATCT GGTATGCTAT TGTAGAAAAA GAGGCTGCAA    180

AAGAAGAGAA CACATGAATG GGACCTGCAG AAAGGGTCAT TTAATGTACA CGCTCTGCTG    240

TCGCTGAACA TGGAGACCAC AGAGGACAAG ACAAGCATGA GTACTGAGGC CACTGATGCT    300

GGTGCCTGAT GACCACTTCG CAATAAATTG TTCGCAATAT GC                      342

(2) INFORMATION FOR SEQ ID NO:48:

(i) SEQUENCE CHARACTERISTICS:
        (A) LENGTH: 377 base pairs
        (B) TYPE: nucleic acid
        (C) STRANDEDNESS: double
        (D) TOPOLOGY: linear (xi) SEQUENCE DESCRIPTION: SEQ ID NO:48:

ATGAAGACAC TAGTCCTCCT CTCTGCCCTC GTCCTGCTGG CCTTCCAGGT CCAGGCTGAT    60

CCTATCCAAA ACACAGATGA AGAGACTAAA ACTGAGGAGC AGCCAGGGGA AGAGGACCAG    120

GCCGTATCTG TCTCCTTTGG AGACCCAGAA GGCTCTTCTC TTCAAGAGGA ATCGTTGAGA    180

GATCTGGTAT GCTATTGTAG AAAAAGAGGC TGCAAAAGAA GAACACAT GAATGGGACC    240

TGCAGAAAGG GTCATTTATT GTACATGCTC TGCTGTCGCT GAACATGGAG ACCACAGAGG    300

ACAAGATGAA CATGAGTACT GAGGCCACTG ATGCTGGTGC CTGATGACCA CTTCGCAATA    360

AATTGTTCGC AATATGC                                                   377

(2) INFORMATION FOR SEQ ID NO:49:

(i) SEQUENCE CHARACTERISTICS:
        (A) LENGTH: 375 base pairs
        (B) TYPE: nucleic acid
        (C) STRANDEDNESS: double
        (D) TOPOLOGY: linear (xi) SEQUENCE DESCRIPTION: SEQ ID NO:49:

```
GAAGACACTA GTCCTCCTCT CTGCCCTCGT CCTGCTGGCC TTCCAGGTCC AGGCTGATCC      60

TATCCAAAAC ACAGATGAAG AGACTAAAAC TGAGGAGCAG CCAGGGGAAG ACGACCAGGC     120

CGTATCTGTC TCCTTTGGAG ACCCAGAAGG CTCTTCTCTT CAAGAGGAAT CGTTGAGAGA     180

TCTGGTATGC TATTGTAGAA AAAGAGGCTG CAAAGGAAGA GAACGCATGA ATGGAACCTG     240

CAGAAAGGGT CATTTATTGT ACACGCTCTG CTGTCGCTGA ACATGGAGAC CACAGAGGAC     300

AAGACGAACA TGAGTACTGA GGCCACTGAT GCTGGTGCCT GATGACCACT TCGCAATAAA     360

TTGTTCGCAA TATGC                                                     375

(2) INFORMATION FOR SEQ ID NO:50:

(i) SEQUENCE CHARACTERISTICS:
        (A) LENGTH: 352 base pairs
        (B) TYPE: nucleic acid
        (C) STRANDEDNESS: double
        (D) TOPOLOGY: linear (xi) SEQUENCE DESCRIPTION: SEQ ID NO:50:

CCCTCGTCCT GCTGGCCTTC CAGGTCCAGG CTGATCCTAT CCAAAACACA GATGAAGAGA      60

CTAAAACTGA GGAGCAGCCA GGGGAAGAGG ACCAGGCCGT ATCTGTCTCC TTTGGAGACC     120

CAGAAGGCAC TTCTCTTCAA GAGGAATCGT TGAGAGATCT GGTATGCTAT TGTAGATCAA     180

GAGGCTGCAA AGGAAGAGAA CGCATGAATG GAACCTGCAG AAAGGGTCAT TTATTGTACA     240

TGCTCTGCTG TCGCTGAACA TGGAGACCAC AGAGAACAAG ACGACCATGA GTACTGAGGC     300

CACTGATGCT GGTGCCTGAT GACCACTTCG CAATACATTG TTCGCAATAT GC            352

(2) INFORMATION FOR SEQ ID NO:51:

(i) SEQUENCE CHARACTERISTICS:
        (A) LENGTH: 422 base pairs
        (B) TYPE: nucleic acid
        (C) STRANDEDNESS: double
        (D) TOPOLOGY: linear (xi) SEQUENCE DESCRIPTION: SEQ ID NO:51:

ACACATTGGG CTCCTGCTCA CCAATCCTCC AGGTGACTCC CAGCCATGAA GACACTAGTC      60

CTCCTCTCTG CCCTCGTCCT GCTGGCCTTC CAGGTCCAGG CTGATCCTAT CCAAAACACA     120

GATGAAGAGA CTAAAACTGA GGAGCAGCCA GGGGAAGAGG ACCAGGCCGT ATCTGTCTCC     180

TTTGGAGACC CAGAAGGCAC TTCTCTCCAA GAGGAATAGT TGAGAGATCT GGTATGCTAT     240

TGTAGAGCAA GAGGCTGCAA AGGAAGAGAA CGCATGAATG GACCTGCAG AAAGGGTCAT      300

TTAATGTACA CGCTCTGCTG TCGCTGAACA TGGAGACCTC AGAGAACAAG ACGACCATGA     360

GTACTGAGGC CACTGATGCT GGTGCCTGAT GACCACTTCG CAATAAATTG TTCGCAATAT     420

GC                                                                   422

(2) INFORMATION FOR SEQ ID NO:52:

(i) SEQUENCE CHARACTERISTICS:
        (A) LENGTH: 388 base pairs
        (B) TYPE: nucleic acid
        (C) STRANDEDNESS: double
        (D) TOPOLOGY: linear (xi) SEQUENCE DESCRIPTION: SEQ ID NO:52:

GACTCCCAGC CATGAAGACA CTAGTCCTCC TCTCTGCCCT TGTCCTGCTG GCCTTCCAGG      60

TCCAGGCTGA TCCTATCCAA AACACAGATG AAGAGACTAA AACTGAGGAG CAGCCAGGAG     120
```

```
AAGAGGACCA GGCCGTATCT GTCTCCTTTG GAGACCCAGA AGGCACTTCT CTTCAAGAGG      180

AATCGTTGAG AGATCTGGTA TGCTATTGTA GAAAAAGAGG CTGCAAAAGA AGAGAACACA      240

TGAATGGGAC CTGCAGAAGG GGTCATTTAA TGTACACACT CTGCTGTCGC TGAACATGGA      300

GACCACAGAG GACAAGACGA ACATGAGTAC TGAGGCCACT GATGCTGGTG CCTGATGACC      360

ACCTCGCAAT AAATTGTTCG CAATATGC                                        388
```

(2) INFORMATION FOR SEQ ID NO:53:

(i) SEQUENCE CHARACTERISTICS:
        (A) LENGTH: 352 base pairs
        (B) TYPE: nucleic acid
        (C) STRANDEDNESS: double
        (D) TOPOLOGY: linear (xi) SEQUENCE DESCRIPTION: SEQ ID NO:53:

```
CCCTCGTCCT GCTGGCCTTC CAGGTCCAGG CTGATCCTAT CCAAAACACA GATGAAGAGA      60

CTAAAACTGA GGAGCAGCCA GGGGAAGAGG ACCAGGCCGT ATCTGTCTCC TTTGGAGACC     120

CAGAAGGCTC TTCTCTTCAA GAGGAATCGT TGAGAGATCT GGTATGCTAT TGTAGAACAA     180

GAGGCTGCAA AAGAAGAGAA CGCATGAATG GGACCTGCAG AAAGGGTCAT TTAATGCACA     240

CGCTCTGCTG TCGCTGAACA TGGAGACCAC AGAGGACAAG ACGAGCATGA GTACTGAGGC     300

CACTGATGCT GGTGCCTGAT GACCACTTCG CAATAAATTG TTCGCAAAAT GC             352
```

(2) INFORMATION FOR SEQ ID NO:54:

(i) SEQUENCE CHARACTERISTICS:
        (A) LENGTH: 401 base pairs
        (B) TYPE: nucleic acid
        (C) STRANDEDNESS: double
        (D) TOPOLOGY: linear (xi) SEQUENCE DESCRIPTION: SEQ ID NO:54:

```
CCAATCCTCC CAGTGACTCC CAGCCATGAA GACACTAGTC CTCCTCTCTG CCCTTGTCCT      60

GCTGGCCTTC CAGGTCCAGG CTGATCCTAT CCAAAACACA GATGAAGAGA CTAAAACTGA     120

GGAGCAGCCA GGGGAAGACG ACCAGGCCGT ATCTGTCTCC TTTGGAGACC CAGAAGGCTC     180

TTCTCTTCAA GAGGAATCGT TGAGAGATCT GGTATGCTAT TGTAGAAAAA GAGGCTGCAA     240

AAGAAGAGAA CACATAAATG GGACCTGCAG AAAGGGTCAT TTATTGTACA CTCTCTGCTG     300

TCGCTGAACA TGGAGACCAC AGAGGACAAG ATGACCATGA GTACTGAGGC CACTGATGCT     360

GGTGCCTGAT GACCACTCGC AATAAATTGT TCGCAATATG C                         401
```

(2) INFORMATION FOR SEQ ID NO:55:

(i) SEQUENCE CHARACTERISTICS:
        (A) LENGTH: 391 base pairs
        (B) TYPE: nucleic acid
        (C) STRANDEDNESS: double
        (D) TOPOLOGY: linear (xi) SEQUENCE DESCRIPTION: SEQ ID NO:55:

```
GGTGACTCCC AGCCATGAAG ACACTAATCC TCCTCTCTGC CCTCGTCCTG CTGGCCTTCC      60

AGGTCCAGGC TGATCCTATC CAAAACACAG ATGAAGAGAC TAAAACTGAG GAGCAGCCAG     120

GAGAAGAGGA CCAGGCCGTA TCTGTCTCCT TTGGAGACCC AGAAGGCACT TCTCTTCAAG     180

AGGAATCGTT GAGAGATCTG GTATGCTATT GTAGATCAAG AGGCTGCAAA GGAAGAGAAC     240

GCATGAATGG GACCTGCAGA AAGGGTCATT TAATGTACAC GCTCTGCTGT CGCTGAACAT     300
```

```
GGAGACCTCA GAGAACAAGA CGACCATGAG TACTGAGGCC ACTGATGCTG GTGCCTGATG      360

ACCACTTCGC AATAAATTGT TCGCAATATG C                                   391

(2) INFORMATION FOR SEQ ID NO:56:

(i) SEQUENCE CHARACTERISTICS:
        (A) LENGTH: 342 base pairs
        (B) TYPE: nucleic acid
        (C) STRANDEDNESS: double
        (D) TOPOLOGY: linear (xi) SEQUENCE DESCRIPTION: SEQ ID NO:56:

GCTGGCCTTC CAGGTCCAGG CTGATCCTAT CCAAAATACA GATGAAGAGA CTAAAACTGA      60

GGAGCAGCCA GGAGAAGAGG ACCAGGCCGT ATCTGTCTCC TTTGGAGACC CAGAAGGCAC     120

TTCTCTTCAA GAGGAATCGT TGAGAGATCT GGTATGCTAT TGTAGAAAAA GAGGCTGCAA     180

AAGAAGAGAA CACATGAATG GGACCTGCAG AAAGGGTCAT TTATTGTACA CGCTCTGCTG    240

TCGCTGAACA TGGAGACCAC AGAGGACAAG ATGACCATGA GTACTGAGGC CACTGATGCT    300

GGTGCCTGAT GACCACCTCG CAATAAATTG CTTGCAATAT GC                       342

(2) INFORMATION FOR SEQ ID NO:57:

(i) SEQUENCE CHARACTERISTICS:
        (A) LENGTH: 403 base pairs
        (B) TYPE: nucleic acid
        (C) STRANDEDNESS: double
        (D) TOPOLOGY: linear (xi) SEQUENCE DESCRIPTION: SEQ ID NO:57:

ACACATGGCT CTCTCACCAA TCCTCCAGGT GACTCCCAGC CATGAAGACA CTAGTCCTCC      60

TCTCTGCCTG TCCTGCTGGC CTTCCAGGTC CAGGCTGATC CTATCCAAAA CACAGATGAA    120

GAGACTAAAA CTGAGGAGCA GCCAGGGGAA GAGACCAGGC TGTGTCTGTC TCTTTTGGAG    180

ACCCAGAAGG CCTTCTCTTC AAGAGGAATC GTTGAGAGAT CTGGTATGCT ATTGTAGAAA    240

GAGGCTGCAA AGAAGAGAAC CATGAATGGG ACCTGCAGAA AGGGTCATTT ATGTACAGCT    300

CTGCTGTCGC TGAACATGGA GACCCAGAGA CAAGAACATG AGTACTGAGG CCACTGATGC    360

TGGTGCCTGA TGACCACTTC TCAATAAATT GTTCGCAATA TGC                      403

(2) INFORMATION FOR SEQ ID NO:58:

(i) SEQUENCE CHARACTERISTICS:
        (A) LENGTH: 419 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 279..286
        (D) OTHER INFORMATION: /note= "N represents DNA that was
             not sequenced."

(xi) SEQUENCE DESCRIPTION: SEQ ID NO:58:

TATAAATGCA GGCTGGATAT TCACTGTCCA CACATTGAGC TCCTGCTCAC CAATCCTCCA      60

GGTGACTCCC AGCCATGAAG ACACTAGTCC TCCTCTCTGC CCTTGTCCTG CTGGCCTTCC    120

AGGTCCAGGC TGATCCTATC CAAAACACAG ATGAAGAGAC TAAAACTGAG GAGCAGCCAG    180

GAGAAGAGGA CCAGGCCGTA TCTGTCTCCT TTGGAGACCC AGAAGGCACT TCTCTTCAAG    240

AGGAATGTGA GTACTGGTGT CCAGAGTGAT GGATGCTTNN NNNNNNTTTT GTATCTCCAG    300
```

```
CGTTGAGAGA TCTGGTATGC TATTGTAGAT CAAGAGGCTG CAAAGGAAGA GAACGCATGA      360

ATGGAACCTG CAGAAAGGGT CATTTATTGT ACACGCTCTG CTGTCGCTGA ACATGGAGA       419
```

(2) INFORMATION FOR SEQ ID NO:59:

(i) SEQUENCE CHARACTERISTICS:
        (A) LENGTH: 419 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 279..286
        (D) OTHER INFORMATION: /note= "N represents DNA that was
            not sequenced."

(xi) SEQUENCE DESCRIPTION: SEQ ID NO:59:

```
TATAAATGCA GACTGGCTCC TCACTCTCCA CACATTGGGC TCCTGCTCAC CAATCCTCCC       60

AGTGACTCCC AGCCATGAAG CCACTTGTCC TCCTTTCTGC CCTTGTCCTA CTGTCCTTTC      120

AGGTCCAGGC TGATCCTATC CAAAACACAG ATGAAGAGAC TAAAACTGAG GAGCAGTCAG      180

GTGAAGAGGA CCAGGCTGTG TCTGTCTCCT TTGGAGACCG AGAAGGCGCT TCTCTTCAAG      240

AAGAATGTGA GTACTGGTGC CCAGTGTGAT GGATGCTTNN NNNNNNTTTT GTGTCTCCAG      300

CGTTGAGAGA TCTGGTATGC TATTGTAGAA CAAGAGGTTG CAAAAGAAGA GAACGCATGA      360

ATGGGACCTG CAGAAAGGGT CATTTAATGT ACACGCTCTG CTGCCGCTGA ACATGGAGA       419
```

(2) INFORMATION FOR SEQ ID NO:60:

(i) SEQUENCE CHARACTERISTICS:
        (A) LENGTH: 419 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 279..286
        (D) OTHER INFORMATION: /note= "N represents DNA that was
            not sequenced."

(xi) SEQUENCE DESCRIPTION: SEQ ID NO:60:

```
TATAAATGCA GGCTGGATAT TCACTCTCCA CACATTGGGC TCCTGCTCAC CAATCCTCCA       60

GGTGACTCCC AGCCATGAAG ACACTAGTCC TCCTCTCTGC CCTCGTCCTG CTGGCCTTCC      120

AGGTCCAGGC TGATCCTATC CAAAACACAG ATGAAGAGAC TAAAACTGAG GAGCAGCCAG      180

GGGAAGACGA CCAGGCTGTG TCTGTCTCTT TTGGAGACCC AGAAGGCTCT TCTCTTCAAG      240

AGGAATGTGA GTATTGGTGT CCTGTGTGAT GGATGCTTNN NNNNNNTTTT GTGTCTCCAG      300

CGTTGAGAGA TCTGGTATGC TATTGTAGAA AAAGAGGCTG CAAAAGAAGA GAACGCATGA      360

ATGGGACCTG CAGAAAGGGT CATTTAATGT ACACACTCTG CTGTCGCTGA ACATGGAGA       419
```

(2) INFORMATION FOR SEQ ID NO:61:

(i) SEQUENCE CHARACTERISTICS:
        (A) LENGTH: 419 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 279..286

(D) OTHER INFORMATION: /note= "N represents DNA that was
    not sequenced."

(xi) SEQUENCE DESCRIPTION: SEQ ID NO:61:

TATAAATGCA AGTTGGCTAC TCACTCTCCA CACATTGGGC TCCTGCTCAC CAATTCTCCA        60

GGTGACCCCC AGCCATGAAG ACATTTGTCC TCCTCTCTGC CCTTGTCCTG CTGGCCTTCC       120

AGGTCCAGGC TGATCCTATC CACAAAACAG ATGAAGAGAC TAATACTGAG GAGCAGCCAG       180

GGGAAGAGGA CCAGGCTGTG TCAGTCTCCT TTGGAGGCCA AGAAGGGTCT GCTCTTCATG       240

AAGAATGTGA GTAGTGGTAC GCAGTGTGAT GGATGCTTNN NNNNNNTTTT GTGTCTCCAG       300

TGTCAAAAAA GCTGATATGC TATTGTAGAA TAAGAGGCTG CAAAAGAAGA GAACGCGTTT       360

TTGGGACCTG CAGAAATCTT TTTTTAACTT TCGTATTCTG CTGTAGCTGA ATATGCAGA        419

(2) INFORMATION FOR SEQ ID NO:62:

(i) SEQUENCE CHARACTERISTICS:
        (A) LENGTH: 419 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 279..286
        (D) OTHER INFORMATION: /note= "N represents DNA that was
            not sequenced."

(xi) SEQUENCE DESCRIPTION: SEQ ID NO:62:

TATAAATGCA GGCTGGATAT TCACTCTCCA CACACTGAGC TGCTACTCAC CAATCCTCCA        60

GGTGACTCCC AGCCATGAAG ACACTAATCC TCCTCTCTGC CCTCGTCCTG CTGGCCTTCC       120

AGGTCCAGGC TGATCCTATC CAAAATACAG ATGAAGAGAC TAAAACTGAG GAGCAGCCAG       180

GGGAAGAGGA CCAGGCTGTG TCTGTCTCTT TTGGAGACCC AGAAGGCACT TCTCTTCAAG       240

AGGAATGTGA GTACTGGTGT CCAGTGTGAT GGATGCTTNN NNNNNNTTTT GTGTCTCCAG       300

CATTGAGAGA TCTGGTATGC TATTGTAGAG CAAGAGGCTG CAAAGGAAGA GAACGCATGA       360

ATGGGACCTG CAGAAAGGGT CATTTATTGT ACATGCTCTG CTGTCGCTGA ACATGGAGA        419

(2) INFORMATION FOR SEQ ID NO:63:

(i) SEQUENCE CHARACTERISTICS:
        (A) LENGTH: 419 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 279..286
        (D) OTHER INFORMATION: /note= "N represents DNA that was
            not sequenced."

(xi) SEQUENCE DESCRIPTION: SEQ ID NO:63:

ACTTGAGGGT AACAGCCTCT CCCAATTCCA CACATTGAGC TCCTGCTCAC CAATCCTCCA        60

GGTGACTCCC AGCCATGAAG ACACTAGTCC TCCTCTCTGC CCTTGCCCTG CTGGCCTTCC       120

AAGTCCAGGC TGATCCTATC CAAAACACAG ATGAAGAGAC TAAAACTGAG GAGCAGCCAG       180

GGAAAGAAGA CCAAGCTGTT TCTGTCTCCT TTGGAGACCC AGAAGGCTCT TCTCTTCAAG       240

AGGAATGTGA GTACTGGTGC CCAGTGTGAT GGATGCTTNN NNNNNNTTTT GTGTCTCCAG       300

CGTTGAGAGA TCTGATATGA TATTGTAGAA CAAGAGGCTG CAAAAGAAGA GAACGCCTGA       360

```
ATGGGACCTG AAGAAAGGGT CATTTATTGT ACATGCTCTG CTGCTGCTGA ACATGGAGA        419
```

(2) INFORMATION FOR SEQ ID NO:64:

(i) SEQUENCE CHARACTERISTICS:
        (A) LENGTH: 411 base pairs
        (B) TYPE: nucleic acid
        (C) STRANDEDNESS: single
        (D) TOPOLOGY: linear (xi) SEQUENCE DESCRIPTION: SEQ ID NO:64:

```
TATAAATGCA RRCTGGMTMY TCACTNTCCA CACATTGRGC TCCTGCTCAC CAATCCTCCA        60

GGTGACTCCC AGCCATGAAG ACACTWGTCC TCCTCTCTGC CCTYGTCCTG CTGGCCTTCC        120

AGGTCCAGGC TGATCCTATC CAAAAHACAG ATGAAGAGAC TAAAACTGAG GAGCAGCCAG        180

GDGAAGARGA CCAGGCTGTD TCTGTCTCYT TTGGAGACCV AGAAGGCDCT TCTCTTCAAG        240

ARGAATGTGA GTABTGGTGY CCAGTGTGAT GGATGCTTTT TTGTGTCTCC AGCGTTGAGA        300

GATCTGRTAT GCTATTGTAG ADHAAGAGGC TGCAAARGAA GAGAACGCVT GAATGGGACC        360

TGCAGAAAGG GTCATTTAWT GTACANNCTC TGCTGYRGCT GAACATGGAG A                411
```

(2) INFORMATION FOR SEQ ID NO:65:

(i) SEQUENCE CHARACTERISTICS:
        (A) LENGTH: 445 base pairs
        (B) TYPE: nucleic acid
        (C) STRANDEDNESS: double
        (D) TOPOLOGY: linear (xi) SEQUENCE DESCRIPTION: SEQ ID NO:65:

```
ACACTGGTCT CCAGCTCACC AATCCTCCAG GTGACTTCCA GCCATGAAGA CTCTTGTCCT        60

CCTCTCTGCC CTTGTCCTGC TGGCATTCCA GGTCCAGGCT GATCCCATTC AAGAGGCAGA        120

AGAAGAGACT AAAACTGAGG AGCAGCCAGC AGATGAGGAC CAGGATGTGT CTGTCTCCTT        180

TGAAGGCCCA GAACCCTCTG CTCTTCAAAA TTTAGAGATA GGATGGCCAT TAAAGCAGTG        240

CCATTGCCGA AAGTTCTGCA GACCTTATGA AAAGGCCGAG GGGTCCTGTC GTCCAGGTCT        300

ATTTATAAAA CGCAAAATCT GCTGCATACA ACAATGGACA CCAGGGAGGA CATAACCACG        360

TGAACTGGGA CCTCACAATC TGTCATTCTT GGGCTTCAAC TCGACTGCTT TTCCTTCTCC        420

AATAAACCCC TTGCAGACAA AAAAA                                             445
```

(2) INFORMATION FOR SEQ ID NO:66:

(i) SEQUENCE CHARACTERISTICS:
        (A) LENGTH: 445 base pairs
        (B) TYPE: nucleic acid
        (C) STRANDEDNESS: double
        (D) TOPOLOGY: linear (xi) SEQUENCE DESCRIPTION: SEQ ID NO:66:

```
ACACTGGTCT CCAGCTCACC AATCCTCCAG GTGACTTCCA GCCATGAAGA CTCTTGTCCT        60

CCTCTCTGCC CTTGTCCTGG TGGCCTACCA GGTCCAGGCT GATCCCATTC AAGGGGCAGA        120

AGAAGAGACT AAAACTGAAG AGCAACCATC AGATGAGGAC CAGGATGTGT CTGTCTCCTT        180

TGAAGGCCCA GAAGCCTCTG CTCTTCAAGA TTTTGAGATA GGAAGGCCAG TGAGGAGGTG        240

CCGTTGCAGA GCAAACTGCG GACCTAAAGA ATATGCCACT GCGTTCTGTG CTCAAGGTCC        300

ATTTAAACAG TTCAAATTCT GCTGCACATG AACATGGATC CCAAGTCTGA GATAACCACG        360

TGCTCTGGGA CCTCACAATC TGTCATTATT GTGCTTGACC TCAACTGCTT TTCCTTCTCC        420
```

```
AATAAACTCC TGGCAGACAA AAAAA                                              445

(2) INFORMATION FOR SEQ ID NO:67:

(i) SEQUENCE CHARACTERISTICS:
        (A) LENGTH: 445 base pairs
        (B) TYPE: nucleic acid
        (C) STRANDEDNESS: double
        (D) TOPOLOGY: linear (xi) SEQUENCE DESCRIPTION: SEQ ID NO:67:

ACACTGGTCT CCAGCTCACC AATCCTCCAG GTGACTTCCA GCCATGAAGA CTCTTGTCCT         60

CCTCTCTGCC CTTGTCCTGC TGGCATTCCA GATCCAGGCT GATCCCATTC AAGAGGCAGA        120

AGAAGAGACT AAAACTGAGG AGCAGCCAGC AGATGAGGAC CAGGATGTGT CTGTCTCCTT        180

TGAAGGCCCA GAACCCTCTG CTCTTCAAAA TTTAGAGATC AGATGGCCAT GGAAGAGGTG        240

CCATTGCAGA AGTTTCTGCA GACCTTATGA AAATGCCACT TCGTTCTGTG CTCAAGGTCT        300

ATTTAAACAA CACAAATTCT GCTGCCTAGA ACATGGCCC CCAAGGATGA ATAACCACG         360

TGCTCTGGGA CCTCACAATC TGTCATCATT GTGCTTGGCC TCAACTTCTT TTCCTTCTCC        420

AATAAACTCC TTGCAGACAA AAAAA                                              445

(2) INFORMATION FOR SEQ ID NO:68:

(i) SEQUENCE CHARACTERISTICS:
        (A) LENGTH: 2457 base pairs
        (B) TYPE: nucleic acid
        (C) STRANDEDNESS: double
        (D) TOPOLOGY: linear (xi) SEQUENCE DESCRIPTION: SEQ ID NO:68:

CCTGAGACCA ACTCTGTGAT AATCAGAAAA GTCAATAATG TGTCTGAAAT GTAAGGTGTG         60

CTTCTTGACT GATAGTTCTA AGCCTACAGA GAGATTCATG TGGTCATATC CCATTTAACA        120

ATGATATATA TGTTAAATAT ATAAAGATAT ATGTATGTTC AGTATGTATG TTCAATATGT        180

ATGTAAATAA TATTCTTGCT GCTTCACTAG CTTTTACACA GAGCTGTAAG TAAAAACATT        240

GTAGCCAATG AATAGTATTT ATTAACATGT AAATAGGAGC TGGCACCTGT GACAGTGGGA        300

CTCCATACAC TGACTGTAAA CAACAGGATG CTCTGGACCT TTTGCTGTGT GTGTGGTGAG        360

AGACATGGGA TAAACACAGA CTGAAGAGTG TTCCTGAATG ACATGGCGGC ACTTCTCGAG        420

ACCGGGTAGC AGCTTCTGAG CCTCTCTACA TTGTGGATGT CCTTTCCTGT AGGTCAGGTC        480

TCATTGTCTA AAAGTAAAAG CATTGCAGCA TCTCAGACCT GGGAAACACC CCATGGCTTG        540

AGGGTCCTGA GCATGAAGAG CCACCTGGAG CTCACTCTTG GCAGATGTGT TCCATGACTT        600

TGGCTTCTTC AGAACAACCC ACTACAGCTT CACTCTGACA AATCCTAGAA ACTTGAACTC        660

AATTCACTAG AGGGCACCAT AAAGCCATCA TACCTTATAA TGGCCCCAAA GGAGGTGATT        720

CACAAAGTTT GCCTTGATGA GGACAATTGC TAATACACAA AAACTTGCAA AAAAAAATTG        780

AGTGTCCAGT CCACCTGGTC AAGGACTGGT CCCGGATCCA CAGTTTCTGA GAATAGCAGG        840

CTCTAACTTG AAAACACAAA AATTGTTTGT TCTATGAGCT CATTAAATTA GGCAGTGTTC        900

AGCTATTTTC TTTCCTGACC ACTGAGAGGT AAATACTCAA GCAGATGGGA AACAGGGGAG        960

GACAGTAAAG CCTGTTCATC ATTATCAGTG GGAGTGTGCA TGAGGGGAGG GGTGTCAGTG       1020

AACACACAGA GCATCAGGAA GGAAGCCTTG AGGACAGAGG AACATCAAAG GGATCCTGAG       1080

GACAACAGCT GGGAGCAGTT GCCATCAATG AGTGCCTTCT CTAAGTATGG GGCATGTTCT       1140

TTGCCCTATA AATGCAGGCT GGCTTCTCTC TCCACACACT GGTCTCCAGC TCACCAATCC       1200
```

-continued

```
TCCAGGTGAC TTCCAGCCAT GAAGACTCTT GTCCTCCTCT CTGCCCTTGT CCTGCTGGCA    1260

TTCCAGGTCC AGGCTGATCC CATTCAAGAG GCAGAAGAAG AGACTAAAAC TGAGGAGCAG    1320

CCAGCAGATG AGGACCAGGA TGTGTCTGTC TCCTTTGAAG GCCCAGAACC CTCTGCTCTT    1380

CAAAATTTAG GTGCGTGCTT GTGCACAGAA TGATGGAGGC TTGGAGTCTC CTGATGGAGG    1440

GTTGTAGATT AGCCCTGGAG TCCTGTCAAG GACAGTCTGG TTCAGGTAGC TGTCTACTGA    1500

TCCTTTCAGA ACTTCCCTGT CTTATTCATA GAAATAACAG TGAGAGACAA GCCATTGGGC    1560

TTGACTTTTT CCTTTTAAGA TTTCGGTCTA ACAATTTATC TGTGAAAAAC CTTTAAAATA    1620

TAAAACATAT TGATTAGTTC TTTAAACCTG AGTGATAATT TTCTTACAGG AAGAAATATC    1680

CGTTTTACCC TAAAAATTAG ATTGGTACCC AAATGCCAGT GTATGAAGGT GTTGGGTCAA    1740

GAAAACACAA AAAAACTGTT AGAATATGGT GTAGATGAAA ATTCCTATAT GTGATTAACA    1800

CTTGTTAAAC ATCTTATCTC CATGTGTTTG GGGTTGATCA CTGTGCTGGC TGTGATGTCA    1860

CCCACACAGC AAACCTACTC TCTACCATGC ACAGGACATC TTCATGGGGT AGTTCACTGT    1920

TACACACTAC TGGCCTCCTT ACTTCATGCC TGATGCTTTC TTGTTTCCTC AGAGATAGGA    1980

TGGCCATTAA AGCAGTGCCA TTGCCGAAAG TTCTGCAGAC CTTATGAAAA GGCCGAGGGG    2040

TCCTGTCGTC CAGGTCTATT TATAAAACGC AAAATCTGCT GCATACAACA ATGGACACCA    2100

GGGAGGACAT AACCACGTGA ACTGGGACCT CACAATCTGT CATTCTTGGG CTTCAACTCG    2160

ACTGCTTTTC CTTCTCCAAT AAACCCCTTG CAGACAAATA ACCTGTTTAT GTTTTTTTGA    2220

TGCTTTCTAT GTGGCGTAGA CAGGACTCTC CTGAGCCATG TAGCAAAATC TTCAGTGAAT    2280

CCTTTGTAAA AGAAGTCTTG GTCACATTTC AGCAGTCATA TCAAGGATGA GCAGGAGGTT    2340

AGATCCAAAG AGACAAGATG GTCTGCGCCA GCTGCTTCTG TGTCTATCAA GTCTTCTGTC    2400

CTTTAGATTA GAGTCACCCT CAAAAATTAG TTCCAGATTT TCATGTTCTA TTTTTTC      2457
```

(2) INFORMATION FOR SEQ ID NO:69:

(i) SEQUENCE CHARACTERISTICS:
        (A) LENGTH: 2408 base pairs
        (B) TYPE: nucleic acid
        (C) STRANDEDNESS: single
        (D) TOPOLOGY: linear (xi) SEQUENCE DESCRIPTION: SEQ ID NO:69:

```
TATTACGAAT TCGAGCTCGG TACCGGTATA TGAAGAGCGA CCACTGCCAG GACGAAAGTG     60

CAATGCGGCA TACCTCAGTG GCGTGGAGTG CAGGTATACA GATTAATCCG GCAGCGTCCG    120

TCGTTGTTGA TATTGCTTAT GAAGGCTCCG GCAGTGGCGA CTGGCGTACT GACGGATTCA    180

TCGTTGGGGT CGGTTATAAA TTCTGATTAG CCAGGTAACA CAGTGTTATG ACAGCCCGCC    240

GGAACCGGTG GCTTTTTTG TGGGGTGAAT ATGGCAGTAA AGATTTCAGG AGTCCTGAAA    300

GACGGCACAG GAAAACCGGT ACAGAACTGC ACCATTCAGC TGAAAGCCAG ACGTAACAGC    360

ACCACGGTGG TGGTGAACAC GGTGGGCTCA GAGAATCCGG ATGAAGCCTG CTTTTTTATA    420

CTAAGTTGGC ATTATAAAAA AGCATTGCTT ATCAATTTGT TGCAACGAAC AGGTCACTAT    480

CAGTCAAAAT AAAATCATTA TTTGATTTCA ATTTTGTCCC ACTCCCTGCC TCTGTCATCA    540

CGATACTGTG ATGCCATGGT GTCCGACTTA TGCCCGAGAA GATGTTGAGC AAACTTATCG    600

CTTATCTGCT TCTCATAGAG TCTTGCAGAC AAACTGCGCA ACTCGTGAAA GGTAGGCGGA    660

TCTGGGTCGA CTCTAGGCCT CACTGGCCTA ATACGACTCA CTATAGGGAG CTCGAGGATC    720

ATTGCTAATA CCATGAAACT TGACCACCTG GTCAAGGACT GGTCCAGGGT CCACAGTTTC    780
```

```
TGAGAAGAGC AGGCTCCAAC TTCTAACCAC AAAAACTATT TTTTCCATGC GCTCCTTAAA    840

TTAGGCAGCG CCCAGCTATT TTCTTTCCTG ACCACTGAGA GGTAAATACT CAAGCAGATG    900

GGAAACAGGG GAAGATAGCA AGGCCTCTTC ATCATTATCA CTGGGTGTGT GCGTGAGGGG    960

AGGGGTGTCA TTGCATACAC AGGGCAACAT CAGGATGGAA GCCTTGAGGA CAGAGGAACA   1020

TCAAAGGGAT CCTGAGGACA ACAGCTGGGA GCAGTTGCCA TCAGTGAGTG CCTTCTCTAA   1080

GTGTGGGGCC TTTCTCTGCC ACATAAATGC AGGCTGCCTC CTCTCTCCAC ACACTGGTCT   1140

CCAGCTCACC AATCCTCCAG GTGACTTCCA GCCATGAAGA CTCTTGTCCT CCTCTCTGCC   1200

CTTGTCCTGG TGGCCTACCA GGTCCAGGCT GATCCCATTC AAGGGGCAGA AGAAGAGACT   1260

AAAACTGAAG AGCAACCATC AGATGAGGAC CAGGATGTGT CTGTCTCCTT TGAAGGCCCA   1320

GAAGCCTCTG CTCTTCAAGA TTTTGGTGAG TGCTTATGCA CAGAATGATG GAGGCTTGGA   1380

GTCTCCTGAT GGAGGGTTGT AGATTAGACC TGGAATCCTG TCAAGAACTG TCTGGTTCAG   1440

GTAGCTGTCT CTTGGTCCCT TTACATTCCT TGTCTTCTTC ATAGAAGTAA CGGAGAGAGA   1500

TTAACCATTG GGCTTGACTT TTTTCCTTTT AAAATTTTTG ATCTAACAAT TTATCTGTGG   1560

AAAACCTTTA AAATATAAAA CATATTGATT AGTTCTTTTA GACCTGATTG ATAATTTTGT   1620

TATAAGAAGA AATATTCGTT CTACTTTAAA AATTAGATTT GGGACCCAAA TGCCAGTGTA   1680

TGAAGCTGTT GGGTAAGGAA AAACCAAAAA TGGTGATAGA ATGTTGTGTA GATGACAATT   1740

CCTTTATGCG ATTAACACTT TTTAAAATGT CTTATCTCCA TGTGTTTGGG GTTGATCATG   1800

GTGCTGACTG TGATGTCACC CACAGAGCAA ACCTACTCTC TACCATGCAC AGGACATCTT   1860

CATAGGGTAG TTCACTGTCA CACACTGCTG GCCTCGTTAC TTCATGCCTG ATGCTTTCTT   1920

GTTTCCTCAG AGATAGGAAG GCCAGTGAGG AGGTGCCGTT GCAGAGCAAA CTGCGGACCT   1980

AAAGAATATG CCACTGCGTT CTGTGCTCAA GGTCCATTTA AACAGTTCAA ATTCTGCTGC   2040

ACATGAACAT GGATCCCAAG TCTGAGATAA CCACGTGCTC TGGGACCTCA CAATCTGTCA   2100

TTATTGTGCT TGACCTCAAC TGCTTTTCCT TCTCCAATAA ACTCCTGGCA GACAAATAAT   2160

CGGTATATGT TTATTTGATG CTTTCTATTT GGCTTAGACA GAACTCTCCT GAGCCATGTA   2220

GCTGAATCTT CAGTGAATCC TTTGTAAAGG TCACATTTCA GCAGTCATAT CAAGGATGAG   2280

CAGGAGGTTA GATACAAAGA GACAAGATGG TCTGCGCCAG CTGCTTCTTT GTCTATCAAG   2340

TCTGCTTTCC TTTAGATTAG AGTCACCATC AAAAATTATT CCCACATTTT CATGTTCTAT   2400

ATTTTTTT                                                            2408

(2) INFORMATION FOR SEQ ID NO:70:

(i) SEQUENCE CHARACTERISTICS:
        (A) LENGTH: 2551 base pairs
        (B) TYPE: nucleic acid
        (C) STRANDEDNESS: single
        (D) TOPOLOGY: linear (xi) SEQUENCE DESCRIPTION: SEQ ID NO:70:

CCTGAGACCA ACTCTGTGAT AATCAGAAAA GACAATTATG TGTCTTAAAT GTAAGGTTTG     60

CTTCTTGACT GATAGATCTA ACCCTACAGA GAGATTCAAG TGGTCTTGTC CCATTGAACA    120

ATAGTATATA TGTTTTATAT ATATATATAT ATATATGTAT ATGTATATAT ATATGTGTGT    180

GTGTGTGTGT GTGTGTCTGT GTCTGTGTGT CTGTGTGTCT GTGTGTCTGT GTGTCTGTGT    240

GTGTATGTGT GTGTATGTGT ACATATGTTC AATATGTCTG TAAAATAGTA TTCTTGTAGC    300

TTCACTTACT TTTGCACAGA GCTGTAAATA AGAACATTGT AGCCAATGAA TAGTATTTAT    360
```

-continued

```
TAACATGTAA ATAGGAGCTG GCACCTCTGA CAGTGGGACT CCATACAGTG ACTGTAAACA      420
ACAGGATGCT CTAGACCTTT TGCTGTGTGT GTGGTGAGAG ACATGGGATA AACACAGACT      480
GAAGTGTATG ACATGGCGGC ACTTCTCGAG ACCGGGTAGC AGCTTCTGAG CCTCTCTACA      540
TTGTGGATGT CCTTTCCTGT AGGTCAGGTC TCATTGTCTA AAAGTAAAAG CATTGCAGCA      600
TCTCAGACCT GGGAAACACC CCATGGCTTG AGGGTCCCGC AGGTGAAGAG CCACCTGGAG      660
CTCACTCTTG GCAGATGTGT TCCATGACTT TGGCTTCTTC AGAACCACCC ACTACAGCTT      720
CACTCTGACA AATCTTAGAA ACTTGAACTC AATTCACTGG AGGGCACAAT AAAGCCATCT      780
TACTTTCTCT AAAATGGCCC CAAAGGAGGG GATTCACAAA GTTTGCCTTG ATGAGGACCA      840
TTGCTAATAC CCCAAAACTT GCAAAAAAAA TTGAGTGTCC AGTCAACCTG GTCAAGGACT      900
GGTCCTGGAT CCACAGTTTC TGAGAAAAGA AGGCTCCAAC TTCAAAACAC AAACCACTCC      960
TGTTCTATGC GCTCATTAAA TTAGGCAGTG TTAAGCTATT TTCTTTCCTG ACCACTGAGA     1020
GGTAAATACT CAAGCAGATG GGAAACAGGG GAGGACAGCA AAGCCTGTTC ATCATTATCA     1080
GTGGGAGTGT GCGTGAGGGG AGGGGTGTCA GTGAACACAC AGAGCATCAG GAAGGAAGCC     1140
TTGAGGACAG AGGAACATCA AAGGGATCCT GAGGACAACA GCTGGGAGCA GTTGGCATCA     1200
CTGAGTGCCG TCTCTAAGTG TGGGGCCTTT CTCTGCCACA TAAATGCAGG CTGGCTCCTC     1260
TCTCCACACA CTGGTCTCCA GCTCACCAAT CCTCCAGGTG ACTTCCAGCC ATGAAGACTC     1320
TTGTCCTCCT CTCTGCCCTT GTCCTGCTGG CATTCCAGAT CCAGGCTGAT CCCATTCAAG     1380
AGGCAGAAGA AGAGACTAAA ACTGAGGAGC AGCCAGCAGA TGAGGACCAG GATGTGTCTG     1440
TCTCCTTTGA AGGCCCAGAA CCCTCTGCTC TTCAAAATTT AGGTGCGTGC TTGTGCACAG     1500
AATGATGGAG GCTTGGAGTC TCCTGATGGA GGGTTGTAGA TTAGCCCTGG AGTCCTGTCA     1560
AGGACAGTCT GGTTCAGGTA GCTGTCTATT GATCCTTTCA GAACTTCCCT GTCTTATTCA     1620
TAGAAATAAC AGTGAGAGAC AAGCCATTGG GCTTGACTTT TTCCTTTTAA GATTTTGGTC     1680
TAACAATTTA TCTGTGAAAA ACCTTTAAAA TATAAAACAT ATTGATTAGT TCTTTTAAAC     1740
CTGATTGATA ATTTTGTTAT AGGAAGAAAT AACTGTTCTA CTTTAAAAAT TAGATTTGGT     1800
ACCTAAATGC CAGTGTATTA AGGTGTTGGG TCAGGAAAAC ACAATAATGC TGATAGAATG     1860
TGGTGTAGAT GACAATTCCT ATATGCGATT AACACTTGTT AAATTGTCCT ATCTCCATGT     1920
GTTTGGGGTT GATCATGGTG CTGGCTGTGA TGTCACCCAC ACAGCAAACC TACTTTCTAC     1980
CATGCACAGG ACATCTTCAT AGGGTAGTTC ACTGTCACAC ACTGCTGGCC TCCTTACTTC     2040
ATGCCTGATG CTTTCTCGTT TCCTCAGAGA TCAGATGGCC ATGAAGAGG TGCCATTGCA      2100
GAAGTTTCTG CAGACCTTAT GAAAATGCCA CTTCGTTCTG TGCTCAAGGT CTATTTAAAC     2160
AACACAAATT CTGCTGCCTA GAAACATGGC CCCCAAGGAT GAAATAACCA CGTGCTCTGG     2220
GACCTCACAA TCTGTCATCA TTGTGCTTGG CCTCAACTTC TTTTCCTTCT CCAATAAACT     2280
CCTTGCAGAC AAATAACCTG TTTATGTTTT TTTGATGCTT TCTATGTGGC TTAGACAGGG     2340
CTCTCCTGAG CCATGTAGCA GAATCTTCAG TGAATCCTTT GTAAAGAAG TCTTGGTCAC      2400
ATTTCAACAG TCATATCAAG GATGAGCAGG AGGTTAGATC CAAAGAGACA AGATGCTCTG     2460
CTCCAGCTGC TTCTTGACTA TCAAGTCTTC TGTCCTTCAG ATTAGAGTCA CCCTCAAAAA     2520
TTAGTCCCAC CTTTTCATGT TCTATTTTTT T                                    2551
```